United States Patent
Yamaguchi et al.

(10) Patent No.: US 8,022,059 B2
(45) Date of Patent: Sep. 20, 2011

(54) INDAZOLE ACRYLIC ACID AMIDE COMPOUND

(75) Inventors: Tetsuo Yamaguchi, Osaka (JP);
Hiroyuki Kawanishi, Osaka (JP);
Hideki Ushirogochi, Osaka (JP);
Tatsuyuki Takahashi, Osaka (JP);
Tohru Takebe, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 0 days.

(21) Appl. No.: 12/680,497

(22) PCT Filed: Sep. 26, 2008

(86) PCT No.: PCT/JP2008/067393
§ 371 (c)(1),
(2), (4) Date: Mar. 26, 2010

(87) PCT Pub. No.: WO2009/041559
PCT Pub. Date: Apr. 2, 2009

(65) Prior Publication Data
US 2010/0256108 A1   Oct. 7, 2010

(30) Foreign Application Priority Data
Sep. 28, 2007   (JP) .................................. 2007-253463

(51) Int. Cl.
| | |
|---|---|
| *A61K 31/553* | (2006.01) |
| *A61K 31/5377* | (2006.01) |
| *A61K 31/541* | (2006.01) |
| *A61K 31/4427* | (2006.01) |
| *A61K 31/4353* | (2006.01) |
| *A61K 31/4523* | (2006.01) |
| *A61K 31/416* | (2006.01) |
| *C07D 281/02* | (2006.01) |
| *C07D 243/08* | (2006.01) |
| *C07D 413/02* | (2006.01) |
| *C07D 513/02* | (2006.01) |
| *C07D 211/00* | (2006.01) |
| *C07D 401/02* | (2006.01) |
| *C07D 231/56* | (2006.01) |

(52) U.S. Cl. ................ 514/211.15; 514/218; 514/234.2; 514/234.5; 514/303; 514/322; 514/338; 514/406; 540/544; 540/575; 544/127; 544/140; 546/119; 546/199; 546/275.7; 548/362.5

(58) Field of Classification Search ............. 514/210.18, 514/211.15, 218, 234.2, 234.5, 303, 322, 514/338, 406; 540/544, 575; 544/127, 140; 546/119, 199, 275.7; 548/362.5
See application file for complete search history.

(56) References Cited

FOREIGN PATENT DOCUMENTS
| | | |
|---|---|---|
| JP | 10-45716 A | 2/1996 |
| JP | 10-316647 A | 12/1998 |
| WO | WO 03/063797 A2 | 8/2003 |
| WO | WO 2006/011684 A1 | 2/2006 |

OTHER PUBLICATIONS

"Cardiac arrhythimia."http://www.heartrhythmfoundation.org/facts/arrhythmia_prevention.asp Oct. 31, 2010.*
"Atrial Fibrillation."http://www.news-medical.net/health/Atrial-Fibrillation-Prevention.aspx Oct. 31, 2010.*
Antoine Bril. "Recent Advances in Arrhythmia Therapy: Treatment and Prevention of Atrial Fibrillation", A. Curr. Opin Pharmacol., vol. 2, 2002, pp. 154-159.
Bertaso et al., "Expression of Voltage-Gated K+ Channels In Human Atrium", Basic Res. Cardiol., vol. 97, 2002, pp. 424-433.
Dan M. Roden, "Current Status of Class III Antiarrhythmic Drug Therapy", Am. J. Cardiol., vol. 72, Aug. 26, 1993, pp. 44B-49B.
Deng et al., "Effects of Carvedilol on Transient Outward and Ultra-Rapid Delayed Rectifier Potassium Currents in Human Atrial Myocytes", Life Sciences, vol. 80, Jan. 23, 2007, pp. 665-671.
English-language translation of International Preliminary Report on Patentability and Written Opinion of the International Search Autority (PCT/IB/373 and PCT/ISA/237), in PCT/JP2008/067393.
Fuster et al., "ACC/AHA/ESC Guidelines for the Management of Patients with Atrial Fibrillation; Executive Summary", Circulation, vol. 104, 2001, pp. 2118-2150.
Knobloch et al., "Electrophysiological and Antiarrhythmic Eff. of the Novel IKur Chan Blockers S9947 and S20951, on Left vs. Right Pig Atrium in Vivo in Compar. with the IKr Blockers Dofetilide, Azimilide, d,I-sotalol and Ibutilide", Naunyn-Schmedieberg's Arch Pharmacol., vol. 366,2002, pp. 482-487.

(Continued)

*Primary Examiner* — Rebecca Anderson
*Assistant Examiner* — Samantha Shterengarts
(74) *Attorney, Agent, or Firm* — Birch, Stewart, Kolasch & Birch, LLP

(57) ABSTRACT

A compound of the formula:

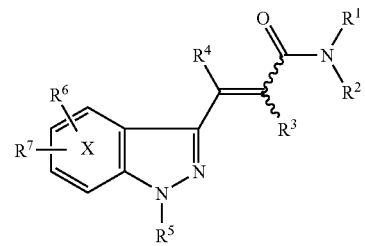

wherein ring X is benzene or pyridine; $R^1$ is substituted alkyl; $R^2$ is optionally substituted aryl or optionally substituted heterocyclic group; $R^3$ is hydrogen or alkyl; $R^4$ is hydrogen, halogen or alkyl; $R^5$ is hydrogen or alkyl; $R^6$ and $R^7$ are the same or different and each hydrogen or halogen, or a pharmaceutically acceptable salt thereof, which is useful as $I_{Kur}$ blocker effective for preventing or treating cardiac arrhythmia such as atrial fibrillation.

13 Claims, No Drawings

OTHER PUBLICATIONS

Kooniawee Nademanee, "The Amiodarone Odyssey", J. Am. Coll. Cardiol., vol. 20, No. 5, Nov. 1, 1992, pp. 1063-1065.

Mays et al., "Localization of the Kv1.5 K+ Channel Protein in Expianted Cardiac Tissue", J. Clin. Invest, vol. 96, Jul. 1995, pp. 282-292.

Mounsey et al., "Dofetilide", Circulation, vol. 102, Nov. 21, 2000, pp. 2665-2670.

Peukert et al., "Identification, Synthesis, and Activity of Novel Blockers of the Voltage-Gated Potassium Channel Kv1.5", J. Med. Chem., vol. 46, 2003, pp. 486-498.

Pratt et al., "The Cardiac Arrhythmia Suppression Trial: Background, Interim Results and Implications", Amer. J. Cardiology, vol. 65, Jan. 16, 1990, pp. 20B-29B.

Sanguinetti et al., "Two Components of Cardiac Delayed Rectifier K+ Current", J. Gen. Physiol. vol. 96, Jul. 1990, pp. 195-215.

Singh et al., "A Third Class of Anti-Arriythmic Action, Effects on Atrial and Ventricular Intracellular Potentials and Other Pharmocological Actions on Cardiac Muscle, of MJ 1999 and AH 3474", Br J. Pharmacol., vol. 39, 1970, pp. 675-687.

Singh et al., "The Effect of Amiodarone, A New Anti-Anginal Drug, on Cardiac Muscle", Br. J. Pharmacol. vol. 39, 1970, pp. 657-667.

Stanley Nattel, "New Ideas about Atrial Fibrillation 50 Years On", Nature, vol. 415, Jan. 10, 2002, pp. 219-226.

Suzuki et al., "Inhibitory Effect of Thiopental on Ultra-Rapid Delayed Rectifier K+ Current in H9c2 Cells", J. Pharmacol. Sci., vol. 99, 2006, pp. 177-184.

Torp-Pedersen et al., "Dofetilide: A Class III Anti-Arrhythmic Drug for the Treatment of Atrial Fibrillation", Expert Opin. Invest. Drugs, vol. 9, No. 11, 2000, pp. 2695-2704.

Waldo et al., "Effect of d-sotalol on Mortality in Patients with Left Ventricular Dysfunction After Recent and Remote Myocardial Infarction", Lancet, vol. 348, Jul. 6, 1996, pp. 7-12.

* cited by examiner

INDAZOLE ACRYLIC ACID AMIDE COMPOUND

TECHNICAL FIELD

The present invention relates to a compound with an $I_{Kur}$ blocking activity useful for preventing or treating disease such as atrial fibrillation.

BACKGROUND ART

Atrial fibrillation is one of the most general arrhythmia in clinical stages wherein an irregular and frequent excitation of atrium stops a series of contraction and expansion as an auxiliary pump of atrium, and particularly, an incidence thereof increases with advancing age. Atrial fibrillation is not a fetal arrhythmia, but worsens heart functions and is known to cause a complication such as congestive heart failure, thromboembolism, ventricular fibrillation, etc.

Antiarrhythmic agents placed on the market until now have been developed as therapeutic agents for ventricular arrhythmia and atrial or supraventricular arrhythmia. Malignant ventricular arrhythmia immediately threatens life and requires emergency treatment, and a class Ia (e.g., procainamide, quinidine), a class Ic (e.g., flecainide, propafenone) or a class III (e.g., dofetilide, amiodarone) agent has been used in drug treatment of ventricular arrhythmia. It has been reported that these class I and class III agents prevent a recurrence of atrial fibrillation (Nonpatent Document 1). However, they have potentials to increase mortalities due to their potentially lethal ventricular arrhythmogenic activities (Nonpatent Documents 2 to 4).

Since atrial fibrillation shortens cardiac action potential duration (APD), an APD-prolonging agent may be a therapeutic agent for atrial fibrillation in theory. A prolongation of cardiac APD is caused by increasing inward currents (i.e., Na$^+$ or Ca$^{2+}$ currents which are referred to as $I_{Na}$ or $I_{Ca}$, respectively, hereinafter) or decreasing outward currents of repolarized potassium K. Delayed rectifier ($I_K$) K$^+$ currents are main outward currents involved in a repolarization process of action potential, and transient outward currents ($I_{to}$) and inward rectifier ($I_{K1}$) K$^+$ currents relate to an initial phase and a terminal phase of the repolarization, respectively. In cellular electrophysiological study, $I_K$ comprises two subtypes of pharmacologically and kinetically different K$^+$ currents, i.e., $I_{Kr}$ (rapid activation) and $I_{Ks}$ (delayed activation) (Nonpatent Document 5).

Dofetilide, a class III antiarrhythmic agent, shows an antiarrhythmic activity by blocking $I_K$, which is an $I_K$ rapid activating ingredient and exists in human atrium and ventricle (Nonpatent Document 1). Since an $I_K$ blocker prolongs APD and a refractory period both in atrium and ventricle without affecting conduction itself, it has potentials to be an agent useful in the treatment of arrhythmia such as atrial fibrillation in theory (Nonpatent Document 4). However, it has been reported that said blocker has an arrhythmogenic activity and develops polymorphic torsades de pointes (Nonpatent Document 6).

In contrast, it has been reported that amiodarone has a class III property (Nonpatent Documents 7 and 8). However, since it has various activities on multiple ion channels and is not a selective class III agent, a usage thereof has been strictly limited in terms of adverse effects thereof (Nonpatent Documents 9 to 11). Accordingly, currently available agents such as amiodarone and dofetilide have potentially lethal serious adverse effects such as ventricular arrhythmogenic activities, and hence, a high safe agent with beneficial efficacy has been desired.

Recently, super rapid activated delayed rectifier L$^+$ currents ($I_{Kur}$) which are prolonged outward currents have been identified in human atrial myocyte. $I_{Kur}$ specifically exists in atrium, not in human ventricle. A molecular correlation of $I_{Kur}$ in human atrium is potassium channel referred to as Kv 1.5, and Kv 1.5 mRNA (Nonpatent Document 12) and protein (Nonpatent Document 13) have been detected in human atrial tissues. It has been believed that $I_{Kur}$ widely contributes to a repolarization in human atrium due to a rapid activation and a delayed inactivation thereof. Therefore, it would appear that since a compound having an $I_{Kur}$ blocking activity prolongs a refractory in atrium without delaying a ventricular repolarization and prolonging a refractory period in ventricle, it may resolve adverse effect problems such as an arrhythmia-induced QT extension syndrome after a depolarization found in the current class III agents (Nonpatent Documents 14 and 15).

In contrast, it has been shown that a reentry (reciprocation) is a remarkable mechanism which causes a supraventricular arrhythmia in human (Nonpatent Document 16). Specifically, reciprocations occur at random in different locations in atrium, and atrial fibrillation is caused by several times of repetitions of electrical excitations by a single stimulation. Accordingly, an increase of myocardial refractory by a prolongation of cardiac APD prevents and/or stops reentry arrhythmia Additionally, since cardiac APD depends on contributions of potassium currents $I_{Kr}$, $I_{Ks}$, $I_{Kur}$ which relate to a repolarization phase and transient outward currents $I_{to}$, it is desired that a blocker which acts on any one of these currents prolongs action potential duration and produces an antiarrhythmic effect.

Patent Document 1 discloses useful indazole derivatives as a SGK-1 inhibitor, but the document does not disclose any $I_{Kur}$ blocking activities.

[Patent Document 1] WO2005/011681
[Nonpatent Document 1] Circulation, 102:2665-2670
[Nonpatent Document 2] Am. J. Cardiol., 65:20 B-29B, 1990
[Nonpatent Document 3] Lancet, 348:7-12, 1996
[Nonpatent Document 4] Expert Opin. Invest. Drugs, 9:2695-2704, 2000
[Nonpatent Document 5] J. Gen. Physiol. 1990, 96:195-215
[Nonpatent Document 6] Am. J. Cardiol., 72:44B-49B, 1993
[Nonpatent Document 7] Br. J. Pharmacol., 39:675-687, 1970
[Nonpatent Document 8] Br. J. Pharmacol., 39:657-667, 1970
[Nonpatent Document 9] J. Am. Coll. Cardiol., 20:1063-1065, 1992
[Nonpatent Document 10] Circulation, 104:2118-2150, 2001
[Nonpatent Document 11] A. Curr. Opin. Pharmacol. 2:154-159, 2002
[Nonpatent Document 12] Basic Res. Cardiol., 97:424-433, 2002
[Nonpatent Document 13] J. Clin. Invest., 96:282-292, 1995
[Nonpatent Document 14] J. Med. Chem., 46:486-498, 2003
[Nonpatent Document 15] Naunyn-Schmedieberg's Arch. Pharmacol., 366:482-487, 2002
[Nonpatent Document 16] Nature, 415:219-226, 2002

DISCLOSURE OF INVENTION

Problems to be Resolved by the Invention

The present invention is directed to provide useful compounds for preventing or treating atrial fibrillation having less adverse effects and excellent $I_{Kur}$ blocking activities.

Means of Solving the Problems

According to extensive studies for solving the above problems, the present inventors have found that a compound of the following formula has an excellent $I_{Kur}$ blocking activity, and the present invention has been achieved.

The present invention includes the following embodiments.

1. A Compound of Formula (I):

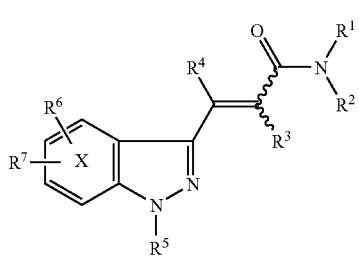

(1)

wherein ring X is benzene or pyridine;
  $R^1$ is a substituted alkyl;
  $R^2$ is an optionally substituted aryl or an optionally substituted heterocyclic group;
  $R^3$ is hydrogen or an alkyl;
  $R^4$ is hydrogen, a halogen or an alkyl;
  $R^5$ is hydrogen or an alkyl;
  $R^6$ and $R^7$ are the same or different and each hydrogen or a halogen; or a pharmaceutically acceptable salt thereof.

2. A Compound of Formula (1-a):

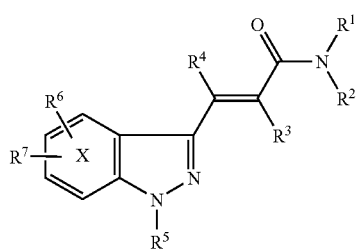

(1-a)

wherein ring X is benzene or pyridine;
  $R^1$ is a substituted alkyl;
  $R^2$ is an optionally substituted aryl or an optionally substituted heterocyclic group;
  $R^3$ is hydrogen or an alkyl;
  $R^4$ is hydrogen, a halogen or an alkyl;
  $R^5$ is hydrogen or an alkyl;
  $R^6$ and $R^7$ are the same or different and each hydrogen or a halogen; or a pharmaceutically acceptable salt thereof.

3. The compound or a pharmaceutically acceptable salt thereof according to either one of the above 1 or 2, wherein $R^1$ is an alkyl substituted with 1 or 2 group(s) selected from hydroxyl, an optionally substituted amino, an alkylsulfonyl, an alkoxy, an optionally substituted heterocyclic group, an optionally substituted ureido, an optionally substituted carbamoyloxy and an optionally substituted heterocyclic group-substituted carbonyloxy.

4. The compound or a pharmaceutically acceptable salt thereof according to any one of the above 1 to 3, wherein $R^2$ is an optionally substituted benzene.

5. The compound or a pharmaceutically acceptable salt thereof according to any one of the above 1 to 4, wherein $R^3$ and $R^4$ are hydrogen.

6. The compound or a pharmaceutically acceptable salt thereof according to any one of the above 1 to 4, wherein $R^3$ is hydrogen and $R^4$ is an alkyl.

7. The compound or a pharmaceutically acceptable salt thereof according to any one of the above 1 to 4, wherein $R^3$ is an alkyl and $R^4$ is hydrogen.

8. The compound or a pharmaceutically acceptable salt thereof according to any one of the above 1 to 4, wherein $R^3$ is hydrogen and $R^4$ is a halogen.

9. The compound or a pharmaceutically acceptable salt thereof according to any one of the above 1 to 8, wherein $R^6$ and $R^7$ are hydrogen.

10. A medicament comprising the compound or a pharmaceutically acceptable salt thereof according to any one of the above 1 to 9.

11. An $I_{Kur}$ blocker comprising as an active ingredient the compound or a pharmaceutically acceptable salt thereof according to any one of the above 1 to 9.

12. A preventive or therapeutic agent for cardiac arrhythmia comprising as an active ingredient the compound or a pharmaceutically acceptable salt thereof according to any one of the above 1 to 9, or a method of treating said disease comprising administering the agent to a patient.

13. A preventive or therapeutic agent for atrial fibrillation comprising as an active ingredient the compound or a pharmaceutically acceptable salt thereof according to any one of the above 1 to 9, or a method of treating said disease comprising administering the agent to a patient.

Each group represented by each symbol in the present specification is illustrated below. Each abbreviation used in the present specification means as defined below.

THF: tetrahydrofuran
  DMF: N,N-dimethylformamide
  DMSO: dimethylsulfoxide
  DMA: dimethylacetamide
  DME: 1,2-dimethoxyethane
  LDA: lithium diisopropylamide
  DBU: 1,8-diazabicyclo[5.4.0]-7-undecene
  DBN: 1,5-diazabicyclo[4.3.0] non-5-ene
  DCC: dicyclohexylcarbodiimide
  WSC: 1-ethyl-3-(3'-dimethylaminopropyl)carbodiimide hydrochloride
  HOBt: 1-hydroxybenzotriazole
  Ac: acetyl
  Me: methyl
  Et: ethyl
  Pr: n-propyl
  $^i$Pr: isopropyl
  t-Bu: t-butyl
  Boc: t-butoxycarbonyl
  Cbz: carbobenzoxy
  Bn: benzyl
  Ph: phenyl
  PMB: p-methoxybenzyl "Alkyl" includes, for example, a straight or branched chain C1 to C6 alkyl, specifically methyl, ethyl, propyl, isopropyl, butyl, isobutyl, tert-butyl, pentyl, hexyl, etc.

"Aryl" includes, for example, a 3- to 15-membered monocyclic, bicyclic or tricyclic aromatic carbocycle, specifically phenyl, naphthyl, phenanthryl, anthryl, etc.

"Heterocyclic group" includes, for example, a 3- to 15-membered monocyclic or bicyclic unsaturated and saturated or partially-saturated heterocyclic group containing 1 to 4 heteroatom(s) selected from nitrogen atom, oxygen atom and sulfur atom.

The unsaturated and saturated or partially-saturated heterocyclic group include, for example, pyrrolyl, imidazolyl, triazolyl, tetrazolyl, pyrazolyl, pyridyl, pyrazinyl, pyrimidinyl, pyridazinyl, azepinyl, diazepinyl, furyl, pyranyl, oxepinyl, thienyl, thiapyranyl, thiepinyl, oxazolyl, isoxazolyl, thiazolyl, isothiazolyl, furazanyl, oxadiazolyl, oxadinyl, oxadiazinyl, oxazepinyl, oxadiazepinyl, thiadiazolyl, thiadinyl, thiadiazinyl, thiazepinyl, thiadiazepinyl, indolyl, isoindolyl, benzofuranyl, benzothiophenyl, indazolyl, quinolinyl, isoquinolinyl, quinoxalinyl, quinazolinyl, benzoxazolyl, benzothiazolyl, benzoimidazolyl, pyrrolinyl, pyrrolidinyl, imidazolinyl, imidazolidinyl, pyrazolinyl, pyrazolidinyl, dihydropyridyl, tetrahydropyridyl, dihydropyrazinyl, tetrahydropyrazinyl, dihydropyrimidinyl, tetrahydropyrimidinyl, dihydroazepinyl, tetrahydroazepinyl, hexahydroazepinyl, dihydrodiazepinyl, tetrahydrodiazepinyl, dihydroxazepinyl, tetrahydroxazepinyl, hexahydroxazepinyl, dihydrofuryl, tetrahydrofuryl, dihydropyranyl, tetrahydropyranyl, dihydrothienyl, tetrahydrothienyl, dihydrothiapyranyl, tetrahydrothiapyranyl, piperidyl, piperazinyl, morpholinyl, thiamorpholinyl, homopiperidyl, etc.

"Alicyclic heterocyclic group" includes, for example, a 5- to 7-membered monocyclic saturated heterocyclic group containing 1 or 2 heteroatom(s) selected from nitrogen atom, oxygen atom and sulfur atom, specifically piperidyl, piperazinyl, morpholinyl, thiomorpholinyl, homopiperidyl, tetrahydrooxadinyl, etc.

"Alkoxycarbonyl" includes, for example, a straight or branched chain C2 to C7 alkoxycarbonyl, specifically methoxycarbonyl, ethoxycarbonyl, propoxycarbonyl, isopropoxycarbonyl, butoxycarbonyl, isobutoxycarbonyl, tert-butoxycarbonyl, etc. A preferable one among them is a C2 to C5 alkoxycarbonyl.

"Halogen" includes fluorine, chlorine, bromine, iodine. A preferable one among them is chlorine or fluorine.

"Alkoxy" includes, for example, a straight or branched chain C1 to C6 alkoxy, specifically methoxy, ethoxy, propoxy, isopropoxy, butoxy, isobutoxy, tert-butoxy, pentyloxy, hexyloxy, etc. A preferable one among them is a C1 to C4 alkoxy.

"Cycloalkyl" includes, for example, a C3 to C8 cycloalkyl, specifically cyclopropyl, cyclobutyl, cyclopentyl, cyclohexyl, cycloheptyl, etc. A preferable one among them is a C3 to C6 cycloalkyl.

"Alkylsulfonyl" and the alkylsulfonyl in "alkylsulfonylamino" includes, for example, a straight or branched chain C1 to C6 alkylsulfonyl, specifically methylsulfonyl, ethylsulfonyl, propylsulfonyl, isopropylsulfonyl, butylsulfonyl, etc. A preferable one among them is a C1 to C4 alkylsulfonyl.

"Arylsulfonyl" includes, for example, a 6- to 15-membered monocyclic or bicyclic aromatic carbocyclyl-substituted sulfonyl, specifically phenylsulfonyl, naphthylsulfonyl, etc.

"Alkanoyl" includes, for example, a straight or branched chain C1 to C6 alkanoyl, specifically formyl, acetyl, propionyl, butyryl, pentanoyl, hexanoyl, etc. A preferable one among them is a C1 to C4 alkanoyl.

"Aralkyl" includes, for example, an aryl (preferably benzene, naphthalene) substituted straight or branched chain C1 to C6 alkyl, preferably C1 to C4 alkyl, specifically benzyl, naphthylmethyl, 2-phenylethyl, 1-phenylethyl, 3-phenylpropyl, etc.

"Haloalkyl" includes, for example, an 1 to 6 halogen(s) substituted straight or branched chain C1 to C6 alkyl, preferably C1 to C4 alkyl, specifically fluoromethyl, chloromethyl, trifluoromethyl, 2,2,2-trifluoroethyl, etc.

"Hydroxyalkyl" includes, for example, an 1 to 3 hydroxyl substituted straight or branched chain C1 to C6 alkyl, preferably C1 to C4 alkyl, specifically hydroxymethyl, 2-hydroxyethyl, 3-hydroxypropyl, etc.

The substituents of "substituted alkyl" in $R^1$ include, for example,
(1) hydroxyl,
(2) an optionally substituted amino,
(3) an alkylsulfonyl,
(4) an arylsulfonyl,
(5) cyano,
(6) an alkoxy,
(7) an optionally substituted heterocyclic group,
(8) an optionally substituted cycloalkyl,
(9) an optionally substituted ureido,
(10) an optionally substituted carbamoyl,
(11) an optionally substituted carbamoyloxy,
(12) a heterocyclic group-substituted carbonyl,
(13) an optionally substituted heterocyclic group-substituted carbonyloxy,
(14) an optionally substituted aminosulfonyl,
(15) an alkoxycarbonyl,
(16) carboxy, etc.,
and the "substituted alkyl" may optionally have the same or different 1 to 3 substituent(s).

The substituents of "optionally substituted amino" in the substituents of the above "substituted alkyl" include, for example, 1 or 2 group(s) selected from the following (A) to (K).
(A) an alkyl optionally substituted with an alkoxy,
(B) an alkanoyl optionally substituted with 1 or 2 group(s) selected from Group a,
(C) an alkanoylamino,
(D) an alkoxycarbonyl optionally substituted with 1 or 2 group(s) selected from Group b,
(E) an alkylsulfonyl optionally substituted with 1 or 2 group(s) selected from Group c,
(F) a heterocyclic group-substituted sulfonyl optionally substituted with 1 or 2 group(s) selected from Group d,
(G) an arylcarbonyl,
(H) an aralkylcarbonyl,
(I) an aminosulfonyl optionally mono- or di-substituted with an alkyl,
(J) a cycloalkylcarbonyl optionally substituted with hydroxyl or cyano, or
(K) a carbamoylcarbonyl optionally mono- or di-substituted with an alkyl, etc.

[Group a]
(a) an alkoxy,
(b) cyano,
(c) a heterocyclic group optionally substituted with 1 to 3 group(s) selected from a halogen, cyano, hydroxyl, an alkoxycarbonyl, and an alkyl optionally substituted with 1 to 3 group(s) selected from a halogen and an alkoxy,
(d) an amino optionally substituted with 1 or 2 group(s) selected from the following (i) to (iii), (i) an alkyl optionally substituted with a group selected from an alkoxy, cyano and an alkylsulfonyl, and an amino optionally substituted with 1 or 2 group(s) selected from an alkylsulfonyl and an alkyl,
 (ii) an alkoxycarbonyl, and
 (iii) an alkanoyl optionally substituted with a group selected from an alkoxy, cyano and an amino optionally mono- or di-substituted with an alkyl,
(e) an alkylsulfonyl,
(f) hydroxyl, and
(g) a halogen
[Group b]
(a) an alkoxy, and
(b) hydroxyl
[Group c]
(a) an alkoxy, and
(b) hydroxyl
[Group d]
(a) hydroxyl,
(b) an alkyl,
(c) a haloalkyl, and
(d) an alkoxycarbonyl The substituents of "optionally substituted heterocyclic group" in the above substituents of the "substituted alkyl" include, for example: (A) oxo, (B) an alkoxycarbonyl, (C) an alkanoyl optionally substituted with cyano, (D) an alkyl optionally substituted with hydroxyl, (E) an alkylsulfonylamino, (F) an alkylsulfonyl, (G) a heterocyclic group-substituted carbonyl, (H) an aminosulfonyl optionally mono- or di-substituted with an alkyl, (I) a carbamoyl optionally mono- or di-substituted with an alkyl or (J) a halogen, and the "optionally substituted heterocyclic group" may optionally have the same or different 1 to 3 substituent(s).

The substituents of "optionally substituted cycloalkyl" in the above substituents of the "substituted alkyl" include, for example, (A) an alkoxy or (B) hydroxyl, and the "optionally substituted cycloalkyl" may optionally have the same or different 1 to 2 substituent(s).

The substituents of "optionally substituted ureido" in the above substituents of the "substituted alkyl" include, for example, an alkyl optionally substituted with a group selected from an alkoxy and hydroxyl, and the "optionally substituted ureido" may optionally have the same or different 1 to 3 substituent(s).

The substituents of "optionally substituted carbamoyl" in the above substituents of the "substituted alkyl" include, for example, the same or different 1 to 2 alkyl(s), etc.

The substituents of "optionally substituted carbamoyloxy" in the above substituents of the "substituted alkyl" include, for example:
(A) a heterocyclic group,
(B) an alkyl optionally substituted with the same or different 1 or 2 group(s) selected from (a) an alkoxy, (b) hydroxyl, (c) cyano, (d) a carbamoyl optionally substituted with the same or different 1 or 2 alkyl(s), etc.

The substituents of "optionally substituted heterocyclic group-substituted carbonyloxy" in the above substituents of the "substituted alkyl" include, for example, (A) hydroxyl, (B) an alkyl, (C) a hydroxyalkyl, (D) an alkanoyl, etc.

The substituents of "optionally substituted aminosulfonyl" in the above substituents of the "substituted alkyl" include, for example, an alkyl optionally substituted with hydroxyl, and the "optionally substituted aminosulfonyl" may optionally have the same or different 1 to 2 substituent(s).

The substituents of "optionally substituted aryl" and "optionally substituted heterocyclic group" in $R^2$ include, for example:
(1) an optionally substituted alkyl,
(2) an optionally substituted alkoxy,
(3) a halogen,
(4) a heterocyclic group, or
(5) an amino optionally mono- or di-substituted with an alkyl
(6) hydroxyl, etc.,
and they may optionally have the same or different 1 to 3 substituent(s).

The substituents of "optionally substituted alkyl" in the above substituents of $R^2$ include, for example, (A) a halogen, (B) an alkoxycarbonyl, etc., and the "optionally substituted alkyl" may optionally have the same or different 1 or 2 group(s). The substituents of "optionally substituted alkoxy" in the above substituents of $R^2$ include, for example, 1 to 3 halogen(s), etc.

A preferable $R^2$ is an optionally substituted aryl, particularly optionally substituted phenyl. When $R^2$ is a substituted phenyl, at least one substituent is preferably substituted in meta position. The substituent is preferably an optionally substituted alkoxy, more preferably a C1 to C4 alkoxy, particularly preferably methoxy.

"Heterocyclic group", and the heterocyclic group of "heterocyclic group-substituted carbonyl" and "heterocyclic group-substituted carbonyloxy" in substituents of $R^1$ preferably includes a 4- to 7-membered monocyclic heterocyclic group, specifically morpholinyl, thiomorpholinyl, pyrrolidinyl, piperazinyl, piperidyl, homopiperazinyl, hexahydroazepinyl, hexahydrooxazepinyl, azetidinyl, pyridyl, pyrimidyl, thiazole, pyrazole, tetrahydropyrane, etc.

"Heterocyclic group" of substituents in "optionally substituted amino" and "optionally substituted carbamoyloxy", and the heterocyclic group of "heterocyclic group-substituted sulfonyl" and "heterocyclic group-substituted carbonyl" in the substituents of $R^1$ preferably includes the above heterocyclic group.

"Heterocyclic group" of $R^2$ preferably includes a 4- to 7-membered monocyclic heterocyclic group or a condensed group of the heterocyclic group with benzene ring, specifically pyridyl, pyrimidyl, indolyl, quinolyl, 2,3-dihydroindolyl, 1,2,3,4-tetrahydroquinolyl, etc.

"Heterocyclic group" of substituents in $R^2$ preferably includes a 4- to 7-membered monocyclic heterocyclic group, specifically pyrrolidine, piperidine, piperazine, homopiperazine, morpholine, thiomorpholine, etc.

When $R^4$ is a halogen, a preferable one is fluorine, and it is particularly preferable that $R^4$ is fluorine and $R^3$ is hydrogen.

A preferable $R^5$ is particularly hydrogen.

The pharmaceutically acceptable salt of the compound of the present invention includes, for example, an inorganic acid salt such as hydrochloride, sulfate, phosphate, hydrobromide, or an organic acid salt such as acetate, fumarate, oxalate, citrate, methanesulfonate, benzenesulfonate, tosylate, maleate, etc. When the compound of the present invention has an acidic group such as carboxy, the salt with a base (e.g., an alkali metal salt such as sodium salt, potassium salt, an alkaline earth metal salt such as calcium salt, an organic base salt such as triethylamine salt, an amino acid salt such as lysine salt) are also included therein.

The compound of the present invention or a pharmaceutically acceptable salt thereof includes both an intramolecular salt thereof and a solvate thereof such as a hydrate thereof.

The compound (1) of the present invention may exist in optically active isomers based on its asymmetric carbon, and includes any of forms of its isomers and a mixture thereof. Furthermore, when the compound (1) of the present invention has a double bond or a cycloalkanediyl, the compound may exist in cis- or trans-configuration, and the compound may exist in tautomers based on unsaturated bonds such as carbonyl. The compound (1) of the present invention also includes any isomers and a mixture thereof.

The compound (1) of the present invention may be prepared according to the following Methods. The following Methods are illustrated by using Compound (1-a) unless otherwise specified, and Compound (1) may be prepared by using the corresponding starting compound.

Method 1: Compound (1-a) may be prepared according to the following method:

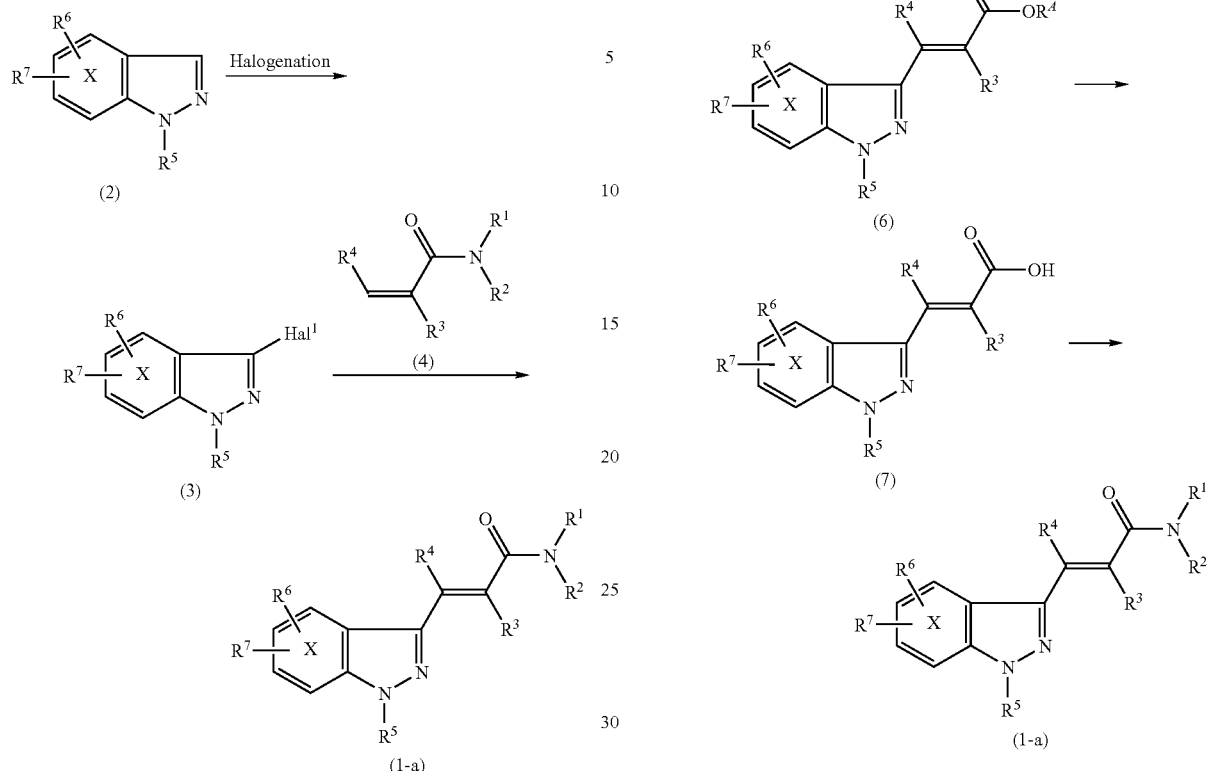

wherein Hal$^1$ is a halogen such as bromine, iodine, and the other symbols have the same meanings as defined above.

Compound (3) is prepared according to the method, for example, described in Tetrahedron 55 (1999) 6917-6922. Namely, Compound (2) is reacted with a halogen (e.g., bromine, iodine) in a solvent (e.g., DMF, DMSO) in the presence of an alkali (e.g., potassium hydroxide, sodium hydroxide, potassium carbonate, sodium carbonate, potassium bicarbonate, sodium bicarbonate) or an organic base (e.g., triethylamine, diisopropylethylamine) under ice cooling to room temperature for 30 minutes to 5 hours to give Compound (3).

Compound (1-a) is prepared according to the method, for example, described in Tetrahedron Lett. 41 (2000) 4363-4366 and Journal of the American Chemical Society, 1968, 90, 5518-5526. Namely, Compound (3) is reacted with Compound (4) in a solvent (e.g., DMF, DMSO, dioxane, THF, diethyl ether, acetonitrile, methanol, ethanol, acetone, isopropanol) in the presence of a catalyst (e.g., palladium acetate-triphenylphosphine, dichloro[1,1'-bis(diphenylphosphino) ferrocene]palladium (II)) and a base (e.g., triethylamine, tetrabutylammonium iodide) to give Compound (1-a).

Method 2: Compound (1-a) may be also prepared according to the following method:

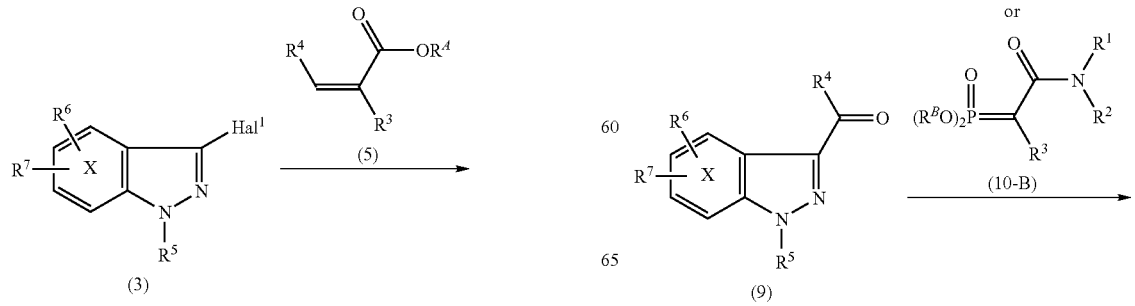

wherein R$^A$ is an alkyl, and the other symbols have the same meanings as defined above.

The reaction of Compound (3) and Compound (5) may be carried out in the similar manner to Method 1.

Compound (6) is treated with an aqueous solution of an acid (e.g., hydrochloric acid, sulfuric acid) or a base (e.g., sodium hydroxide, potassium hydroxide) in a solvent (e.g., methanol, ethanol, isopropanol, dioxane, THF, diethyl ether) or without solvent to give Compound (7).

Compound (7) is treated with a halogenating agent (e.g., N-bromosuccinimide, N-chlorosuccinimide) and triphenylphosphine and a base (e.g., triethylamine, diisopropylethylamine, N,N-dimethylaniline) in a solvent (e.g., dioxane, THF, diethyl ether), and then reacted with Compound (8) under the same temperature for 1 to 12 hours to give Compound (1-a).

Method 3: Compound (1-a) may be also prepared according to the following method:

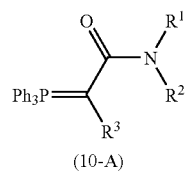

(10-A)

or

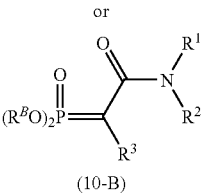

(10-B)

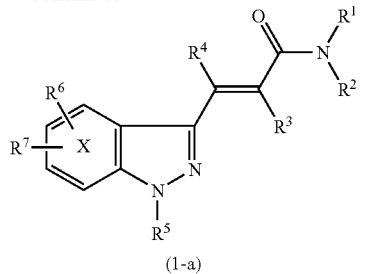

(1-a)

wherein $R^B$ is an alkyl or an aryl, and the other symbols have the same meanings as defined above.

Compound (9) is reacted with Compound (10-A) in a solvent (e.g., dioxane, THF, diethyl ether) at room temperature to refluxing temperature for 1 to 12 hours to give Compound (1-a).

Compound (9) is also reacted with Compound (10-B) in a solvent (e.g., dioxane, THF, diethyl ether) in the presence of a base (e.g., sodium hydride, lithium diisopropylamide, n-butyl lithium) at room temperature to refluxing temperature for 1 to 12 hours to give Compound (1-a).

Method 4: Compound (6) may be also prepared according to the following method:

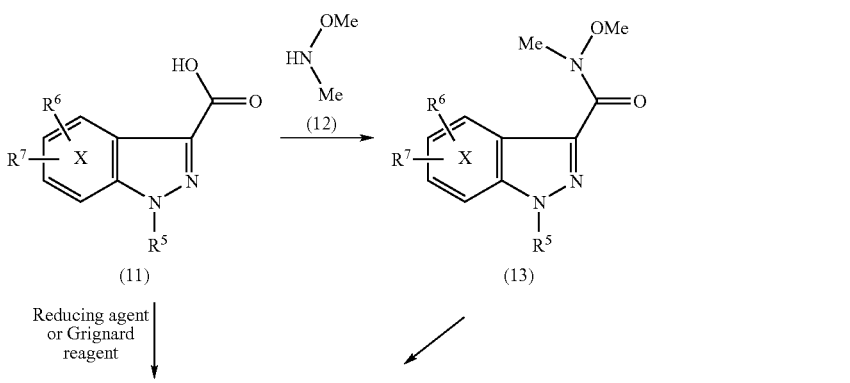

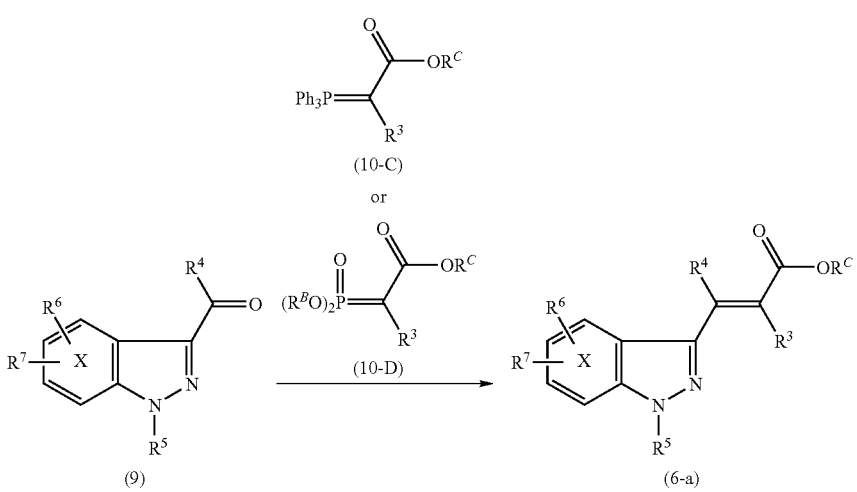

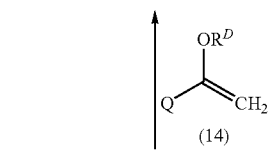

(14)

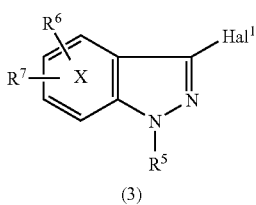

(3)

wherein $R^B$ is an alkyl or an aryl, $R^C$ and $R^D$ are each an alkyl, Q is hydrogen, $-B(OH)_2$, $-B(OR^E)(OR^D)$ or $-Sn(R^G)_3$, $R^E$ and $R^D$ are each an alkyl, or $R^E$ and $R^D$ combine together to form a straight or branched chain alkylene, $R^G$ is an alkyl, and the other symbols have the same meanings as defined above.

Compound (9) is prepared according to the following methods (1) to (3).

(1) Compound (3) is reacted with Compound (14) in a solvent (e.g., DME, THF, 1,4-dioxane, DMF, DMA, toluene, benzene, water or a mixture thereof) in the presence of a palladium catalyst (e.g., tetrakis(triphenylphosphine)palladium (0), bis(triphenylphosphine)palladium (II) chloride, palladium (II) acetate) at room temperature to refluxing temperature for 1 hour to 3 days, and then treated with an acid (e.g., hydrochloric acid, sulfuric acid) to give Compound (9) wherein $R^4$ is methyl.

When Compound (14) wherein Q is $-B(OH)_2$ or $-B(OR^E)(OR^D)$ is used, a base may be preferably added. The base may include, for example, an inorganic base such as an alkali metal carbonate, an alkali metal hydroxide, an alkali metal phosphate, an alkali metal fluoride and an organic base such as triethylamine.

When Compound (14) wherein Q is hydrogen is used, a ligand and a salt or a base may be preferably added. The ligand may include, for example, 1,3-bis(diphenylphosphino)propane, 1,1'-bis(diphenylphosphino)ferrocene, methyl diphenylphosphine, and the salt or the base may include, for example, a metal salt such as silver nitrate, thallium acetate and an organic base such as triethylamine.

(2) Compound (11), or Compound (13), which is obtained by condensing Compound (11) with Compound (12) by using a condensing agent (e.g., DCC, WSC), etc. in a conventional manner, is reduced with a reducing agent (e.g., lithium aluminum hydride, sodium borohydride) in a solvent (e.g., dioxane, THF, diethyl ether) at 0 to 100° C. for 1 to 24 hours to give Compound (9) wherein $R^4$ is hydrogen.

(3) Compound (13) is reacted with $R^4MgHal$, wherein each symbol has the same meaning as defined above, in a solvent (e.g., dioxane, THF, diethyl ether) at ice cooling to room temperature for 1 to 12 hours to give Compound (9) wherein $R^4$ is an alkyl.

The reaction of Compound (9) and Compound (10-C) or Compound (10-D) may be carried out in the similar manner to Method 3.

Method 5: Compound (7) wherein $R^4$ is an alkyl and $R^3$ is hydrogen may be also prepared according to the following method:

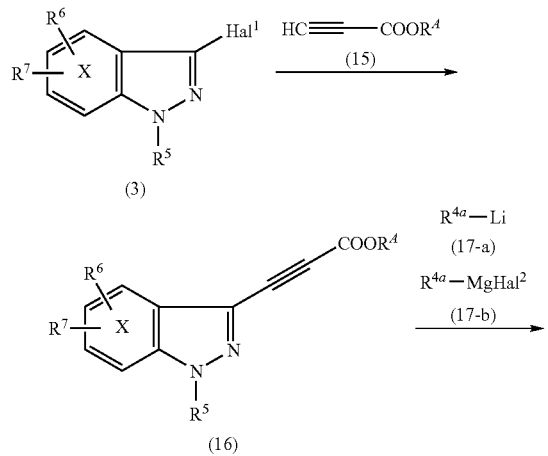

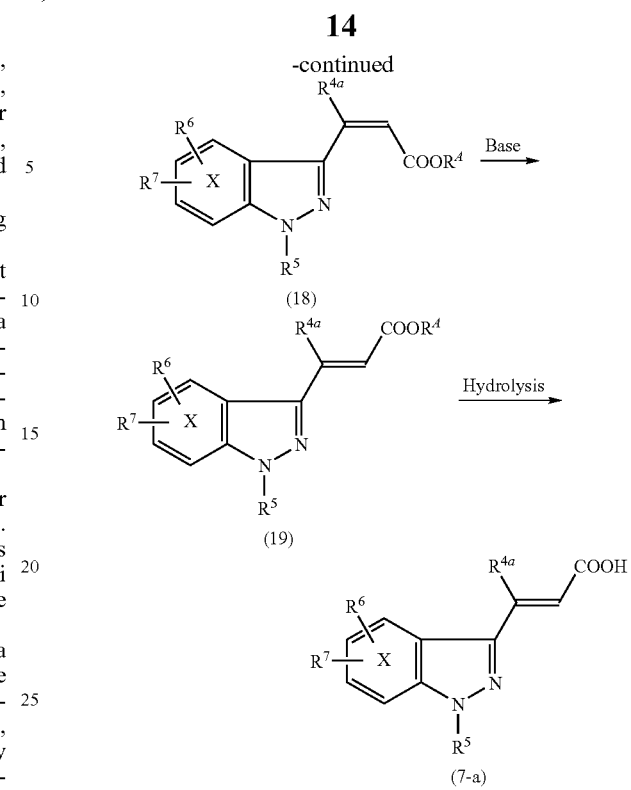

wherein $R^{4a}$ is an alkyl, $Hal^2$ is chlorine or bromine, and the other symbols have the same meanings as defined above.

Compound (3) and Compound (15) are treated with a palladium catalyst (e.g., dichlorobistriphenylphosphine palladium, tetrakistriphenylphosphine palladium, palladium acetate, trisdibenzylideneacetone dipalladium) in a solvent (e.g., DMSO, DMF, THF, 1,4-dioxane, diethyl ether, acetonitrile, toluene) in the presence of copper (I) iodide and a base (e.g., sodium bicarbonate, potassium bicarbonate, sodium hydroxide, potassium hydroxide, triethylamine, diisopropylethylamine) at 0° C. to 100° C. for 1 to 24 hours to give Compound (16).

Compound (16) is reacted with Compound (17-a) or Compound (17-b) in the presence of a cuprous salt (e.g., copper (I) iodide, copper (I) bromide, copper (I) cyanide) in a solvent (e.g., THF, 1,4-dioxane, diethyl ether, benzene, toluene, xylene, cyclohexane) at −78° C. to room temperature for 1 to 24 hours to give Compound (18).

Compound (18) is treated with a base (e.g., sodium methoxide, sodium ethoxide, DBU) in a solvent (e.g., methanol, ethanol, THF, 1,4-dioxane, diethyl ether, acetonitrile) at room temperature to refluxing temperature for 1 to 12 hours to give Compound (19).

A hydrolysis of Compound (19) may be carried out in the similar manner to Method 2.

Method 6: Compound (7) wherein $R^4$ is a halogen and $R^3$ is hydrogen may be prepared according to the following method:

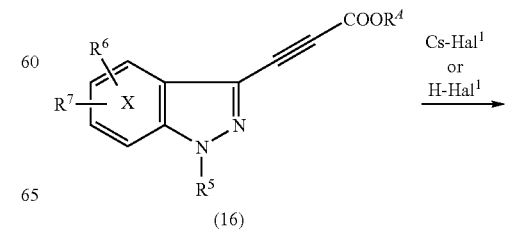

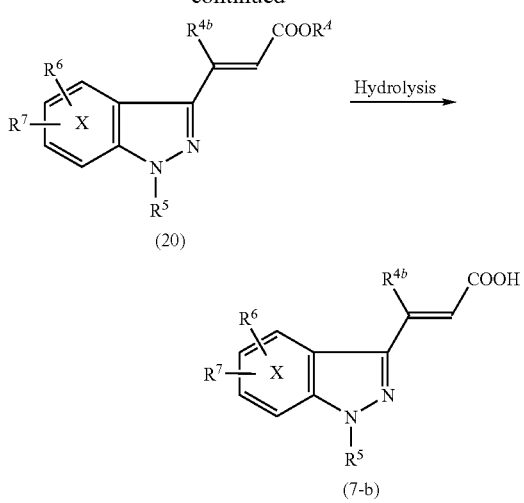

wherein $R^{4b}$ is a halogen, and the other symbols have the same meanings as defined above.

Compound (16) is treated with a cesium halide or a hydrogen halide in a solvent (e.g., DMSO, DMF) at room temperature to refluxing temperature for 1 to 48 hours to give Compound (20).

The present reaction may be carried out in the presence of a base (e.g., potassium hydrogen fluoride, sodium hydrogen fluoride) and water as necessary.

A hydrolysis of Compound (20) may be carried out in the similar manner to Method 2.

Method 7:

In Method 1, in place of Compound (4), the following Compound (4'):

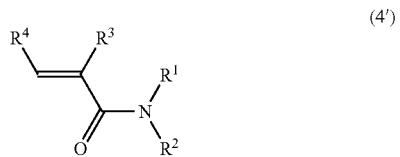

may be used to give Compound (1-b):

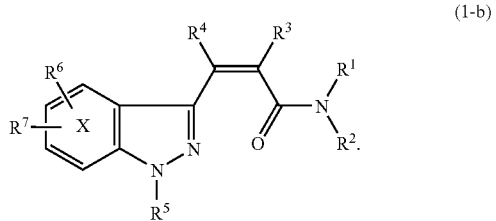

Compound (1-b) may be also prepared by reacting and treating in the similar manner to Method 2 or 3 using the corresponding starting compound as described above.

Method 8: Compound (2) wherein $R^5$ is hydrogen and a group of formula:

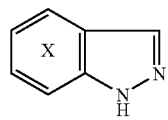

is a group of formula:

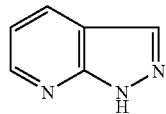

may be prepared according to the following method:

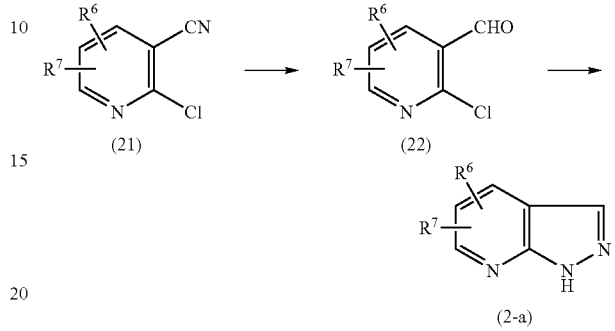

wherein each symbol has the same meaning as defined above.

Compound (22) is prepared according to the method described in Chem. Pharm. Bull., 50(8), 1066 (2002). Namely, Compound (21) is reduced by a reducing agent (e.g., diisobutylaluminum hydride, sodium triacetoxyborohydride, sodium cyanoborohydride, lithium aluminum hydride, sodium borohydride) in a solvent (e.g., benzene, toluene, xylene) at −78° C. to room temperature for 1 to 24 hours to give Compound (22).

Compound (2-a) is prepared according to the method described in Chemical Communications 293-294 (1966). Namely, Compound (22) is reacted with hydrazine or a hydrate thereof in a solvent (e.g., methanol, ethanol, isopropanol), if needed, in the presence of a catalyst (e.g., p-toluenesulfonic acid) at room temperature to heating temperature for 1 to 48 hours to give Compound (2-a).

Method 9: In the above methods, when the compound of the present invention, an intermediate thereof or a starting compound has a functional group (e.g., hydroxyl, amino, carboxy), it may be protected by a conventional protective group in an organic synthetic chemistry according to the method described in Theodora W. Greene, Peter G. M. Wuts, "Protective Groups in Organic Synthesis" 3rd. ed., John Wiley & Sons, Inc., 1999, and then the reaction is carried out, is followed by removal of the protective group to give the objective compound. The protective group includes a conventional protective group used in an organic synthetic chemistry described in said literature. Specifically, a protective group of hydroxyl includes, for example, tetrahydropyranyl, trimethylsilyl, t-butyldimethylsilyl, benzyl, 4-methoxybenzyl, methoxymethyl, acetyl and so on, that of amino includes, for example, t-butoxycarbonyl, benzyloxycarbonyl, 9-fluorenylmethoxycarbonyl, 2,2,2-trichloroethoxycarbonyl, t-amyloxycarbonyl, 4-methoxybenzyl, 2-nitrobenzenesulfonyl, 2,4-dinitrobenzenesulfonyl and so on, and that of carboxy includes, for example, an alkyl such as methyl, ethyl, t-butyl and benzyl.

The compound of the present invention or an intermediate thereof is prepared according to the above methods, and then a functional group therein may be converted or modified in a conventional manner. Specifically, the following methods are included.

(1) Conversion of an Amino into an Amide

An amino can be converted into the corresponding amide by reacting an amino with an acyl halide or reacting a carboxy with an amine in the presence of a condensing agent.

(2) Conversion of a Carboxy or an Ester Thereof into a Carbamoyl

A carboxy can be converted into the corresponding carbamoyl by converting a carboxy or a salt thereof into an acyl halide and then reacting it with an amine, by reacting a carboxy or a salt thereof with an amine in the presence of a condensing agent, or by reacting an ester thereof with an amine.

(3) Hydrolysis of an Ester

An ester can be converted into the corresponding carboxy or a salt thereof by hydrolyzing an ester with an alkali hydroxide (e.g., sodium hydroxide, potassium hydroxide) or an acid (e.g., hydrochloric acid, sulfuric acid), or by hydrogenating an ester with a metal catalyst.

(4) N-Alkylation and N-phenylation

An amino can be converted into the corresponding mono- or di-alkyl-substituted amino or phenyl-substituted amino by reacting an amino with an alkyl halide or a phenyl halide. An amino can be converted into the corresponding mono- or di-alkyl-substituted amino by reductive amination.

(5) N-Sulfonylation

An amino can be converted into the corresponding alkyl sulfonylamino or phenyl sulfonylamino by reacting an amino with an alkyl sulfonyl halide or a phenyl sulfonyl halide.

(6) Conversion of an Amino into an Ureido

An amino can be converted into the alkyl ureido by reacting an amino with an alkyl isocyanate or a carbamoyl halide. An amino can be also converted into the ureido by converting an amino into an isocyanate, a carbamoyl halide or a carbamate and then reacting them with an amine.

(7) Conversion of an Amino into a Carbamate

An amino can be converted into the carbamate by reacting an amino with an alkyl halocarbonate (e.g., methyl chlorocarbonate, ethyl chlorocarbonate) or converting an amino into an isocyanate and then reacting it with an alcohol.

(8) Conversion of an amino into 3-aminopropionyl or 2-aminoethylsulfonyl

An amino can be converted into the corresponding 3-aminopropionyl or 2-aminoethylsulfonyl by being subjected to Michael reaction with a 2,3-unsaturated carbonyl compound or a vinyl sulfonyl compound.

(9) Conversion of an Aromatic Nitro into an Aromatic Amine

An aromatic nitro can be converted into the aromatic amine by treating an aromatic nitro with a reducing agent [e.g., a metal reducing agent such as sodium borohydride, lithium borohydride, lithium aluminum hydride, a reduction by a metal (e.g., iron, zinc, tin, tin (II) chloride, titanium, titanium trichloride), a catalytic reduction with a transition metal (e.g., palladium-carbon, platinum, Raney nickel)] in a conventional manner. In the catalytic reduction, ammonium formate, hydrazine and so on, may be also used as a hydrogen source.

The compound of the present invention and each intermediate which are prepared in the above methods may be purified by a conventional method, for example, chromatography, recrystallization, etc. The solvent for recrystallization includes, for example, an alcohol solvent such as methanol, ethanol or 2-propanol, an ether solvent such as diethyl ether, diisopropyl ether or THF, an ester solvent such as ethyl acetate, an aromatic solvent such as toluene, a ketone solvent such as acetone, a hydrocarbon solvent such as hexane, water, or a mixed solvent thereof. The compound of the present invention may be converted into a pharmaceutically acceptable salt thereof in a conventional manner, and thereafter may be subjected to recrystallization.

Effect of Invention

The compound of the present invention or a pharmaceutically acceptable salt thereof has an $I_{Kur}$ blocking activity, and is useful for preventing or treating cardiac arrhythmia such as atrial fibrillation, atrial flutter, atrial arrhythmia, supraventricular tachycardia in a mammal. The compound of the present invention or a pharmaceutically acceptable salt thereof is also useful for preventing thromboembolism including apoplexy, heart failure including congestive heart failure.

The compound of the present invention or a pharmaceutically acceptable salt thereof may be formulated into a pharmaceutical composition comprising a therapeutically effective amount of said compound and a pharmaceutically acceptable carrier. The pharmaceutically acceptable carrier may include a diluent, a binder (e.g., syrup, gum arabic, gelatine, sorbit, tragacanth, polyvinylpyrrolidone), an excipient (e.g., lactose, sucrose, cornstarch, potassium phosphate, sorbit, glycine), a lubricant (e.g., magnesium stearate, talc, polyethyleneglycol, silica), a disintegrant (e.g., potato starch) and a wetting agent (e.g., sodium lauryl sulfate), etc.

The compound of the present invention or a pharmaceutically acceptable salt thereof may be administered orally or parenterally, and used as an appropriate pharmaceutical formulation. The appropriate pharmaceutical formulation for an oral administration includes, for example, a solid formulation such as a tablet, a granule, a capsule, a powder, or a liquid formulation, a suspension or an emulsifier. The appropriate pharmaceutical formulation for a parenteral administration includes a suppository, an injectable solution or an intravenous fluid preparation using distilled water for injection, physiological saline or aqueous glucose solution, or an inhalation.

The dose of the compound of the present invention or a pharmaceutically acceptable salt thereof varies depending on an administration route, age, body weight or conditions of a patient, but is usually about 0.003 to 100 mg/kg, preferably about 0.01 to 30 mg/kg, particularly about 0.05 to 10 mg/kg, per day.

BEST MODE FOR CARRYING OUT THE INVENTION

The present invention is further specifically illustrated by Examples and Reference Examples as below, but it is not limited thereto.

EXAMPLES

Example 1-1

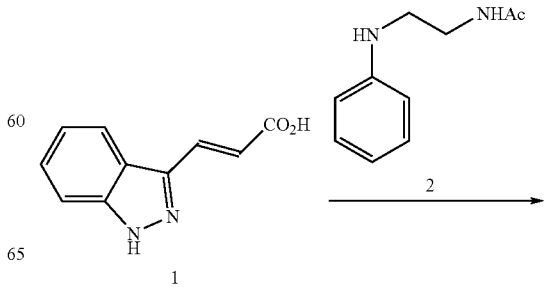

19

-continued

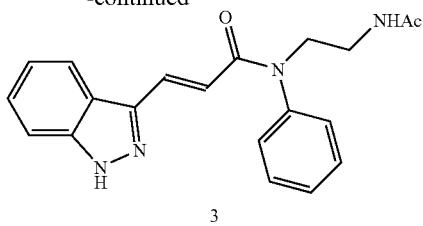

3

Compound 1 (200 mg) was suspended in anhydrous THF (7 ml), and thereto was added triphenylphosphine (279 mg) with stirring, and to the mixture was slowly added N-chlorosuccinimide (156 mg) under ice cooling. To the mixture was added a solution of Compound 2 (345 mg) in THF (0.5 ml), and the mixture was allowed to warm up to room temperature and stirred for 3 hours. To the mixture was added 10% aqueous citric acid solution, and the mixture was extracted with chloroform, dried over anhydrous sodium sulfate, and then concentrated under reduced pressure. The residue was purified by silica gel column chromatography (eluent: 3% methanol-chloroform) to give Compound 3 (121 mg) as a pale yellow crystal.

MS (APCI): 349 [M+H]$^+$

Example 1-2

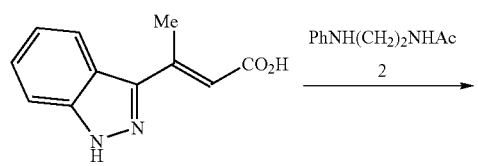

Compound 1 (270 mg) and triphenylphosphine (385 mg) were suspended in THF (6 ml), and thereto was added N-chlorosuccinimide (214 mg) under ice cooling and the mixture was stirred at room temperature for 1 minute. To the mixture was added a solution of Compound 2 (357 mg) and diisopropylethylamine (465 µl) in THF (5 ml) under ice cooling, and the mixture was stirred at room temperature for 2 hours. To the reaction mixture were added water and a saturated aqueous sodium bicarbonate solution, and the mixture was extracted with ethyl acetate. The extract layers were combined, washed with brine, dried over anhydrous sodium sulfate, and then concentrated under reduced pressure. The resulting residue was purified by silica gel chromatography (eluent: 3% to 10% methanol-chloroform gradient), concentrated under reduced pressure, and then the resulting mixture was crystallized from ethyl acetate-hexane (1:1) to give Compound 3.

MS (APCI) 363 [M+H]$^+$

20

Example 1-3

(1) Compound 1 (1.502 g) was dissolved in THF (70 ml), and thereto were sequentially added triphenylphosphine (2.510 g), then N-chlorosuccinimide (1.279 g) with stirring under ice cooling. The mixture was stirred for 60 minutes under ice cooling, and thereto was added dropwise a solution of Compound 2 (2.391 g) and diisopropylethylamine (2.777 ml) in THF (30 ml) over 30 minutes. After the addition, the mixture was allowed to warm up to room temperature and stirred for 25 hours. To the reaction mixture was added water with stirring under ice cooling, and the mixture was extracted with ethyl acetate. The extract layers were combined, washed with a saturated aqueous sodium bicarbonate solution and brine, and dried over anhydrous sodium sulfate. The solvent was distilled away under reduced pressure and the resulting residue was purified by silica gel column chromatography (eluent: 1 to 2% methanol-chloroform) to give Compound 3 (1.877 g) as a pale brown oil.

MS (APCI) 421 [M+H]$^+$

NMR (DMSO-d$_6$) ppm 1.27-1.35 (9H, m), 2.74-2.78 (3H, m), 3.44 (2H, m), 3.89 (2H, m), 6.58 (1H, m), 7.10 (1H, m), 7.3-7.6 (8H, m), 7.76 (1H, m), 13.41 (1H, br. s)

(2) Compound 3 (1.877 g) was suspended in ethyl acetate (10 ml), and thereto was added 4N hydrochloric acid-ethyl acetate solution (9 ml) with stirring under ice cooling. The reaction mixture was allowed to warm up to room temperature and stirred for 2 hours. To the reaction mixture was added isopropyl ether (10 ml), and the precipitated crystals were filtered, washed with ethyl acetate-isopropyl ether (1:1) mixture and dried under reduced pressure to give Compound 4 (1.654 g) as a pale yellow powder.
MS (APCI) 321 [M+H]$^+$
NMR (DMSO-d$_6$) ppm 2.62 (3H, t, J=5 Hz), 3.09 (2H, q, J=6 Hz), 4.08 (2H, t, J=6 Hz), 6.56 (1H, d, J=15.6 Hz), 7.11 (1H, t, J=7.5 Hz), 7.37 (2H, m), 7.45-7.62 (6H, m), 7.80 (1H, d, J=15.6 Hz), 8.62 (2H, m), 13.5 (1H, br. s)

(3) Compound 4 (130 mg) was suspended and stirred in chloroform (5 ml), and thereto was added triethylamine (152 μl). To the mixture was added dropwise a solution of methyl chloroformate (32 μl) in chloroform (2 ml) under ice cooling. The mixture was stirred at room temperature for 7.5 hours, and thereto was added water and the mixture was extracted with chloroform. The chloroform layers were combined, washed with brine, dried over anhydrous sodium sulfate, and then concentrated under reduced pressure. The residue was dissolved in methanol (5 ml), and thereto was added 28% sodium methoxide-methanol solution (7 μl). The mixture was stirred at room temperature for 10 minutes. The reaction mixture was concentrated under reduced pressure and purified by silica gel column chromatography (eluent: chloroform-methanol=9:1) to give Compound 5 (125.5 mg) as a colorless foam.
MS (APCI) 379 [M+H]$^+$
NMR (DMSO-d$_6$) ppm 2.79 (3H, s), 3.46 (2H, t, J=5.9 Hz), 3.51-3.54 (3H, m), 3.93 (2H, t, J=5.9 Hz), 6.58 (1H, m), 7.11 (1H, t, J=7.5 Hz), 7.3-7.6 (8H, m), 7.76 (1H, m), 13.4 (1H, br. s)

Example 1-4

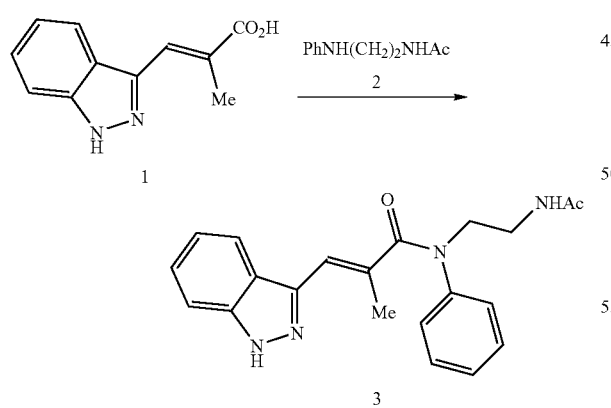

Compound 1 (150 mg) and triphenylphosphine (214 mg) were dissolved in THF (3.5 ml), and thereto was added N-chlorosuccinimide (119 mg) with stirring under ice cooling. The mixture was stirred at room temperature for 2 minutes. To the reaction mixture was added a solution of Compound 2 (198 mg) and diisopropylethylamine (258 μl) in THF (2.5 ml), and the mixture was stirred at room temperature for 2 hours. To the reaction mixture was added water, and the mixture was extracted with ethyl acetate. The extract layers were combined, washed with a saturated aqueous sodium bicarbonate solution and brine, dried over anhydrous sodium sulfate, and concentrated under reduced pressure. The resulting residue was purified by silica gel column chromatography (eluent: chloroform-2 to 9% methanol), and the resulting solid was triturated with ethyl acetate-hexane to give Compound 3 (176 mg).
MS (APCI) 363 [M+H]$^+$ Examples 1-5 to 2-59

The corresponding starting compounds were reacted and treated in the similar manner to the above Examples to give the compounds of Examples 1-5 to 2-59.

Example 3-1

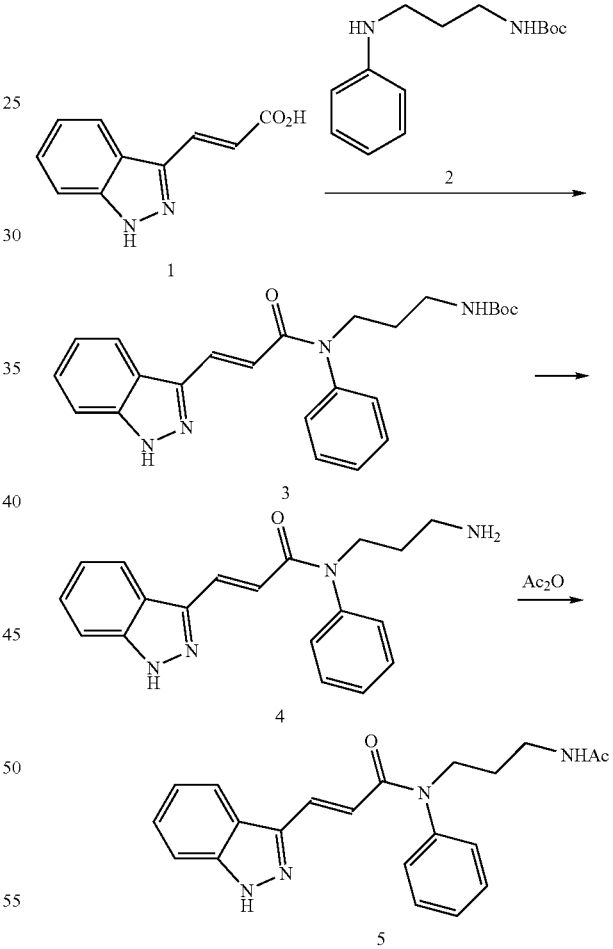

(1) Compound 1 (2.25 g) was dissolved in THF (80 ml), and thereto were sequentially added triphenylphosphine (3.78 g), then N-chlorosuccinimide (1.923 g) with stirring under ice cooling. The mixture was stirred for 60 minutes under ice cooling, and thereto was added dropwise a solution of Compound 2 (3.605 g) and diisopropylethylamine (4.18 ml) in THF (40 ml) over 10 minutes. After the addition, the mixture was allowed to warm up to room temperature and stirred for 18 hours. To the reaction mixture was added water with stirring under ice cooling, and the mixture was extracted with ethyl acetate. The extract layers were combined, washed with a saturated aqueous sodium bicarbonate solution and brine, and dried over anhydrous sodium sulfate. The solvent was distilled away under reduced pressure and the resulting residue was purified by NH-silica gel column chromatography (eluent: 50% ethyl acetate-hexane to 1% methanol-chloroform) to give Compound 3 (2.88 g) as a colorless solid.
MS (APCI) 421 [M+H]$^+$
IR (Nujor) 1709, 1651 cm$^{-1}$ (2) Compound 3 (2.88 g) was suspended in ethyl acetate (10.27 ml), and thereto was added dropwise 4N hydrochloric acid-ethyl acetate solution (17.13 ml) with stirring under ice cooling. The reaction mixture was allowed to warm up to room temperature and stirred overnight. The reaction mixture was ice-cooled, basified by the addition of 10% aqueous sodium hydroxide solution, and then extracted with chloroform. The extract layers were combined, washed with brine, dried over anhydrous sodium sulfate, and then the solvent was distilled away under reduced pressure to give Compound 4 (1.83 g).
MS (APCI) 321 [M+H]$^+$
IR (Nujor) 3349, 1651 cm$^{-1}$ (3) Compound 4 (160 mg) was suspended in pyridine (1.6 ml), and thereto was added THF-chloroform-DMF (2 ml-2 ml-2 ml). To the mixture was slowly added anhydrous acetic acid (0.05 ml), and the mixture was stirred at room temperature for 1.5 hours. To the reaction mixture was added water, and the mixture was extracted with ethyl acetate. The extract layer was washed with 0.5N hydrochloric acid solution, a saturated sodium bicarbonate water and brine, and dried over anhydrous sodium sulfate. The solvent was distilled away under reduced pressure and the resulting residue was purified by silica gel column chromatography (eluent: chloroform-5% methanol), and the resulting solid was triturated with ethyl acetate to give Compound 5 (127 mg) as a colorless powder.
MS (APCI) 363 [M+H]$^+$
IR (Nujor) 3272, 1650, 1618 cm$^{-1}$ Example 3-2

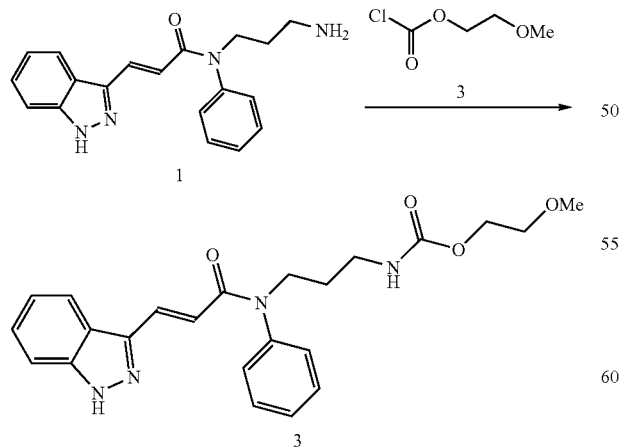

Compound 1 (120.5 mg) was suspended in chloroform (5 ml)-THF (3 ml), and thereto was added triethylamine (63 μl) with stirring under ice cooling. Then, thereto was added dropwise a solution of Compound 2 (45 μl) in chloroform (1 ml) over 15 minutes. The mixture was stirred at room temperature for 1 hour, and thereto was added water. The mixture was vigorously stirred, and then extracted with chloroform. The extract layers were combined, washed with brine, dried over anhydrous sodium sulfate, and then concentrated under reduced pressure. The resulting residue was purified by silica gel column chromatography (eluent: chloroform to chloroform-methanol 20:1) to give Compound 3 (145.0 mg) as a colorless powder.
MS (APCI) 423 [M+H]$^+$ Example 3-3

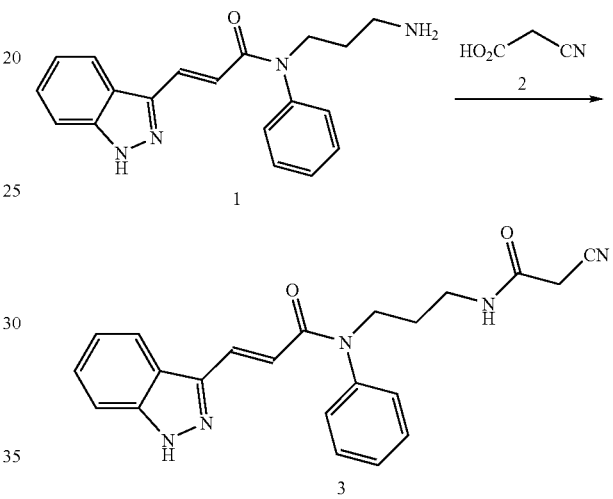

Compound 1 (120.2 mg) was suspended in DMF (5 ml), and thereto were added cyanoacetic acid (33.5 mg) and HOBt (66.1 mg), then added WSC (93.5 mg) with stirring under ice cooling. The mixture was allowed to warm up to room temperature and stirred for 1 hour. To the reaction mixture was added an aqueous sodium bicarbonate solution, and the mixture was extracted with ethyl acetate. The extract layers were combined, washed with brine, and dried over anhydrous sodium sulfate. The solvent was distilled away under reduced pressure, and the residue was purified by NH-silica gel column chromatography (eluent: chloroform-methanol 20:1) to give Compound 3 (113 mg) as a colorless powder.
MS (APCI) 388 [M+H]$^+$ Example 3-4

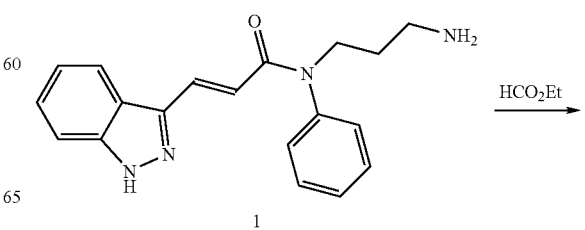

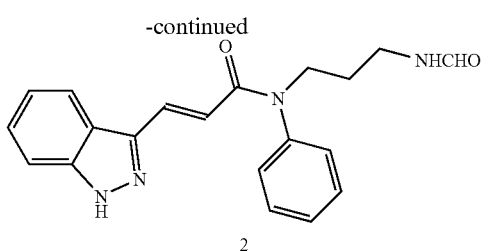

Compound 1 (120.0 mg) was suspended in DMF (2 ml), and thereto was added ethyl formate (3 ml). The mixture was stirred at room temperature for 3 days. To the reaction mixture was added ethyl acetate, and the mixture was washed with water several times, washed with brine, and then dried over anhydrous sodium sulfate. The solvent was distilled away under reduced pressure, and the residue was purified by silica gel column chromatography (eluent: chloroform to chloroform-methanol 9:1 gradient) to give Compound 2 (93.6 mg) as a colorless powder.

MS (APCI) 349 [M+H]$^+$

Example 3-5

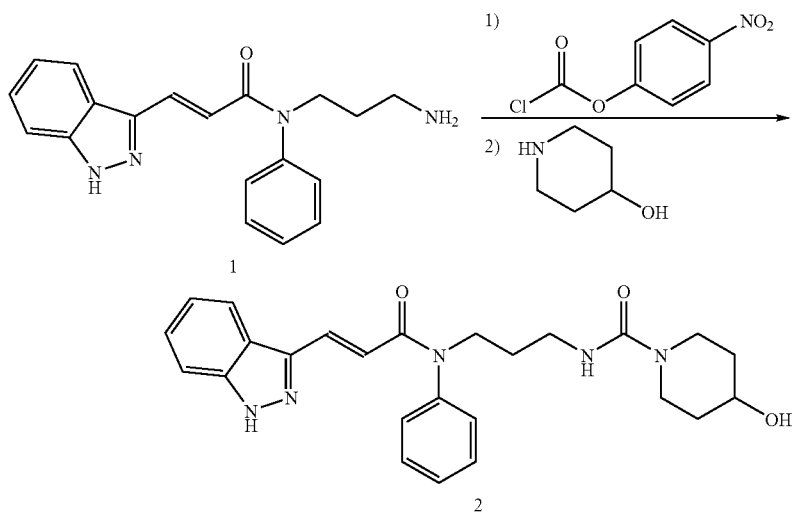

Compound 1 (110 mg) was suspended in chloroform (10 ml), and thereto was added triethylamine (53 nl), then added dropwise p-nitrophenyl chloroformate (73.0 mg) over 15 minutes with stirring under ice cooling. The mixture was stirred for 1.5 hours under ice cooling, and thereto were added 4-hydroxypiperidine (70 mg) and triethylamine (100 μl). The mixture was allowed to warm up to room temperature and stirred for 1 day. To the reaction mixture was added an aqueous sodium bicarbonate solution, and the mixture was extracted with chloroform. The extract layers were combined, washed with brine, dried over anhydrous sodium sulfate, and concentrated under reduced pressure. The residue was purified by NH-silica gel column chromatography (eluent: chloroform to chloroform-methanol 80:20 gradient) to give Compound 2 (87.1 mg) as a colorless amorphous powder.

MS (APCI) 448 [M+H]$^+$

NMR (DMSO-d$_6$) ppm 1.21 (2H, m), 1.61 (2H, q, J=7 Hz), 1.64 (2H, m), 2.85 (2H, m), 3.05 (2H, q, J=6.7 Hz), 3.58 (1H, m), 3.65 (2H, dt, 13.5, 14 Hz), 3.80 (2H, t, J=7.4 Hz), 4.65 (1H, d, J=4 Hz), 6.48 (1H, t, J=5.5 Hz), 6.55 (1H, d, J=15 Hz), 7.10 (1H, t, J=7 Hz), 7.3-7.6 (8H, m), 7.74 (1H, d, J=16 Hz), 13.4 (1H, brs)

Examples 3-6 and 3-7

The corresponding starting compounds were reacted and treated in the similar manner to the above Examples to give the compounds of Examples 3-6 and 3-7.

Example 4-1

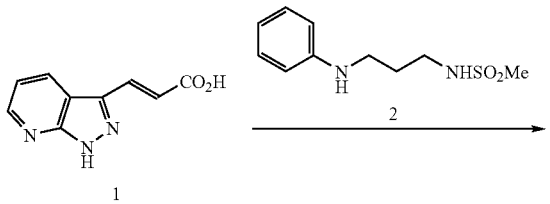

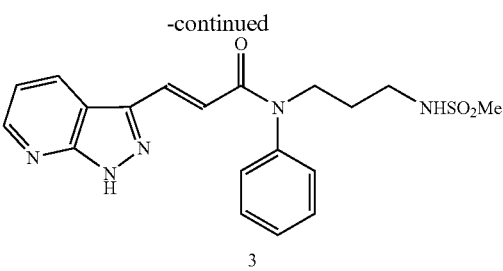

Compound 1 (5.0 g) is dissolved in THF (720 ml) under heating, and thereto were added triphenylphosphine (11.09 g) and N-chlorosuccinimide (5.27 g) with stirring at room temperature. The mixture was stirred for 5 minutes. Then, thereto was added a solution of Compound 2 (6.64 g) and N,N-dimethylaniline (7.37 ml) in THF (50 ml) with stirring at room temperature, and the mixture was stirred at room temperature for 1 hour. The reaction mixture was poured into water, and extracted with ethyl acetate. The extract layers were combined, washed with a saturated aqueous sodium bicarbonate solution and brine, dried over anhydrous magnesium sulfate, and then concentrated under reduced pressure. The residue was purified by silica gel column chromatography (eluent: chloroform-0% to 5% methanol gradient) to give Compound 3 (15.588 g) as a colorless crystalline powder.

MS (APCI) 400 [M+H]$^+$ (An Alternative Method)

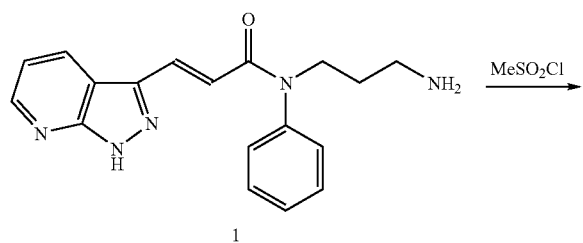

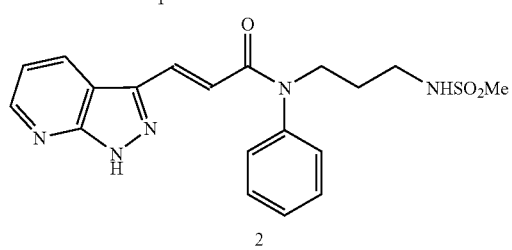

Compound 1 (630 mg) was dissolved in chloroform (50 ml)-THF (15 ml), and thereto was added triethylamine (641 µl) and added dropwise methane sulfonyl chloride (160 µl) with stirring under ice cooling. The mixture was stirred for 1 hour under ice cooling, and the reaction mixture was poured into water and extracted with chloroform. The extract layers were combined, washed with an aqueous sodium bicarbonate solution and brine, and then dried over anhydrous sodium sulfate. The solvent was distilled away under reduced pressure, and the residue was purified by silica gel column chromatography (eluent: chloroform-methanol 100:1 to 30:1). The solvent was distilled away, and the resulting residue was crystallized from ethyl acetate, and triturated with isopropyl ether to give Compound 2 (561 mg) as a colorless powder.

MS (APCI) 400 [M+H]$^+$

IR (Nujol) 1656 cm$^{-1}$

Examples 4-2 to 4-61

The corresponding starting compounds were reacted and treated in the similar manner to the above Examples to give the compounds of Examples 4-2 to 4-61.

Example 5-1

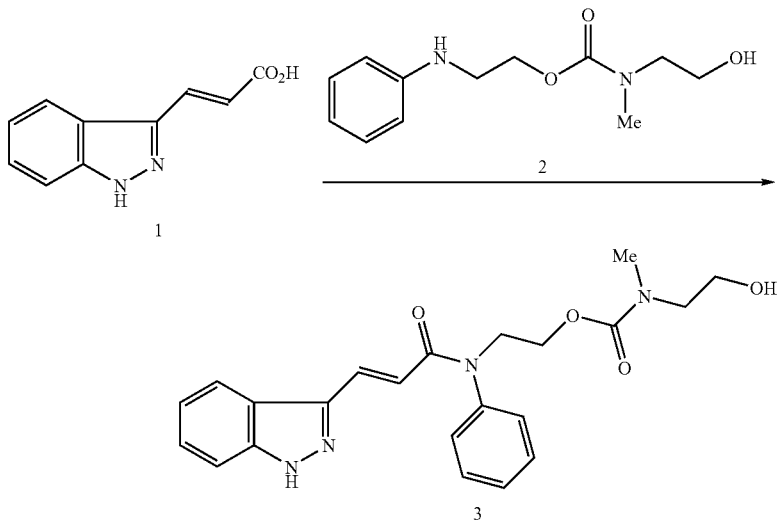

To a solution of Compound 1 (110 mg) and triphenylphosphine (184 mg) in THF (3 ml) was added N-chlorosuccinimide (101 mg) with stirring at room temperature, and the mixture was stirred for 1 minute under ice cooling. Then, thereto were added Compound 2 (167 mg) and N,N-dimethylaniline (148 nl), and the mixture was stirred at room temperature for 2 hours. To the reaction mixture was added an aqueous citric acid solution, and the mixture was extracted with ethyl acetate. The extract layers were combined, washed with brine, and dried over anhydrous sodium sulfate. The solvent was distilled away under reduced pressure, and the resulting residue was purified by silica gel column chromatography (eluent: chloroform-methanol 97:3 to 11:89 gradient) to give Compound 3 (196 mg) as a colorless amorphous powder.

MS (APCI) 409 [M+H]$^+$

Examples 5-2 to 5-35

The corresponding starting compounds were reacted and treated in the similar manner to the above Examples to give the compounds of Examples 5-2 to 5-35.

Example 6-1

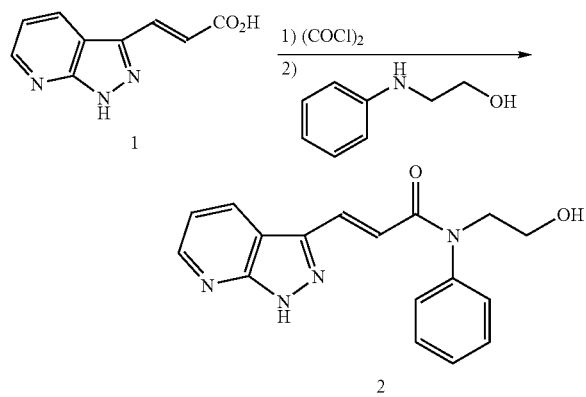

To a solution of Compound 1 (25 mg) in methylene chloride (3 ml) were added oxazalyl chloride (36 n1) and a drop of DMF, and then the mixture was refluxed for 1 hour under heating. The reaction solution was cooled, and then concentrated under reduced pressure. The residue was suspended in chloroform (3 ml), and thereto was added a solution of 2-anilinoethanol (51 μl) in chloroform (3 ml). The mixture was stirred at room temperature for 16 hours. To the reaction mixture was added an aqueous sodium bicarbonate solution, and the mixture was extracted with chloroform. The extract layers were combined, washed with brine, and dried over anhydrous sodium sulfate. The solvent was distilled away under reduced pressure, and the residue was purified by silica gel column chromatography (eluent: chloroform-1 to 8% methanol gradient) to give Compound 2 (11.5 mg) as a colorless powder.

MS (APCI) 309 [M+H]$^+$

Example 6-2

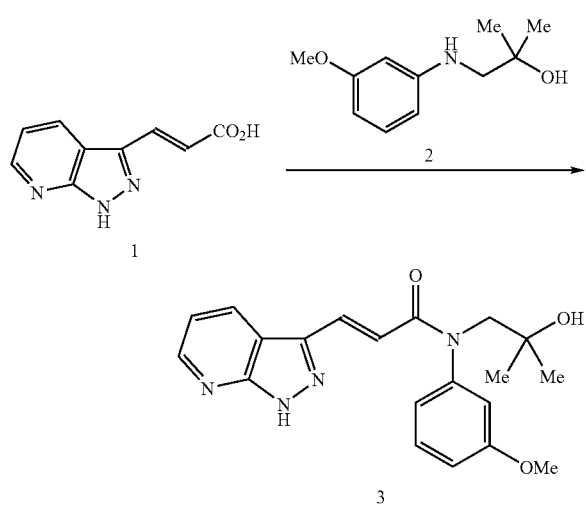

Compound 1 (12.4 g) was dissolved in THF (1860 ml) under heating, and thereto were added triphenylphosphine (27.5 g) and N-chlorosuccinimide (13.1 g) with stirring at room temperature. The mixture was stirred for 1 minute. Then, thereto was added a solution of Compound 2 (14.1 g) and N,N-dimethylaniline (16.6 ml) in THF (140 ml) with stirring at room temperature, and the mixture was stirred at room temperature for 3 hours. The reaction mixture was poured into a mixture of 2N aqueous sodium hydroxide solution (900 ml) and brine (900 ml), and extracted with ethyl acetate. The extract layers were combined, washed with brine, dried over anhydrous magnesium sulfate, and then concentrated under reduced pressure. To the residue was added ethyl acetate, and the precipitated crystals were filtered and recrystallized from ethanol to give Compound 3 (15.588 g) as a pale yellow crystalline powder.

MS (APCI) 367 [M+H]$^+$

IR (Nujol) 1651 cm$^{-1}$

Example 6-3

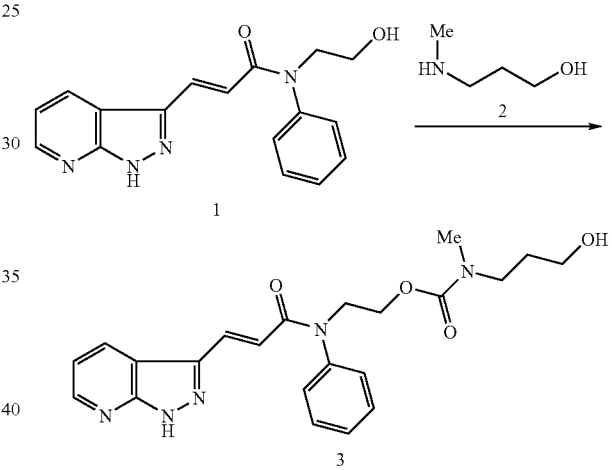

To Compound 1 (154 mg) were added acetonitrile (5 ml)-THF (5 ml), then N,N'-disuccinimidyl carbonate (323 mg) and N,N'-dimethylaminopyridine (6 mg), and the mixture was stirred at room temperature for 20 hours. Then, thereto was added Compound 2 (178 mg), and the mixture was stirred at room temperature for 24 hours. To the reaction mixture was added 5% aqueous potassium carbonate solution, and the mixture was extracted with ethyl acetate. The extract layers were combined, washed with brine, dried over anhydrous sodium sulfate, and then concentrated under reduced pressure. The resulting residue was dissolved in methanol (5 ml), and thereto were added water (2.5 ml) and potassium carbonate (346 mg) with stirring under ice cooling. The mixture was stirred at room temperature for 2.5 hours. To the reaction mixture was added water, and the mixture was extracted with ethyl acetate. The extract layers were combined, washed with brine, dried over anhydrous sodium sulfate, and then the solvent was distilled away under reduced pressure. The residue was purified by silica gel column chromatography (eluent: methanol-ethyl acetate 3:97 to 12:88 gradient) to give Compound 3 (91 mg) as a colorless oil.

MS (APCI) 424 [M+H]$^+$

Examples 6-4 to 7-5

The corresponding starting compounds were reacted and treated in the similar manner to the above Examples to give the compounds of Examples 6-4 to 7-5.

Example 8-1

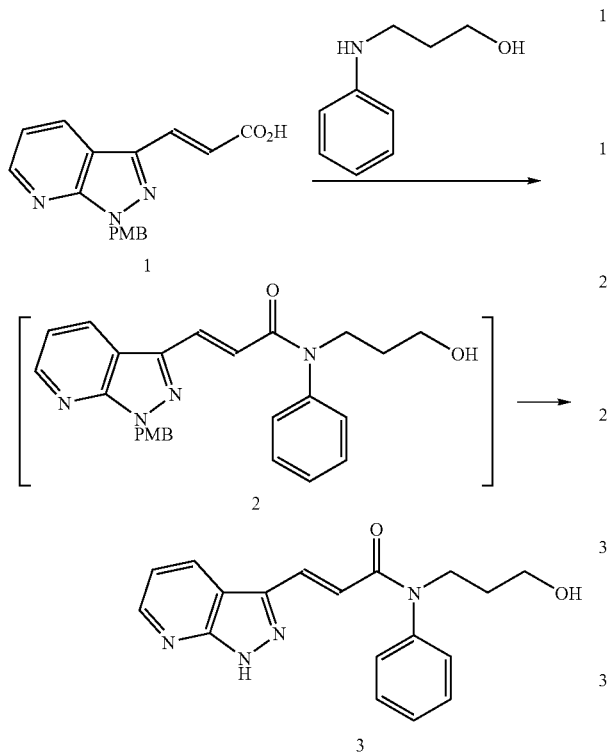

(1) Compound 1 (200 mg) was dissolved in THF (20 ml), and thereto was added triphenylphosphine (254 mg) with stirring at room temperature, then added N-chlorosuccinimide (147 mg). The mixture was stirred for 1 minute, and then thereto was added a solution of 3-anilinopropanol (108 mg) and diisopropylethylamine (225 µl) in THF (1 ml). The mixture was stirred at room temperature for 1.5 hours. To the reaction mixture was added an aqueous sodium bicarbonate solution, and the mixture was extracted with ethyl acetate. The extract layers were combined, washed with brine, dried over anhydrous sodium sulfate, and then the solvent was distilled away under reduced pressure. The residue was purified by silica gel column chromatography (ethyl acetate-chloroform 1:1) to give Compound 2 (143.6 mg) as a pale yellow powder.
MS (APCI) 443 [M+H]$^+$ (2) Compound 2 (136.3 mg) was suspended in trifluoroacetic acid (4.5 ml) and the mixture was refluxed for 4.5 hours under heating. The reaction solution was concentrated under reduced pressure, and to the residue was added an aqueous sodium bicarbonate solution, and the mixture was extracted with ethyl acetate. The extract layers were combined, washed with brine, and dried over anhydrous magnesium sulfate. The solvent was distilled away under reduced pressure, and the residue was purified by silica gel column chromatography (chloroform-methanol to 8% gradient) to give Compound 3 (35.8 mg) as a colorless powder.
MS (APCI) 323 [M+H]$^+$

Examples 8-2 to 8-39

The corresponding starting compounds were reacted and treated in the similar manner to the above Examples to give the compounds of Examples 8-2 to 8-39.

Example 9-1

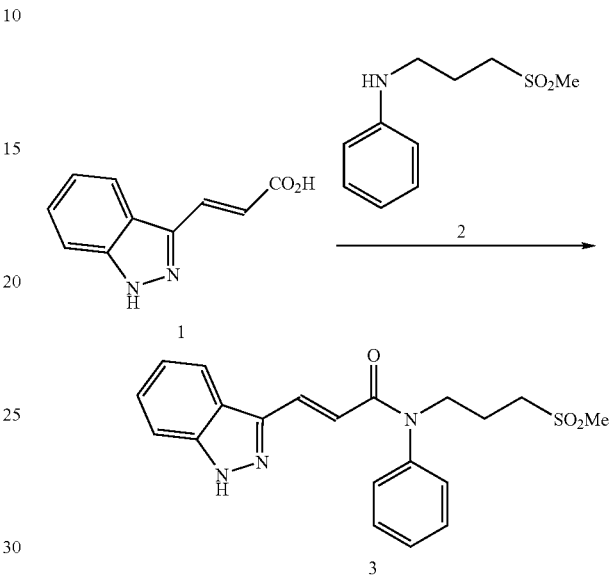

Compound 1 (200 mg) was suspended in anhydrous THF (7 ml), and thereto was added triphenylphosphine (307 mg), and then slowly added N-chlorosuccinimide (170 mg) with stirring under ice cooling. Then, thereto was added a solution of Compound 2 (408 mg) in THF (0.5 ml)-methylene chloride (1.5 ml), and the mixture was allowed to warm up to room temperature and stirred for 2 hours. Then, thereto was added 10% aqueous citric acid solution, and the mixture was extracted with chloroform. The extract was dried over anhydrous sodium sulfate, concentrated under reduced pressure, and then the residue was purified by silica gel column chromatography (chloroform-2% methanol) to give Compound 3 (338 mg) as a pale yellow oil.

MS (APCI): 384 [M+H]$^+$

Example 9-2

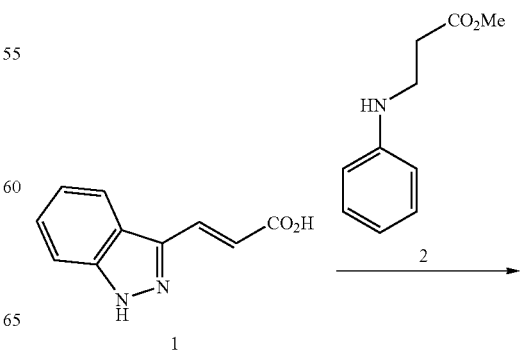

-continued

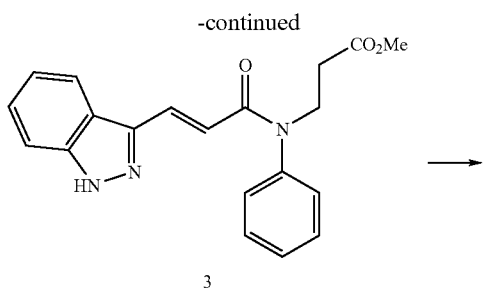

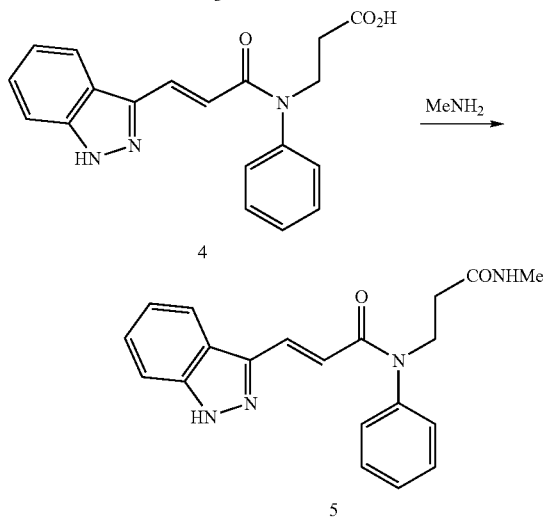

(1) To a solution of Compound 1 (400 mg) and triphenylphosphine (613 mg) in THF (17 ml) was added N-chlorosuccinimide (341 mg) with stirring at room temperature, and the mixture was stirred for 1 minute under ice cooling. Then, thereto was added 3-phenylaminopropionic acid methyl ester (686 mg) under ice cooling, and the mixture was stirred at room temperature for 4 hours. Then, thereto were added triphenylphosphine (112 mg) and N-chlorosuccinimide (57 mg) under ice cooling, and the mixture was stirred at room temperature for 1.5 hours. To the reaction mixture was added an aqueous citric acid solution, and the mixture was extracted with ethyl acetate. The extract layers were combined, washed with brine, and dried over anhydrous sodium sulfate. The solvent was distilled away under reduced pressure, and the resulting residue was purified by silica gel column chromatography (eluent: chloroform-methanol 40:1) to give Compound 3 (565 mg) as a colorless solid.
MS (APCI) 352 [M+H]$^+$ (2) Compound 3 (648 mg) was suspended in methanol (4.6 ml), and thereto were added THF (2.3 ml), then 2N aqueous sodium hydroxide solution (4.6 ml). The mixture was stirred at room temperature for 2 hours, and thereto was added 2N hydrochloric acid solution (4.6 ml) under ice cooling, and the mixture was extracted with ethyl acetate. The extract layers were combined, washed with brine, and dried over anhydrous sodium sulfate. The mixture was concentrated under reduced pressure, and the residue was triturated with isopropyl ether, filtered, and then dried to give Compound 4 (535 mg) as a colorless powder.
MS (ESI) 334 [M−H]$^−$ (3) Compound 4 (140 mg) and HOBt (73 mg) were dissolved in DMF (2 ml), and thereto were added 2N methylamine-THF solution (522 μl) and WSC (104 mg). The mixture was stirred at room temperature for 5 hours. Then, thereto was added an aqueous sodium bicarbonate solution, and the mixture was extracted with ethyl acetate. The extract layers were combined, washed with brine, and dried over anhydrous sodium sulfate. The solvent was distilled away under reduced pressure, and the residue was purified by silica gel column chromatography (eluent: chloroform-methanol 98:2 to gradient) to give Compound 5 (111 mg) as a colorless powder.
MS (APCI) 349 [M+H]$^+$ Example 9-3

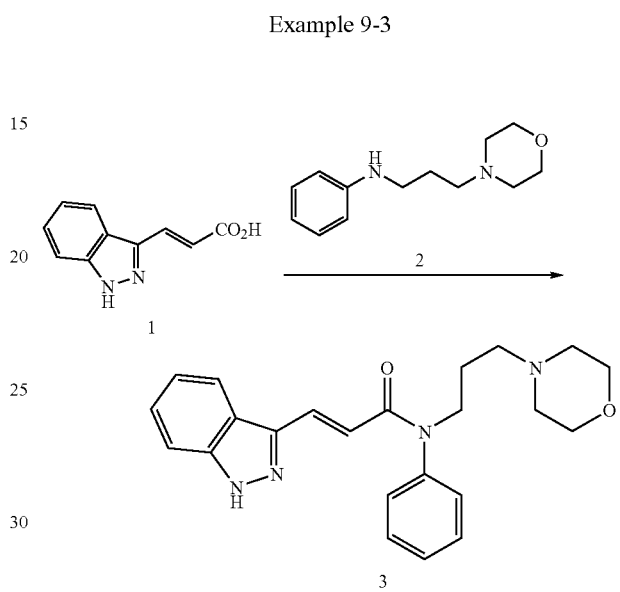

To a solution of Compound 1 (120 mg) and triphenylphosphine (184 mg) in THF (5 ml) was added N-chlorosuccinimide (102 mg) with stirring at room temperature, and the mixture was stirred at room temperature for 1 minute. Then, thereto were added Compound 2 (169 mg) and diisopropylethylamine (222 μl) with stirring at room temperature, and the mixture was stirred at room temperature for 2 hours. To the reaction mixture was added brine, and the mixture was extracted with ethyl acetate. The extract layers were combined, washed with brine, and dried over anhydrous sodium sulfate. The solvent was distilled away under reduced pressure, and the resulting residue was purified by silica gel column chromatography (eluent: chloroform-methanol 98:2) to give Compound 3 (195 mg) as a colorless foam.
MS (APCI) 391 [M+H]$^+$ Examples 9-4 to 10-32

The corresponding starting compounds were reacted and treated in the similar manner to the above Examples to give the compounds of Examples 9-4 to 10-32.

Example 11-1

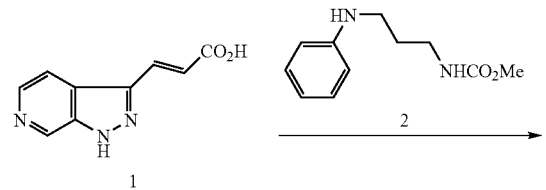

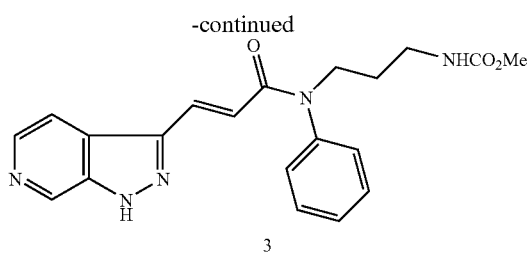

3

A suspension of Compound 1 (100 mg) in thionyl chloride (2.9 ml) was stirred at 60° C. for 1.5 hours under heating. After cooling, the suspension was concentrated under reduced pressure, and the resulting pale yellow solid was suspended in THF (4 ml) and chloroform (6 ml). Then, thereto were added dimethylaminopyridine (71 mg), then a solution of Compound 2 (363 mg) in THF (2 ml) under ice cooling, and the mixture was stirred at room temperature for 22 hours. To the reaction mixture were added water and a saturated aqueous sodium bicarbonate solution, then methanol-chloroform (1:5), and the mixture was vigorously stirred. An insoluble was filtered off through Celite and washed with methanol-chloroform (1:5) sufficiently. The filtrate and wash liquid were combined and separated, and the organic layer was dried over anhydrous sodium sulfate, and then concentrated under reduced pressure. The resulting residue was purified by silica gel chromatography (eluent: 1% to 6% methanol-chloroform gradient) to give Compound 3 (61 mg) as a colorless powder.

MS (APCI) 380 [M+H]$^+$

Example 12-1

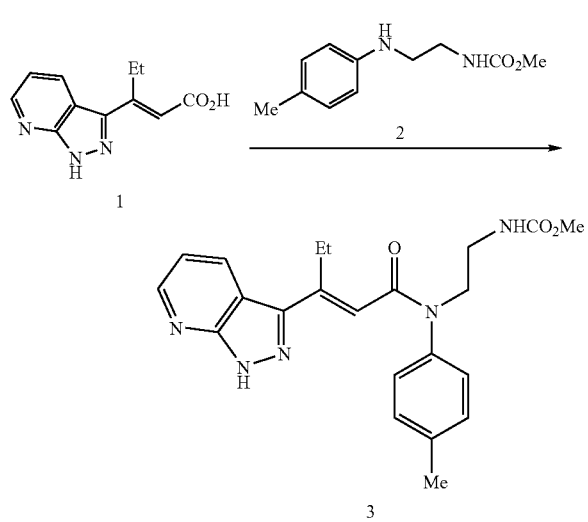

To a solution of Compound 1 (30 mg) and triphenylphosphine (51 mg) in THF (6 ml) was added N-chlorosuccinimide (24 mg) with stirring under ice cooling, and the mixture was stirred for 10 minutes under ice cooling. Then, thereto were added Compound 2 (43 mg) and N,N-dimethylaniline (42 mg) with stirring under ice cooling, and the mixture was stirred at room temperature for 20 hours. To the reaction mixture was added an aqueous sodium bicarbonate solution, and the mixture was extracted with ethyl acetate. The extract layer was washed with brine, and dried over anhydrous sodium sulfate. The solvent was distilled away under reduced pressure, and the resulting residue was purified by silica gel column chromatography (eluent: chloroform-methanol 98:2 to 92:8) to give Compound 3 (56 mg) as a colorless powder.

MS (APCI) 408 [M+H]$^+$

Example 12-2

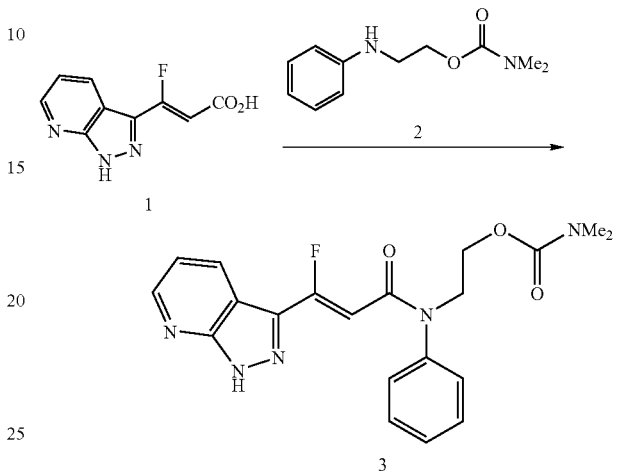

To a solution of Compound 1 (62 mg) and triphenylphosphine (126 mg) in THF (12 ml) was added N-chlorosuccinimide (60 mg) with stirring at room temperature, and the mixture was stirred at room temperature for 2 minutes. Then, thereto were added Compound 2 (75 mg) and N,N-dimethylaniline (76 μl) with stirring at room temperature, and the mixture was stirred at room temperature for 4 hours. To the reaction mixture was added brine, and the mixture was extracted with ethyl acetate. The extract layer was washed with an aqueous sodium bicarbonate solution, and dried over anhydrous sodium sulfate. The solvent was distilled away under reduced pressure, and the resulting residue was purified by silica gel column chromatography (eluent: chloroform-methanol 98:2 to 92:8) to give Compound 3 (79 mg) as a colorless powder.

MS (APCI) 398 [M+H]$^+$

Examples 12-3 to 12-13

The corresponding starting compounds were reacted and treated in the similar manner to the above Examples to give the compounds of Examples 12-3 to 12-13.

Example 13-1

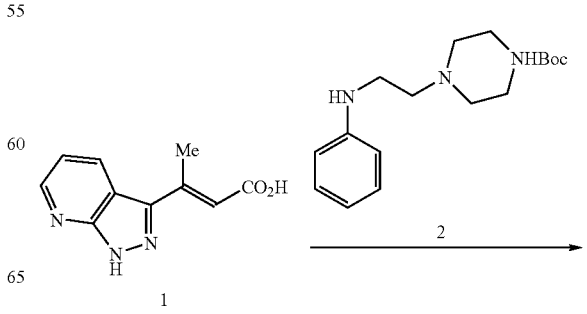

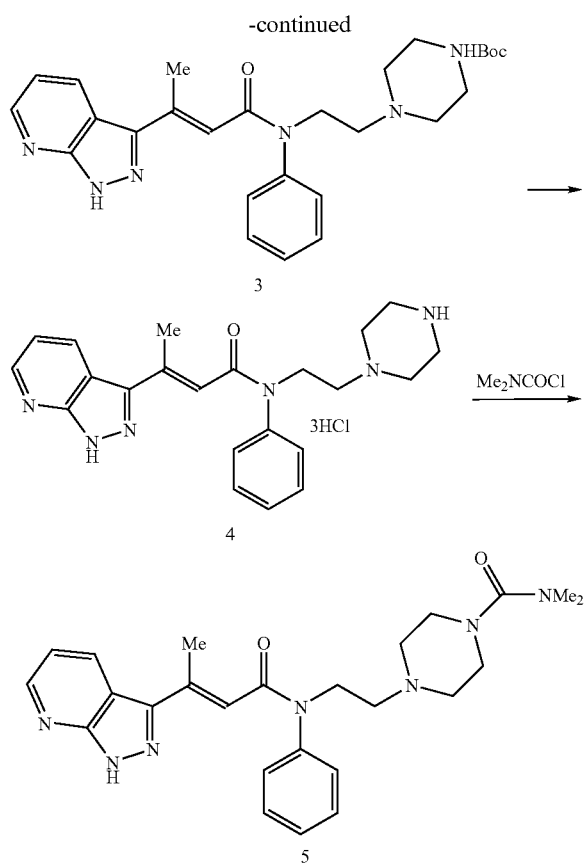

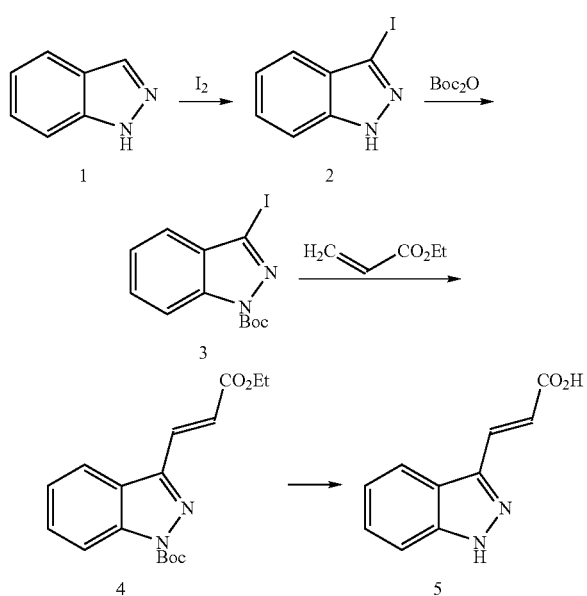

(1) Compound 1 (400 mg) and triphenylphosphine (723 mg) were dissolved in THF (58 ml), and thereto was added N-chlorosuccinimide (342 mg) with stirring under ice cooling. The mixture was stirred for 5 minutes under ice cooling, and thereto was added dropwise a solution of Compound 2 (720 mg) and N,N-dimethylaniline (596 mg) in THF (2 ml). After the addition, the mixture was stirred at 60° C. for 18 hours under heating. The reaction solution was cooled to room temperature, and the solvent was distilled away. To the residue was added a saturated aqueous sodium bicarbonate solution, and the mixture was extracted with ethyl acetate. The extract layer was washed with brine, and dried over anhydrous magnesium sulfate. The solvent was distilled away under reduced pressure, and the resulting residue was purified by silica gel column chromatography (eluent: methanol-chloroform 0:1 to 1:9) to give Compound 3 (1016 mg) as a pale yellow oil.
MS (APCI) 491 [M+H]$^+$ (2) Compound 3 (1016 mg) was dissolved in methylene chloride (10 ml), and thereto was added dropwise 4N hydrochloric acid-ethyl acetate solution (20 ml) with stirring at room temperature. To the reaction mixture was added ethanol (20 ml), and the mixture was stirred at 50° C. for 20 minutes under heating. The reaction solution was cooled to room temperature, and the solvent was distilled away. The residue was triturated with diethyl ether, filtered and dried to give Compound 4 (898 mg) as a pale yellow powder.
MS (APCI) 391 [M+H]$^+$ (3) Compound 4 (150 mg) was suspended in THF (4 ml), and thereto were sequentially added triethylamine (184 µl) and dimethylcarbamoyl chloride (34 mg) with stirring under ice cooling. The mixture was stirred at room temperature for 18 hours, and the solvent was distilled away. To the residue was added brine, and the mixture was extracted with ethyl acetate and dried over anhydrous magnesium sulfate. The solvent was distilled away under reduced pressure, and the resulting residue was purified by silica gel column chromatography (eluent: methanol-chloroform 0:1 to 1:9) to give Compound 5 (105 mg) as a colorless powder.
MS (APCI) 462 [M+H]$^+$ Examples 13-2 to 13-11

The corresponding starting compounds were reacted and treated in the similar manner to the above Examples to give the compounds of Examples 13-2 to 13-11.

Reference Example 1

(1) According to the method described in J. Prak. Chem. 1924, 297-320, Compound 1 (60.0 g) was dissolved in DMF (800 ml), and thereto were slowly added granular potassium hydroxide (114.08 g) and iodine (255.2 g) under ice cooling. The reaction mixture was stirred at room temperature for 1 hour and poured into an ice-cooled 10% aqueous sodium bisulfite solution (3 L). The precipitated white solid was filtered, washed with water, and dried to give Compound 2 (107.4 g) as a pale yellow crystal. Melting point 140.3 to 141.3° C.

The filtrate was extracted with diethyl ether, dried over sodium sulfate, and then diethyl ether was distilled away under reduced pressure. The resulting residue was recrystallized from ethyl acetate-hexane to give Compound 2 (4.939 g) as a pale yellow crystal.

(2) Compound 2 (100 g) and dimethylaminopyridine (2.5 g) were suspended in acetonitrile (1200 ml), and thereto was added triethylamine (115 ml), then di-tert-butyl dicarbonate (98.6 g) at room temperature. The mixture was stirred at the same temperature for 1 day. The solvent was distilled away under reduced pressure, and thereto was added ethyl acetate (800 ml). The mixture was washed with water (1 L) and brine (approximately 1 L). The washed aqueous layer was extracted with ethyl acetate (200 ml) and combined with the previous ethyl acetate layer, and then dried over anhydrous sodium sulfate. The ethyl acetate layer was concentrated under reduced pressure, and thereto was added hexane. The precipitated crystalline powder was filtered. The filtrate was concentrated, and thereto was added hexane. The re-precipitated crystalline powder was filtered to give Compound 3 (115.22 g) as a pale brown powder.

The filtrate was concentrated and purified by silica gel chromatography (ethyl acetate-hexane 1:20 to 1:10) to give Compound 3 (11.92 g) as a white solid.
MS (APCI) 345 [M+H]$^+$ (3) Compound 3 (1.0 g), palladium acetate (16.3 mg), triphenylphosphine (38.2 mg) and triethylamine (3.2 ml) were suspended in dioxane (15 ml), and thereto was added ethyl acrylate (2.5 ml) under argon atmosphere. Then, the mixture was stirred at 80° C. under heating. After 19 hours, the reaction solution was cooled to room temperature, and the solvent was distilled away. To the residue was added water, and the mixture was extracted with ethyl acetate. The ethyl acetate layer was washed with water, dried over anhydrous sodium sulfate, and then concentrated under reduced pressure. The resulting residue was purified by silica gel column chromatography (hexane-ethyl acetate: gradient elution) to give Compound 4 (634.1 mg) as a pale brown powder.
MS (APCI) 317 [M+H]$^+$ (4) Compound 4 (2.31 g) was dissolved in ethanol (36.5 ml), and thereto was added 2N aqueous sodium hydroxide solution (18.25 ml) at room temperature. The reaction mixture was stirred at room temperature for 21 hours and adjusted to pH4 by the addition of hydrochloric acid solution under ice cooling, and then thereto was added water. The mixture was extracted with chloroform. Crystals were precipitated in chloroform layer, and then the aqueous layer was extracted with ethyl acetate. The organic layers were combined and dried over anhydrous sodium sulfate. The solvent was distilled away under reduced pressure, and the residue was triturated with isopropyl ether to give Compound 5 (1.25 g) as a pale yellow powder.
MS 187 [M−H]$^−$ (An Alternative Method)

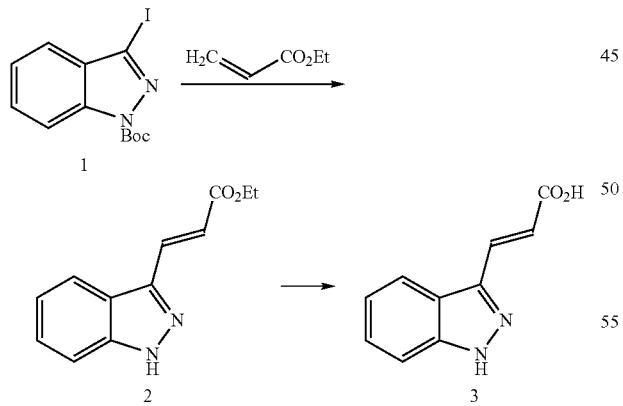

(1) Compound 1 (200 mg), 10% palladium carbon (15.4 mg) and triethylamine (0.650 ml) were suspended in anhydrous dioxane (3 ml), and thereto was added ethyl acrylate (0.500 ml) under argon atmosphere. Then, the mixture was stirred at 100° C. under heating. After 19 hours, the mixture was cooled to room temperature, and an insoluble was filtered off, and then the filtrate was concentrated under reduced pressure. To the residue was added water, and the mixture was extracted with ethyl acetate. The ethyl acetate layer was washed with water, dried over anhydrous sodium sulfate, and then concentrated under reduced pressure. The resulting residue was purified by silica gel column chromatography (hexane-ethyl acetate: gradient elution) to give Compound 2 (53.4 mg) as a colorless powder.
MS (APCI): 217 [M+H]$^+$
NMR (DMSO-d$_6$, ppm): 1.29 (3H, t, J=7.2 Hz), 4.23 (2H, q, J=7.2 Hz), 6.76 (1H, d, J=16.4 Hz), 7.26 (1H, d, J=7.5 Hz), 7.43 (1H, t, J=7.9 Hz), 7.62 (1H, d, J=8.34 Hz), 7.90 (1H, d, J=16.2 Hz), 8.11 (1H, d, J=8.2 Hz), 13.65 (1H, brs)

(2) Compound 2 was reacted or treated in the similar manner to Reference Example 1(4) to give Compound 3.

Reference Example 2

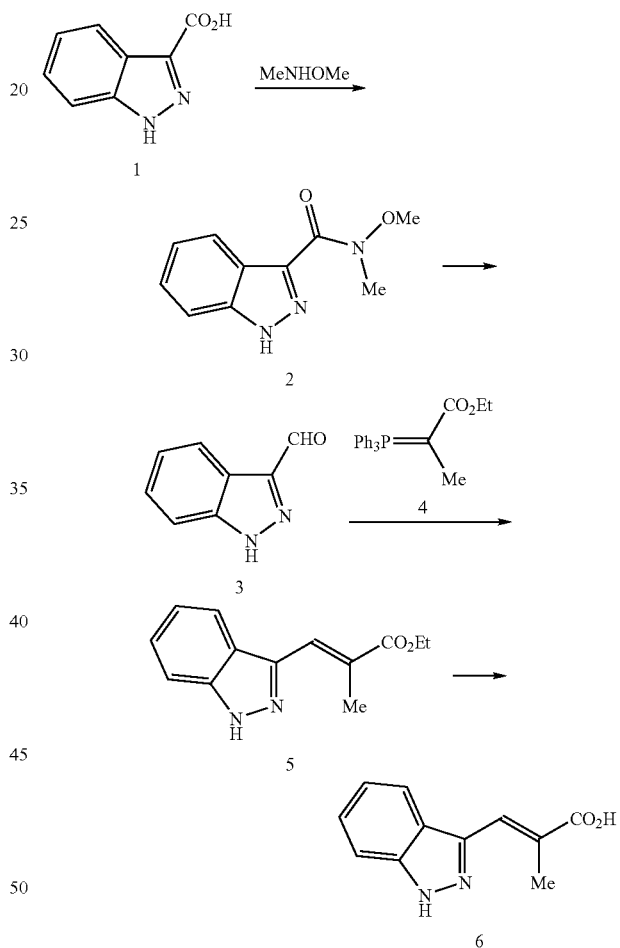

(1) Compound 1 (3.0 g), N,O-dimethylhydroxylamine hydrochloride (2.35 g) and HOBt (3.25 g) were dissolved in DMF (37 ml), and thereto was added triethylamine (3.87 ml) under ice cooling, then added WSC (4.61 g). The reaction mixture was stirred at room temperature for 18 hours, concentrated under reduced pressure, and then thereto was added water. The mixture was extracted with ethyl acetate. The extract layer was washed with an aqueous sodium bicarbonate solution and brine, and dried over anhydrous sodium sulfate. The solvent was distilled away under reduced pressure, and the residue was triturated with isopropyl ether to give Compound 2 (3.61 g) as a colorless powder.
MS (APCI) 206 [M+H]$^+$ (2) Lithium aluminum hydride (277 mg) was suspended in THF (5 ml) and cooled to about 0° C. in ice-acetone bath, and thereto was added dropwise a solution of Compound 2 (1.00 g) in THF (25 ml) over 5 minutes. The mixture was stirred for 30 minutes under ice cooling, and then, thereto were sequentially added water (277 nl), 15% aqueous sodium hydroxide solution (277 µl) and water (830 µl). Then, thereto was added ethyl acetate, and the mixture was stirred at room temperature for 5 hours. An insoluble was filtered off and washed with ethyl acetate-chloroform-methanol. The filtrate was concentrated under reduced pressure, and the residue was purified by silica gel column chromatography (eluent: methanol-chloroform 1/30) to give Compound 3 (622 mg) as a pale brown powder.

MS (APCI) 147: $[M+H]^+$, 161: $[M+H+MeOH-H_2O]^+$ (3) Compound 3 (620 mg) was dissolved in THF (21 ml), and thereto was added Compound 4 (3.84 g). The mixture was stirred at 40 to 45° C. under heating. The solvent was distilled away under reduced pressure, and the residue was purified by silica gel column chromatography (eluent: ethyl acetate-toluene 1:8) to give Compound 5 (516 mg) as a colorless powder and unreacted Compound 3 (272 mg).

MS (APCI) 231 $[M+H]^+$ (4) Compound 5 (515 mg) was suspended in ethanol (11.2 ml), and thereto was added THF (5.6 ml). Then, thereto was added 2N aqueous sodium hydroxide solution (11.2 ml) with stirring under ice cooling. The mixture was stirred at room temperature for 18 hours, acidified by the addition of 2N hydrochloric acid (11.2 ml) under ice cooling, and extracted with ethyl acetate. The extract layer was washed with brine, dried over anhydrous sodium sulfate, and then concentrated under reduced pressure. The resulting residue was triturated with ethyl acetate-hexane (1:1) and dried to give Compound 6 (338 mg) as a colorless powder.

MS (ESI-MS) 201 $[M-H]^-$

Reference Example 3

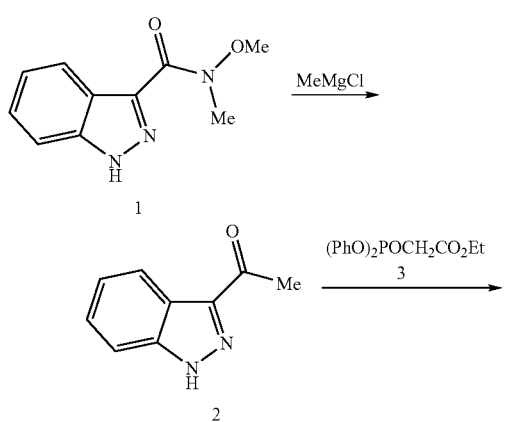

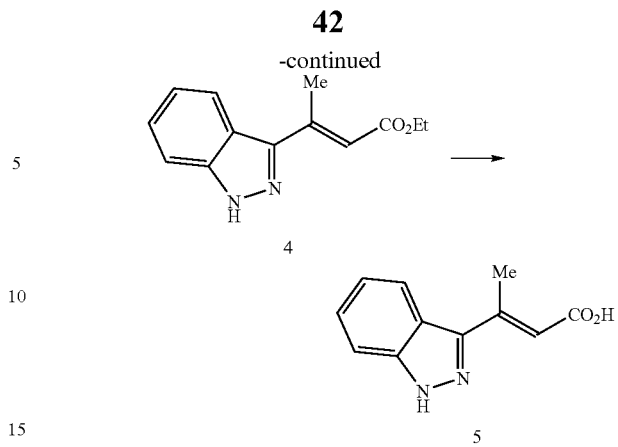

(1) To a solution of Compound 1 (17.67 g) in THF (690 ml) was added dropwise a 3.0M solution of methyl magnesium chloride in THF (86.1 ml) at −8° C. over 50 minutes with stirring under cooling. The mixture was stirred at the same temperature for 1 hour, poured into 10% aqueous ammonium chloride solution (860 ml), and extracted with ethyl acetate. The extract layer was washed with water and brine, dried over anhydrous sodium sulfate, and then the residue was purified by silica gel column chromatography (eluent: ethyl acetate-chloroform 1/7 to 1/2) to give Compound 2 (9.03 g) as a colorless powder.

MS (APCI) 161 $[M+H]^+$ (2) 60% Sodium hydride (3.11 g) was suspended in dioxane (160 ml), and thereto was added dropwise a solution of Compound 3 (13.6 g) in dioxane (80 ml) under ice cooling over 10 minutes. The mixture was stirred at room temperature for 10 minutes, and thereto was added portionwise Compound 2 (5.67 g) over 10 minutes under ice cooling. The mixture was stirred at room temperature for 10 minutes, and then stirred at 80° C. for 24 hours under heating. The reaction solution was cooled, and thereto were added water and brine. The mixture was extracted with ethyl acetate. The extract layers were combined, washed with brine, and dried over anhydrous sodium sulfate. The solvent was distilled away under reduced pressure, and the residue was purified by silica gel column chromatography (eluent: ethyl acetate/hexane 1/4). The resulting solid was triturated with isopropyl ether to give Compound 4 (3.96 g) as a pale yellow crystal.

MS (APCI) 231 $[M+H]^+$ (3) Compound 4 (2.87 g) was dissolved in ethanol (62 ml), and thereto was added 2N-aqueous sodium hydroxide solution (31 ml) under ice cooling. The mixture was stirred at room temperature for 14 hours. Then, thereto was added 2N-aqueous sodium hydroxide solution (31 ml) under ice cooling, and the mixture was stirred at room temperature for 3 days. Then, thereto was added dropwise 2N-hydrochloric acid solution (62 ml) under ice cooling. The precipitated solid was filtered, washed with water, and then dried to give Compound 5 (2.13 g) as a colorless powder.

MS (APCI) 203 $[M+H]^+$

Reference Example 4

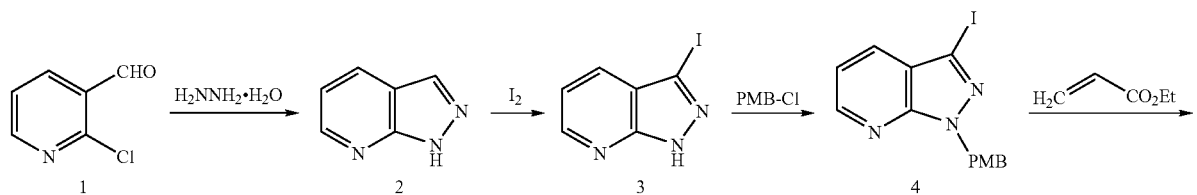

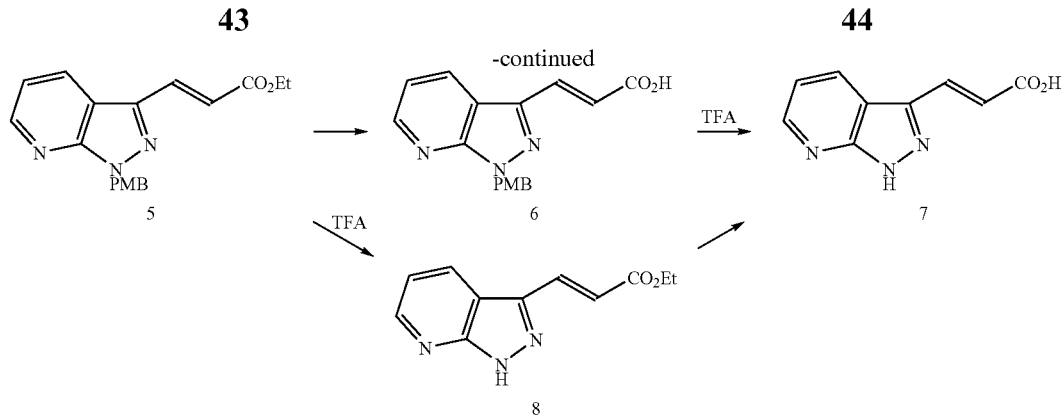

(1) According to the method described in Chemical Communications 293-294 (1966), to the mixture of Compound 1 (20.0 g) and p-toluenesulfonic acid monohydrate (15.6 g) was slowly added hydrazine monohydrate (26.6 ml) with stirring under ice cooling. The mixture was stirred at 130° C. for 21 hours under heating. The reaction mixture was left standing to cool, and then poured into 25% aqueous potassium carbonate solution and extracted with ethyl acetate. The extract layers were combined, dried over anhydrous magnesium sulfate. The solvent was distilled away under reduced pressure, and the resulting residue was purified by silica gel column chromatography (eluent: hexane-ethyl acetate 2:1 to 1:1). The resulting solid was triturated with hexane-ethyl acetate (1:1) to give Compound 2 (12.27 g) as a colorless powdery crystal.
Melting point 97.3-98° C.

(2) Compound 2 (12.2 g) was dissolved in DMF (200 ml), and thereto was added potassium hydroxide (26.86 g) with stirring under ice cooling, then added portionwise iodine (52.24 g). The mixture was allowed to warm up to room temperature and stirred at room temperature for 1 hour. The reaction mixture was poured into 10% aqueous sodium bisulfite solution (1 L), and the precipitated crystals were filtered, washed with water and then dried to give Compound 3 (21.07 g) as a pale yellow crystal.
Melting point 183.7-186.3° C.
MS (APCI) 246 [M+H]$^+$ (3) 60% Sodium hydride (10.8 g) was washed with anhydrous hexane and suspended in DMF (350 ml). Then, thereto was added dropwise a solution of Compound 3 (55.11 g) in DMF (200 ml) with stirring under ice cooling over about 2 hours, and the mixture was stirred for 1 hour under ice cooling. To the mixture was added p-methoxybenzyl chloride (36.6 ml), and then the mixture was allowed to warm up to room temperature and stirred for 1 hour. The reaction mixture was poured into ice water (3.5 L), and the precipitated crystals were filtered, washed with water and then dried. The resulting solid was triturated with chloroform-isopropyl ether (2:1) to give Compound 4 (35.0 g) as a pale red crystal.

The filtrate was concentrated under reduced pressure, and the residue was purified by silica gel column chromatography (eluent: chloroform-ethyl acetate 100:1) to give Compound 4 (29.0 g) as a pale red crystal.
Melting point 134.3-135.5° C.
MS (APCI) 366 [M+H]$^+$ (4) To a solution of Compound 4 (24.7 g) in dioxane (430 ml) were added triphenylphosphine (3.55 g), palladium acetate (1.52 g) and triethylamine (123 ml). After substitution by argon, to the mixture was added ethyl acrylate (74 ml), and the mixture was stirred at 100° C. for 4 hours under heating. The reaction mixture was left standing to cool to room temperature, and concentrated under reduced pressure. The resulting residue was dissolved in ethyl acetate, washed with water and brine, and dried over anhydrous sodium sulfate. The mixture was concentrated under reduced pressure, and the resulting residue was purified by silica gel column chromatography (eluent: hexane-ethyl acetate 4:1 to 3:1). The resulting solid was triturated with isopropyl ether and dried to give Compound 5 (20.838 g) as a colorless crystal.
Melting point 105.9-106.8° C.
MS (APCI) 338 [M+H]$^+$ (5) To a solution of Compound 5 (19.2 g) in THF-ethanol (80 ml-160 ml) was added 2N aqueous sodium hydroxide solution (140 ml) under ice cooling, and the mixture was stirred at room temperature for 2 hours. To the reaction mixture was added 2N hydrochloric acid (140 ml) under ice cooling, and then added water. The precipitated crystals were filtered, washed with water, and then dried to give Compound 6 (16.9 g) as a colorless crystal. The filtrate was extracted with ethyl acetate-THF mixture, and the extract layer was washed with brine and dried over anhydrous sodium sulfate. The mixture was concentrated under reduced pressure, and the residue was triturated with diethyl ether to give Compound 6 (0.52 g) as a colorless crystal. The crystals were combined with the previously obtained crystals to give Compound 6 (17.42 g).
MS (ESI) 308 [M−H]$^−$ (6) Compound 6 (522.9 mg) was suspended in trifluoroacetic acid (5 ml) and refluxed under heating. After 16 hours, the reaction mixture was concentrated under reduced pressure, and triturated with methanol-ethyl acetate to give Compound 7 (0.303 g) as a pale yellow crystal. Melting point 269.0-271.2° C.
MS (APCI) 190 [M+H]$^+$ (7) Compound 5 (45.7 g) was suspended in trifluoroacetic acid (300 ml) and the mixture was refluxed for 3.5 hours under heating. The reaction mixture was cooled, concentrated under reduced pressure, and then to the residue were added ethyl acetate (100 ml) and 10% aqueous potassium carbonate solution. The mixture was stirred. The precipitated crystals were filtered, washed with water, isopropyl ether and ethyl acetate, and dried to give Compound 8 (28.12 g) as a colorless crystal. Melting point 170.5-171.0° C.
MS (APCI) 218 [M+H]$^+$
IR (Nujor) 1672 cm$^{-1}$ (8) To a solution of Compound 8 (33.22 g) in THF-ethanol (200 ml-200 ml) was added 2N aqueous sodium hydroxide solution (338 ml) under ice cooling, and the mixture was stirred at room temperature for 16 hours. The reaction mixture was concentrated under reduced pressure, and adjusted to pH3 by the addition of 2N hydrochloric acid (340 ml) with stirring under ice cooling. The precipitated crystals were filtered, washed with water, and then dried, and triturated with chloroform to give Compound 7 (26.63 g) as a colorless crystal.
Melting point 272.4-274° C.
MS (APCI) 190 [M+H]$^+$
IR (Nujor) 1685 cm$^{-1}$ Reference Example 5

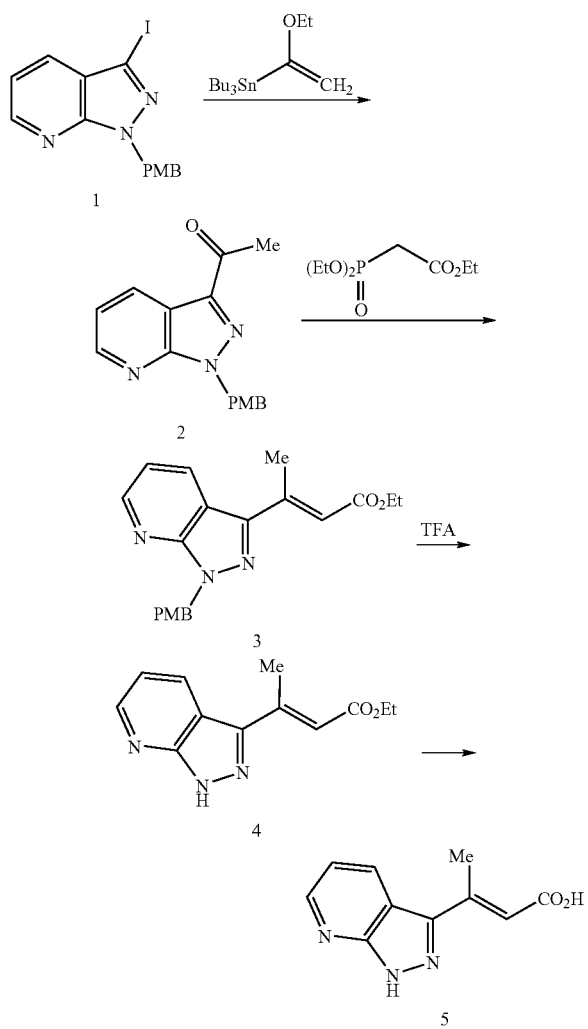

(1) Compound 1 (500 mg) and 1-ethoxyvinyltributoxy tin (663 mg) were suspended in dioxane (5 ml). To the mixture was added dichlorobistriphenylphosphine palladium (II) (49 mg) under argon atmosphere, and the mixture was refluxed for 21 hours under heating. The reaction mixture was left standing to cool, and then thereto was added ethyl acetate, then added 10% aqueous potassium fluoride solution. The mixture was stirred at room temperature for 1 hour. An insoluble was filtered off through Celite, and to the filtrate was added water, and the mixture was separated. To the organic layer was added 1N hydrochloric acid. The mixture was vigorously stirred at room temperature and neutralized by the addition of a saturated aqueous sodium bicarbonate solution, and then the organic layer was separated, washed with brine, and dried over anhydrous magnesium sulfate. The solvent was distilled away under reduced pressure, and the resulting residue was purified by silica gel column chromatography (eluent: hexane-ethyl acetate 9:1 to 2:1) to give Compound 2 (321.6 mg) as a pale yellow solid.
MS (APCI) 282 [M+H]$^+$
NMR (DMSO-d$_6$) ppm 2.63 (3H, s), 3.71 (3H, s), 5.75 (2H, s), 6.90 (2H, d, J=8.5 Hz), 7.31 (2H, d, J=8.5 Hz), 7.47 (1H, m), 8.58 (1H, d, J=8 Hz), 8.71 (1H, d, J=3 Hz)

(2) To a suspension of 60% sodium hydride (2.13 g) in dioxane (40 ml) was added dropwise a solution of diethylphosphonoacetic acid ethyl ester (11.95 g) in dioxane (40 ml) with stirring at room temperature over 15 minutes. The mixture was stirred at room temperature for 1 hour, and thereto was added Compound 2 (5.00 g). The mixture was stirred at 55 to 58° C. for 3 hours. The reaction mixture was cooled, and thereto was added water (100 ml). The mixture was extracted with ethyl acetate. The extract layers were combined, washed with brine, dried over anhydrous magnesium sulfate, and concentrated under reduced pressure. The residue was purified by silica gel column chromatography (eluent: chloroform). The resulting fraction (9.41 g) was dissolved in dioxane (30 ml), and thereto was added 60% sodium hydride (1.07 g) at room temperature, and added dropwise a solution of ethanol (1.56 ml) in dioxane (10 ml). The mixture was stirred at 45 to 55° C. under heating, cooled, and then thereto was added water (40 ml). The mixture was extracted with ethyl acetate. The extract layers were combined, washed with brine, dried over anhydrous sodium sulfate, and then concentrated under reduced pressure. The resulting residue was purified by silica gel column chromatography (eluent: hexane-ethyl acetate gradient) to give Compound 3 (4.86 g) as a colorless solid.
MS (APCI) 352 [M+H]$^+$
NMR (DMSO-d$_6$) ppm 1.27 (3H, t, J=7 Hz), 2.66 (3H, s), 3.70 (3H, s), 4.18 (2H, q, J=7 Hz), 5.66 (2H, s), 6.59 (1H, s), 6.87 (2H, d, J=8.7 Hz), 7.27 (2H, d, J=8.7 Hz), 7.36 (1H, dd, J=4.5, 8.7 Hz), 8.51 (1H, d, J=7.9 Hz), 8.65 (1H, d, J=4.1 Hz)

(3) Compound 3 (4.86 g) was suspended in trifluoroacetic acid (48.6 ml), and refluxed under heating. After 4 hours, the suspension was cooled, and then concentrated under reduced pressure, and the residue was dissolved in ethyl acetate. The mixture was washed with aqueous sodium bicarbonate solution and brine, dried over anhydrous sodium sulfate, and then concentrated under reduced pressure. The residue was purified by silica gel column chromatography (eluent: chloroform-ethyl acetate gradient) to give Compound 4 (3.36 g) as a colorless powder.
MS (APCI) 232 [M+H]$^+$
NMR (DMSO-d$_6$) ppm 1.27 (3H, t, J=7 Hz), 2.68 (3H, s), 4.19 (2H, q, J=7 Hz), 6.59 (1H, s), 7.31 (1H, dd, J=4.8 Hz), 8.47 (1H, d, J=8 Hz), 8.58 (1H, d, J=4 Hz), 14.18 (1H, br. s)

(4) Compound 4 (3.36 g) was dissolved in THF-ethanol (34 ml-34 ml), and thereto was added 2N aqueous sodium hydroxide solution (34.6 ml). The mixture was stirred at 50° C. under heating. After 8 hours, the reaction solution was cooled to room temperature. The solvent was distilled away under reduced pressure, and thereto was added 2N hydrochloric acid (34.5 ml). The mixture was cooled slowly. The precipitated colorless crystals were filtered, and dried to give Compound 5 (2.05 g) as a colorless powder.
MS (APCI) 204 [M+H]$^+$
NMR (DMSO-d$_6$) ppm 2.65 (3H, s), 6.58 (1H, s), 7.31 (1H, dd, J=4, 8 Hz), 8.46 (1H, d, J=8 Hz), 8.57 (1H, d, J=4 Hz), 12.4 (1H, br.s), 14.0 (1H, s)

Reference Example 6

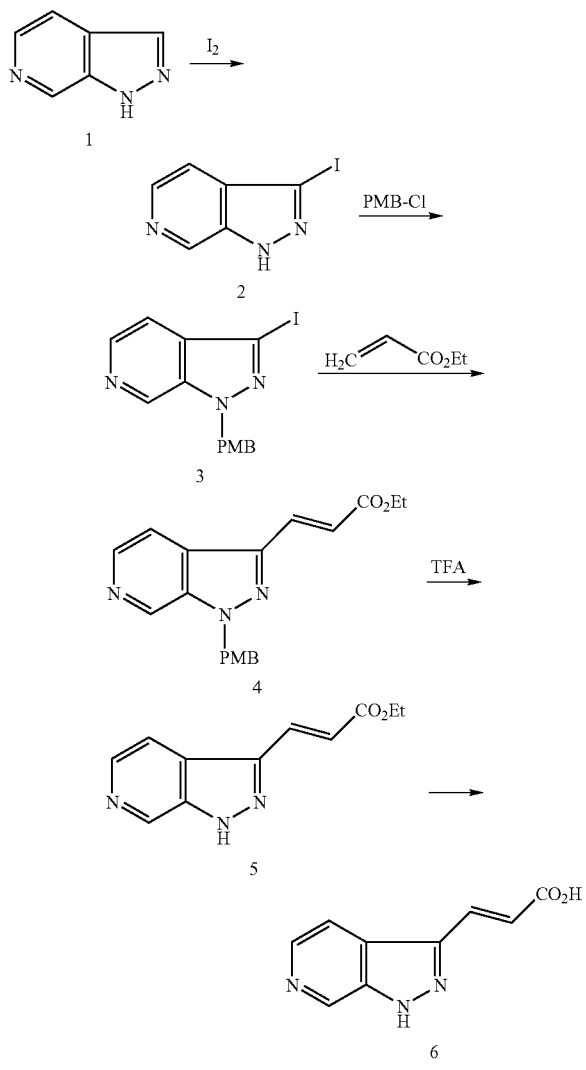

(1) Compound 1 (4.20 g) was dissolved in DMF (70 ml), and thereto was added potassium hydroxide (9.20 g) under ice cooling, then added portionwise iodine (17.9 g). The mixture was slowly allowed to warm up to room temperature, and stirred for 30 minutes. The reaction mixture was poured into 10% aqueous sodium metabisulfite solution (350 ml), and the precipitated crystals were filtered, washed with water, and then dried to give Compound 2 (5.76 g) as a pale brown powder.
MS (APCI) 246 [M+H]$^+$ (2) 60% Sodium hydride (204 mg) was suspended in DMF (4.3 ml), and thereto was added dropwise a solution of Compound 2 (1.00 g) in DMF (12 ml) under ice cooling over about 5 minutes. The mixture was stirred at room temperature for 1 hour. The mixture was ice-cooled, and thereto was added p-methoxybenzyl chloride (664 µl). Then, the mixture was allowed to warm up to room temperature, and stirred for 2 hours. The reaction mixture was poured into ice water (80 ml), and extracted with ethyl acetate. The extract layers were combined, washed with brine, dried over anhydrous sodium sulfate, and then concentrated under reduced pressure. The residue was triturated with ethyl acetate-isopropyl ether (1:1), and the product was filtered to give Compound 3 (746 mg) as a pale pink powder. The filtrate was concentrated under reduced pressure, and the residue was purified by silica gel column chromatography, and then triturated with isopropyl ether to give Compound 3 (309 mg) as a pale pink powder.
MS (APCI) 366 [M–H]$^+$ (3) To a solution of Compound 3 (744 mg) in dioxane (10.2 ml) were added triphenylphosphine (26.8 mg), palladium acetate (11.4 mg) and triethylamine (2.27 ml). To the mixture was added ethyl acrylate (1.77 ml) under argon atmosphere, and the mixture was stirred at 100° C. for 22 hours under heating. The reaction mixture was left standing to cool to room temperature, and concentrated under reduced pressure. The resulting residue was purified by silica gel column chromatography (eluent: chloroform-ethyl acetate 2:1), and the resulting solid was triturated with isopropyl ether to give Compound 4 (328 mg) as a pale yellow powder.
MS (APCI) 218 [M–H]$^+$ (4) Compound 4 (590 mg) was suspended in trifluoroacetic acid (17.5 ml) and refluxed under heating. After 23 hours, the reaction solution was concentrated under reduced pressure, and purified by NH-silica gel column chromatography (eluent: methanol-chloroform 1:50) to give Compound 5 (328 mg) as a pale yellow powder.
MS (APCI) 218 [M+H]$^+$ (5) Compound 5 (327 mg) was dissolved in THF-ethanol (3.8 ml-3.8 ml), and thereto was added 2N aqueous sodium hydroxide solution (3.76 ml). The mixture was stirred at room temperature for 21 hours. To the mixture was added dropwise 2N hydrochloric acid (3.76 ml) with stirring under ice cooling. The precipitated colorless crystals were filtered, washed with water-ethanol (10:1) and isopropyl ether, and dried to give Compound 6 (279 mg) as a colorless powder.
MS (ESI) 188 [M–H]$^-$

Reference Example 7

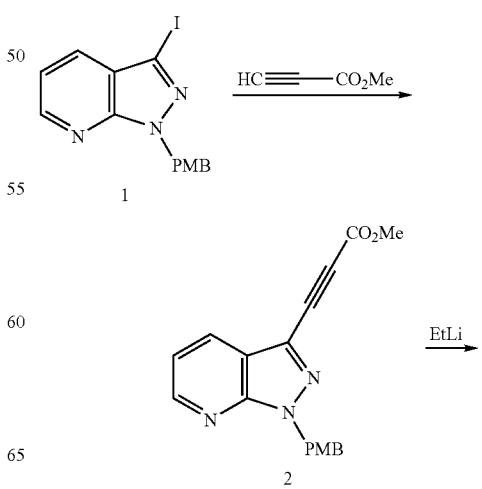

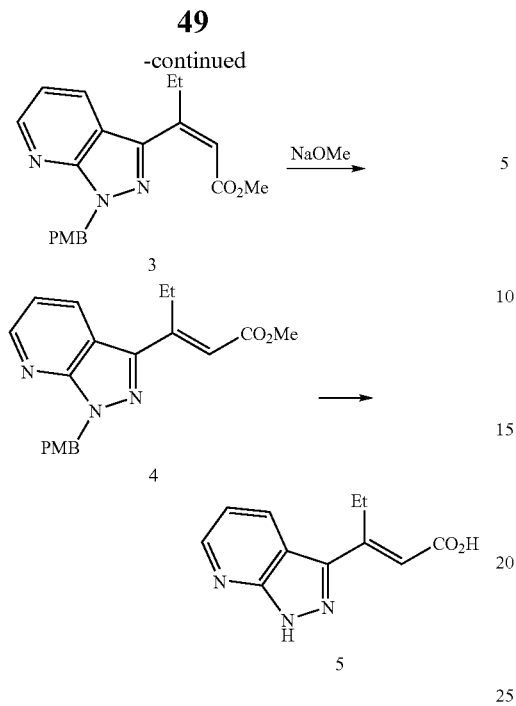

(1) Compound 1 (2.00 g), copper iodide (I) (105 mg), sodium bicarbonate (953 mg) and methyl propiolate (1.84 g) were suspended in DMF (50 ml). To the mixture was added dichlorobistriphenylphosphine palladium (II) (384 mg) under argon atmosphere, and the mixture was stirred at 60° C. for 6 hours under heating. The reaction mixture was left standing to cool, and thereto was added ethyl acetate. Then, the mixture was washed with brine and dried over anhydrous magnesium sulfate. The solvent was distilled away under reduced pressure, and the resulting residue was purified by silica gel column chromatography (eluent: hexane-ethyl acetate 20:1 to 3:1) to give Compound 2 (1.09 g) as a pale yellow powder.
MS (APCI) 322 [M+H]$^+$ (2) Copper iodide (I) (1.94 g) was suspended in diethyl ether (20 ml). Then, thereto was added dropwise a 0.5M solution of ethyl lithium in benzene-cyclohexane (41 ml) with stirring at 0° C. over 30 minutes. Then, thereto was added dropwise a solution of Compound 2 (1.09 g) in THF (10 ml) with stirring at −78° C. over 20 minutes. The mixture was stirred at −78° C. for 30 minutes, and then thereto was added water (2 ml). The mixture was allowed to warm up to room temperature. An insoluble was filtered off through Celite and washed with ethyl acetate. To the filtrate was added an aqueous citric acid solution, and the mixture was separated. The organic layer was washed with brine, dried over anhydrous magnesium sulfate, and concentrated under reduced pressure. The residue was purified by silica gel column chromatography (eluent: hexane-ethyl acetate 20:1 to 7:3) to give Compound 3 (1.15 g) a red oil.
MS (APCI) 352 [M+H]$^+$ (3) To a solution of Compound 3 (1.00 g) in dioxane (30 ml) was added a 28% solution of sodium methoxide in methanol (0.2 ml). The mixture was stirred at 50° C. for 1 hour under heating. The reaction mixture was cooled, and then thereto was added an aqueous citric acid solution. The mixture was extracted with ethyl acetate. The extract layer was washed with brine, dried over anhydrous magnesium sulfate, and concentrated under reduced pressure. The residue was purified by silica gel column chromatography (eluent: hexane-ethyl acetate 20:1 to 7:3) to give Compound 4 (289 mg) as a colorless powder.
MS (APCI) 352 [M+H]$^+$ (4) Compound 4 (280 mg) was suspended in trifluoroacetic acid (6 ml) and the mixture was refluxed under heating. After 18 hours, the suspension was cooled, and then concentrated under reduced pressure. To the residue was added 3:1 mixed solvent of methanol and ethanol, and an insoluble was filtered off through Celite. The filtrate was concentrated under reduced pressure. To the residue were added ethanol (3 ml), THF (3 ml) and 2N aqueous sodium hydroxide solution (1 ml), and the mixture was stirred at room temperature for 18 hours. The reaction mixture was concentrated under reduced pressure, and then thereto was added 2N hydrochloric acid (1 ml) under ice cooling. The mixture was extracted with ethyl acetate. The extract layer was washed with brine, dried over anhydrous magnesium sulfate, and concentrated under reduced pressure. The residue was triturated with a mixed solvent of ethyl acetate and isopropyl ether, filtered and dried to give Compound 5 (124 mg) as a colorless powder.
MS (APCI) 218 [M−H]$^+$ Reference Example 8

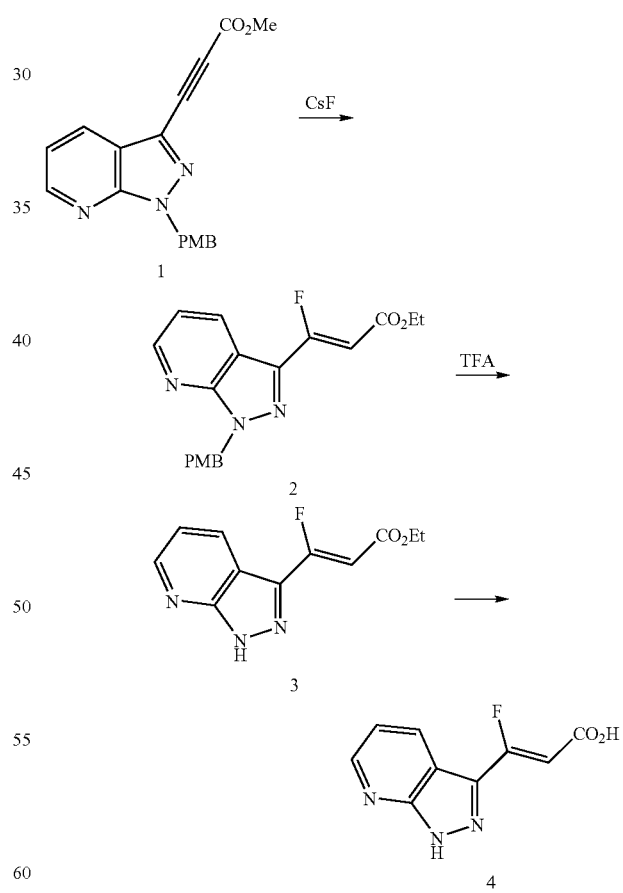

(1) To a solution of Compound 1 (8.11 g) in DMF (325 ml) were added cesium fluoride (11.5 g), potassium bifluoride (2.76 g) and water (3.63 ml), and the mixture was stirred at 80° C. for 24 hours under heating. The reaction mixture was left standing to cool, and thereto was added ethyl acetate. Then, the mixture was washed with brine and dried over anhydrous sodium sulfate. The solvent was distilled away under reduced pressure, and the resulting residue was purified by silica gel column chromatography (eluent: hexane-ethyl acetate 4:1 to 2:1) to give Compound 2 (4.34 g) as a pale yellow solid.
MS (APCI) 342 [M+H]⁺

(2) Compound 2 (4.34 g) was dissolved in trifluoroacetic acid (87 ml) and the mixture was refluxed under heating for 3 days. The mixture was cooled, and then concentrated under reduced pressure. To the residue were added chloroform and aqueous sodium bicarbonate solution, and the mixture was separated. The extract layer was dried over anhydrous magnesium sulfate, and concentrated under reduced pressure. The resulting residue was purified by silica gel column chromatography (eluent: chloroform-THF-methanol 10:1:0 to 20:1:1) to give Compound 3 (2.70 g) as a pale brown powder.
MS (APCI) 222 [M+H]⁺

(3) Compound 3 (2.70 g) was suspended in THF (30.5 ml), and thereto was added 2N aqueous sodium hydroxide solution (30.5 ml) under ice cooling. The mixture was stirred at room temperature for 5 hours. Then, thereto was added dropwise 1N hydrochloric acid solution (61 ml) under ice cooling, and the precipitated solid was filtered, washed with water, and then dried to give Compound 4 (2.13 g) as a gray white powder.
MS (APCI) 208 [M+H]⁺

Reference Example 9

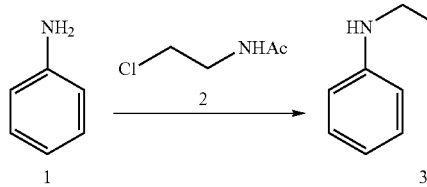

To a solution of Compound 2 (4.82 g) in toluene (80 ml) was added Compound 1 (11.1 g), and the mixture was refluxed under heating for 6 hours. The reaction mixture was ice-cooled, and thereto was added saturated sodium bicarbonate water. The mixture was extracted with ethyl acetate. The extract layers were combined, dried over anhydrous sodium sulfate, and the solvent was distilled away under reduced pressure. The resulting residue was purified by silica gel column chromatography to give Compound 3 (2.77 g) as a pale brown oil.
MS (APCI) 179 [M−H]⁺

Reference Example 10

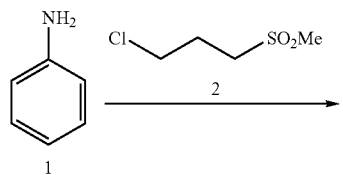

-continued

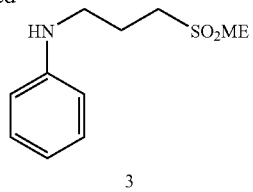

To a solution of Compound 2 (1.38 g) in toluene (17 ml) was added Compound 1 (4.01 g), and the mixture was refluxed under heating for 2 days. The reaction mixture was ice-cooled, and thereto was added saturated sodium bicarbonate water. The mixture was extracted with ethyl acetate. The extract layers were combined, dried over anhydrous sodium sulfate, and the solvent was distilled away under reduced pressure. The resulting residue was purified by silica gel column chromatography to give Compound 3 (1.10 g) as a pale brown oil.
MS (APCI) 214 [M−H]⁺

Reference Example 11-1

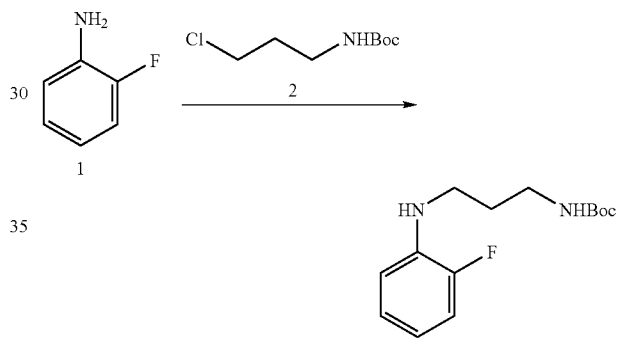

To Compound 2 (1.50 g) were added Compound 1 (2.25 ml), tetra-n-butylammonium iodide (30 mg) and sodium iodide (30 mg), and the mixture was stirred at 100° C. for 2 days under heating. The reaction mixture was ice-cooled, and thereto was added saturated sodium bicarbonate water. The mixture was extracted with ethyl acetate. The extract layer was washed with brine, dried over anhydrous magnesium sulfate, and the solvent was distilled away under reduced pressure. The resulting residue was purified by silica gel column chromatography (eluent: hexane-ethyl acetate 20:1 to 4:1) to give Compound 3 (508 mg) as an orange-colored oil.
MS (APCI) 269 [M+H]⁺

Reference Example 11-2

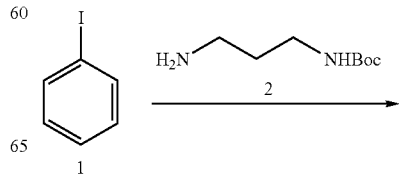

-continued

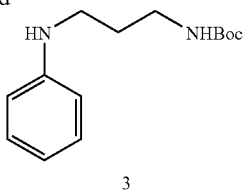

3

Compound 2 (12.3 g), Compound 1 (12.0 g), cesium acetate (28.2 g) and copper iodide (11.2 g) were dissolved in DMSO (15 ml). The mixture was stirred under argon atmosphere at 90° C. under heating overnight. After cooling, thereto was added water, and the mixture was extracted with ethyl acetate. The extract layers were combined, washed with saturated aqueous sodium bicarbonate solution and brine, and dried over anhydrous sodium sulfate, and then the solvent was distilled away under reduced pressure. The residue was purified by silica gel column chromatography (eluent: ethyl acetate-n-hexane gradient) to give Compound 3 (8.71 g) as a colorless oil.

MS (APCI) 251 [M+H]+
IR (Nujol) 3356, 1683 cm$^{-1}$.

Reference Examples 11-3 to 11-6

The following compounds were obtained by reacting or treating in the similar manner to Reference Example 11-2.

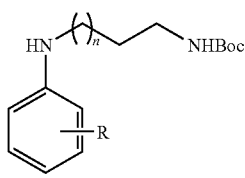

| Reference Examples | R | n | MS(APCI) [M + H]+ |
|---|---|---|---|
| 11-3 | 2-OMe | 1 | 281 |
| 11-4 | 3-OMe | 1 | 281 |
| 11-5 | 3-OMe | 0 | 267 |
| 11-6 | 4-OMe | 1 | 281 |

Reference Example 11-7

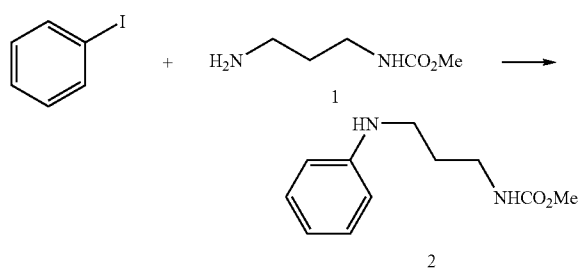

Cesium acetate (7.29 g) and copper iodide (2.89 g) were azeotroped to dryness with toluene, and thereto were sequentially added a solution of Compound 1 (2.41 g) in DMSO (10 ml), iodobenzene (1.90 ml) and DMSO (5 ml). The mixture was deaerated, and then filled with argon. The mixture was stirred at 90° C. for 20 hours under heating. Then, thereto were added ammonia water (15 ml), brine (15 ml), water (15 ml) and ethyl acetate (100 ml) under ice cooling, and the mixture was stirred and then separated. The aqueous layer was extracted with ethyl acetate, and the extract layers were combined, washed with brine and dried over anhydrous sodium sulfate. The solvent was distilled away under reduced pressure, and the resulting brown oil (3.66 g) was purified by silica gel column chromatography (eluent: 5 to 20% ethyl acetate-chloroform gradient) to give Compound 2 (1536 mg) as a pale yellow oil.

MS (APCI) 209 [M+H]+

Reference Example 12

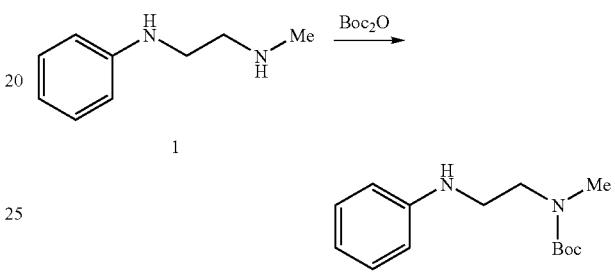

Compound 1 (2.971 g) was dissolved in methanol (30 ml), and thereto was slowly added dropwise a solution of di-t-butyl dicarbonate (4.46 g) in methanol (30 ml) at room temperature. The mixture was stirred for 2.5 hours, and the solvent was distilled away under reduced pressure. Then, the residue was purified by silica gel column chromatography (eluent: hexane-ethyl acetate 5:1) to give Compound 2 (2.71 g) as a colorless powder.

MS (APCI) 251 [M+H]+

Reference Example 13-1

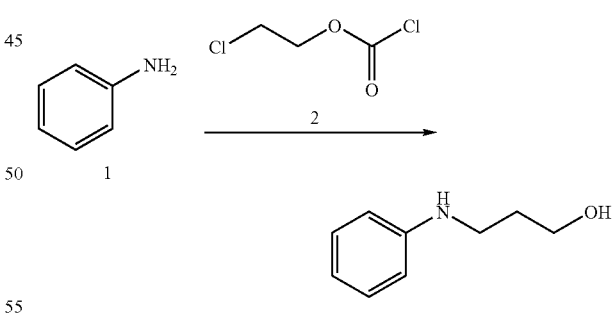

To a solution of Compound 1 (3.78 g) in toluene (50 ml) was added dropwise a solution of Compound 2 (2.50 ml) in toluene (10 ml) under ice cooling, and the mixture was stirred at room temperature for 2 hours. The precipitate was filtered off, and thereto was added 5% aqueous citric acid solution. The mixture was extracted with ethyl acetate. The extract layers were combined, washed with brine, and dried over anhydrous sodium sulfate. The solvent was distilled away under reduced pressure, and the resulting oil was dissolved in ethanol (25 ml). Then, thereto was added potassium hydroxide (5.55 g), and the mixture was refluxed under heating for 1 hour. The reaction mixture was cooled to room temperature, and thereto was added ethanol. An insoluble was filtered off, and the filtrate was concentrated under reduced pressure. The resulting residue was purified by silica gel column chromatography (eluent: chloroform-ethyl acetate 10:1) to give Compound 3 (2.92 g) as a pale brown oil.

MS (APCI) 152 [M+H]+

Reference Examples 13-2 to 13-12

The following compounds were obtained by reacting and treating in the similar manner to Reference Example 13-1.

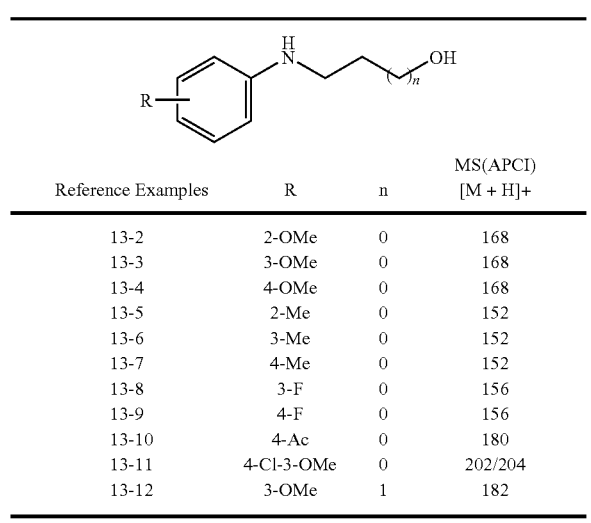

| Reference Examples | R | n | MS(APCI) [M + H]+ |
|---|---|---|---|
| 13-2 | 2-OMe | 0 | 168 |
| 13-3 | 3-OMe | 0 | 168 |
| 13-4 | 4-OMe | 0 | 168 |
| 13-5 | 2-Me | 0 | 152 |
| 13-6 | 3-Me | 0 | 152 |
| 13-7 | 4-Me | 0 | 152 |
| 13-8 | 3-F | 0 | 156 |
| 13-9 | 4-F | 0 | 156 |
| 13-10 | 4-Ac | 0 | 180 |
| 13-11 | 4-Cl-3-OMe | 0 | 202/204 |
| 13-12 | 3-OMe | 1 | 182 |

Reference Example 14

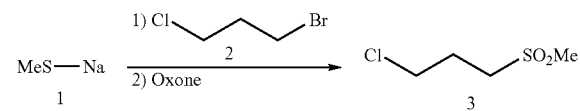

To a solution of Compound 1 (19.18 g) and ethyl acetate-hexane 1:20 to 1:10 in ethanol (600 ml) was added dropwise a solution of Compound 2 (54.1 ml) in ethanol (30 ml) at 3° C. over 30 minutes. The reaction mixture was stirred at 7° C. for 18.5 hours, and thereto was added water (600 ml), added oxone (504.6 g) at 3° C. The mixture was stirred at the same temperature for 3 hours. An insoluble was filtered through Celite, and the filtrate was concentrated under reduced pressure and then extracted with ethyl acetate. The extract layers were combined, washed with brine and dried over anhydrous sodium sulfate, and then the solvent was distilled away under reduced pressure. The residue was distilled under reduced pressure to give Compound 3 (38.047 g).

Boiling point: 112 to 123° C./1 mmHg

MS (APCI) 176 [M+NH$_4$+2]+/174 [M+NH$_4$]+

NMR (DMSO-d$_6$) ppm 2.12-2.17 (2H, m), 3.01 (3H, s), 3.22-3.25 (2H, m), 3.76 (2H, t, J=6.5 Hz)

Reference Example 15-1

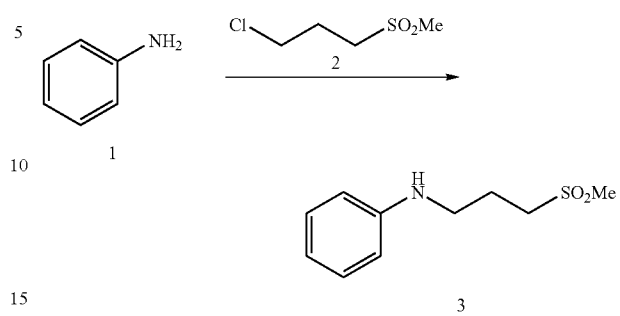

Compound 2 (1.38 g) was dissolved in toluene (17 ml), and thereto was added Compound 1 (4.01 ml). The mixture was refluxed under heating for 2 days. The reaction mixture was cooled, and then thereto was added an aqueous sodium bicarbonate solution. The mixture was extracted with ethyl acetate. The extract layers were combined, washed with brine, dried over anhydrous sodium sulfate, and then concentrated under reduced pressure. The resulting residue was purified by silica gel column chromatography (eluent: chloroform-ethyl acetate 10:1) to give Compound 3 (1.10 g) as a colorless crystal.

MS (APCI) 214 [M+H]+

Reference Examples 15-2 to 15-8

The following compounds were prepared by reacting and treating in the similar manner to Reference Example 15-1.

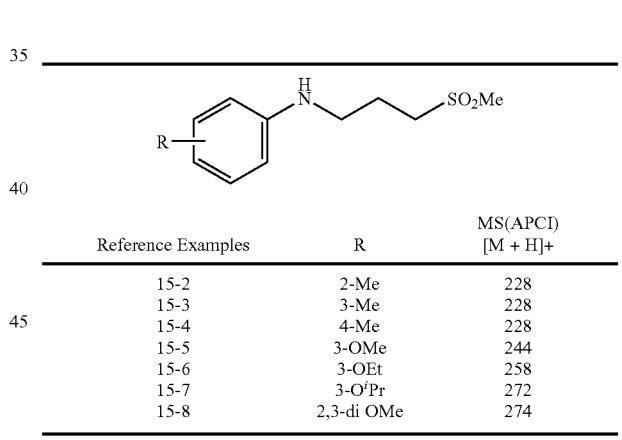

| Reference Examples | R | MS(APCI) [M + H]+ |
|---|---|---|
| 15-2 | 2-Me | 228 |
| 15-3 | 3-Me | 228 |
| 15-4 | 4-Me | 228 |
| 15-5 | 3-OMe | 244 |
| 15-6 | 3-OEt | 258 |
| 15-7 | 3-O$^i$Pr | 272 |
| 15-8 | 2,3-di OMe | 274 |

Reference Example 16

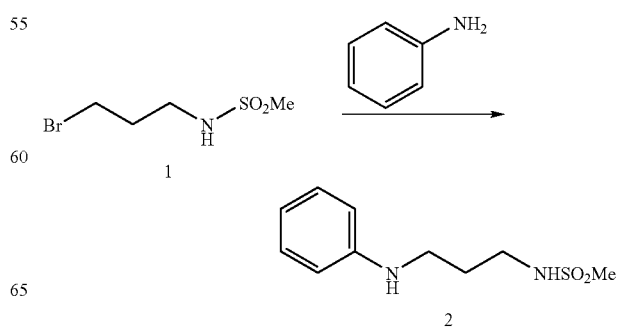

Compound 1 (1.28 g), which is synthesized from 3-bromopropylamine hydrobromide, and aniline (1.38 g) were stirred at 110° C. under heating for 1 hour under argon atmosphere. The reaction mixture was cooled, diluted with ethyl acetate, washed with a saturated aqueous sodium bicarbonate solution and brine, and dried over anhydrous sodium sulfate. The solvent was distilled away under reduced pressure, and the residue was purified by silica gel column chromatography (eluent: hexane-ethyl acetate 2:1 to 1:1) to give Compound 2 (1.10 g) as a pale brown oil.

MS (APCI) 229 [M+H]$^+$

Reference Example 17-1

Lithium perchlorate (14.76 g) was suspended in diethyl ether (27.7 ml), and thereto were added Compound 1 (1.38 ml) and Compound 2 (1.23 ml) under ice cooling. The mixture was stirred at room temperature for 1.5 hours, and then poured into water and extracted with chloroform. The extract layers were combined, washed with brine, dried over anhydrous sodium sulfate, and then concentrated under reduced pressure. The resulting residue was purified by silica gel column chromatography (eluent: hexane-ethyl acetate gradient) to give Compound 3 (895 mg) as a colorless oil.

MS (APCI) 166 [M+H]$^+$

Reference Examples 17-2 to 17-10

The following compounds were obtained by reacting and treating in the similar manner to Reference Example 17-1.

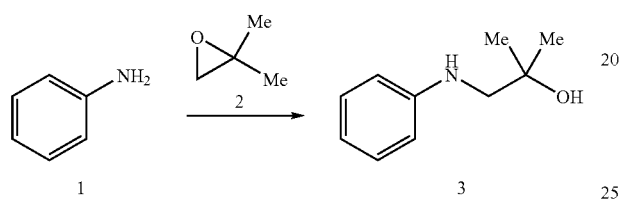

| Reference Examples | R | MS(APCI) [M + H]+ |
|---|---|---|
| 17-2 | 3-OMe | 196 |
| 17-3 | 4-OMe | 196 |
| 17-4 | 2-OMe | 196 |
| 17-5 | 2,3-di OMe | 226 |
| 17-6 | 3-Me | 180 |
| 17-7 | 3-F | 184 |
| 17-8 | 4-F | 184 |
| 17-9 | 2-F | 184 |
| 17-10 | 3-CN | 191 |

Reference Example 18-1

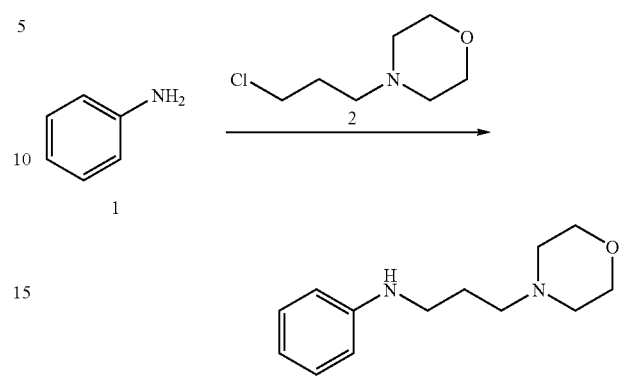

Compound 1 (835 μl) was mixed with Compound 2 (500 mg) and the mixture was stirred at 120° C. for 1 hour. The reaction solution was left standing to cool, and thereto was added 10% aqueous potassium carbonate solution. The mixture was extracted with chloroform. The extract layers were combined, dried over anhydrous sodium sulfate, and then concentrated under reduced pressure. The resulting residue was purified by silica gel column chromatography (eluent: chloroform-methanol 1:30) to give Compound 3 (631 mg) as a pale brown oil.

MS (APCI) 221 [M+H]$^+$

Reference Examples 18-2 to 18-6

The following compounds were obtained by reacting and treating in the similar manner to the above Reference Example.

| Reference Examples | W | MS(APCI) [M + H]+ |
|---|---|---|
| 18-2 | morpholinoethyl | 207 |
| 18-3 | methylthiazolyl | 191 |
| 18-4 | methylpyrazolyl (NH) | 188 |
| 18-5 | ethylpyrazolyl | 174 |

-continued

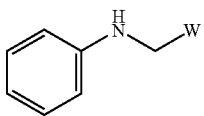

| Reference Examples | W | MS(APCI) [M + H]+ |
|---|---|---|
| 18-6 | 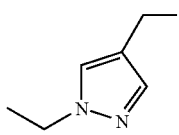 | 218 |

Reference Example 19

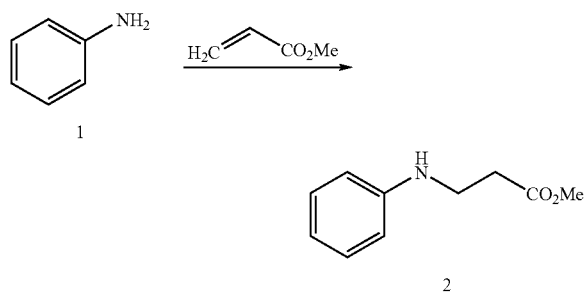

Compound 2 was prepared according to the method described in J. Chem. Soc., 4166 (1957). Melting point 36.0 to 37.5° C.

MS (APCI) 180 [M+H]⁺

Reference Example 20-1

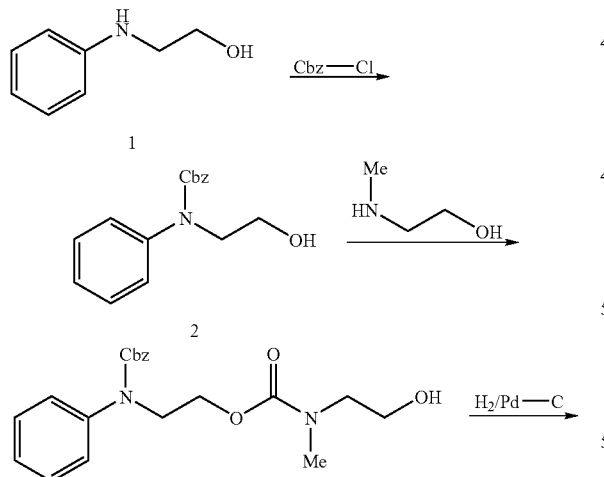

(1) Compound 1 (1.50 g) was dissolved in chloroform (22 ml), and thereto was added pyridine (1.33 ml) under ice cooling and added dropwise a solution of carbobenzoxy chloride (1.87 ml) in chloroform (5 ml) over 3 minutes. The mixture was stirred for 30 minutes. Then, thereto was added 1N hydrochloric acid (22 ml) under ice cooling, and the mixture was extracted with chloroform. The extract layers were combined, washed with brine, dried over anhydrous sodium sulfate, and then the solvent was distilled away under reduced pressure. The residue was purified by silica gel column chromatography (eluent: chloroform-ethyl acetate 6:1) to give Compound 2 (3006 mg) as a colorless oil.

(2) Compound 2 (1500 mg) was dissolved in acetonitrile (25 ml), and thereto were added N,N'-succinimidyl carbonate (1856 mg) and N,N'-dimethylaminopyridine (68 mg). The mixture was stirred at room temperature for 15 hours. Then, thereto was added additional N,N'-succinimidyl carbonate (286 mg), and the mixture was stirred for 3 hours. Then, thereto was added a solution of 2-methylaminoethanol (831 mg) in acetonitrile (3 ml), and the mixture was stirred at room temperature for 1 hour. Then, thereto was added an aqueous sodium bicarbonate solution, and the mixture was extracted with ethyl acetate. The extract layers were combined, washed with brine and dried over anhydrous sodium sulfate, and then the solvent was distilled away under reduced pressure. The residue was purified by silica gel column chromatography (eluent: ethyl acetate-chloroform 3:2) to give Compound 3 (1876 mg) as a colorless oil.

MS (APCI) 373 [M+H]⁺

(3) Compound 3 (1874 mg) was dissolved in methanol (25 ml), and thereto was added 10% aqueous palladium carbon (583 mg). The mixture was vigorously stirred for 4 hours under hydrogen atmosphere. Palladium carbon was filtered off through Celite and washed with methanol-ethyl acetate. The filtrate was concentrated under reduced pressure, and the residue was purified by silica gel column chromatography (eluent: chloroform-methanol 30:1) to give Compound 4 (904 mg) as a pale yellow oil.

MS (APCI) 239 [M+H]⁺

Reference Examples 20-2 to 20-11

The following compounds were obtained by reacting and treating in the similar manner to the above Reference Example.

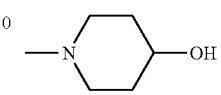

| Reference Examples | R | n | W | MS(APCI) [M + H]+ |
|---|---|---|---|---|
| 20-2 | H | 0 | —NHMe | 195 |
| 20-3 | H | 0 | —NMe₂ | 209 |
| 20-4 | H | 0 | —N(piperidin-4-ol) | 265 |
| 20-5 | H | 0 | —NH(CH₂)₂OH | 225 |
| 20-6 | H | 0 | —NH(CH₂)₃OH | 239 |
| 20-7 | 3-OMe | 0 | —NHMe | 225 |
| 20-8 | H | 1 | —NHMe | 209 |
| 20-9 | H | 1 | —N(Me)(CH₂)₂OH | 253 |
| 20-10 | H | 1 | —NH(CH₂)₂OH | 239 |
| 20-11 | H | 1 | —NH(CH₂)₃OH | 253 |

Reference Example 21

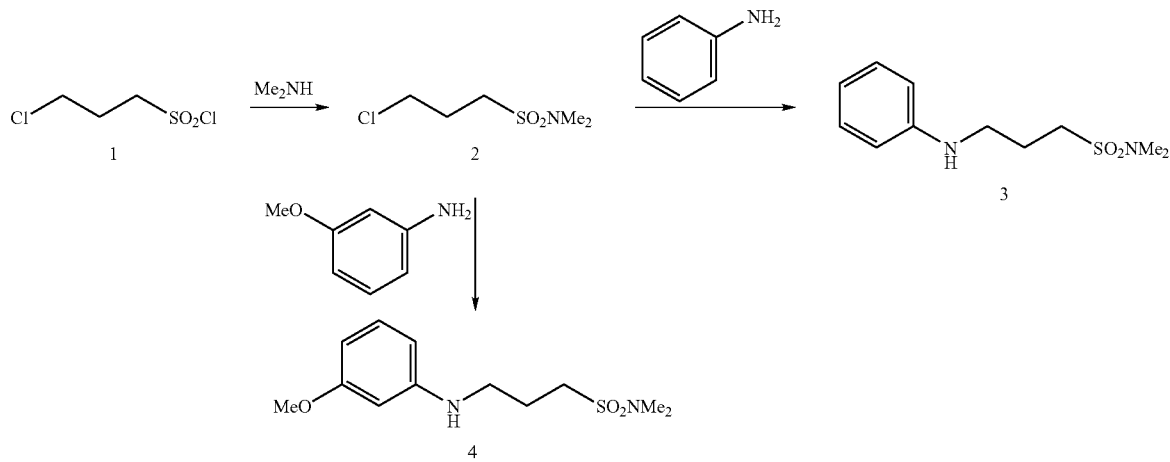

(1) To a solution of Compound 1 (3.0 g) in THF (18 ml) was added dropwise a 2.0N solution of dimethylamine in THF (17.8 ml) under ice cooling. The mixture was stirred for 20 minutes under ice cooling, and then to the reaction mixture was added ice water. The mixture was extracted with ethyl acetate. The extract layers were combined, washed with brine and dried over anhydrous sodium sulfate, and then the solvent was distilled away under reduced pressure. The residue was purified by silica gel column chromatography (eluent: hexane-ethyl acetate 3:1) to give Compound 2 (1642 mg) as a colorless oil.

MS (APCI) 205/203 [M+H]$^+$ (2) To aniline (1.03 g) was added Compound 2 (820 mg), and the mixture was stirred at 120° C. for 5 hours. Then, thereto was added hot toluene (2.2 ml), and then the mixture was left standing to cool. Then, thereto was added ethyl acetate (4.4 ml), and the mixture was stirred for 1 hour. The precipitated insoluble was filtered off, and washed with ethyl acetate. To the filtrate was added an aqueous sodium bicarbonate solution, and the mixture was extracted with ethyl acetate. The extract layers were combined, washed with brine, dried over anhydrous sodium sulfate, and then concentrated under reduced pressure. The residue was purified by silica gel column chromatography (eluent: hexane-ethyl acetate 3:1 to 1:1) to give Compound 3 (141 mg) as a colorless powder.

MS (APCI) 291 [M+H]$^+$ (3) Compound 2 (820 mg) was reacted or treated with m-anisidine (1.36 g) in the similar manner to the above (2) to give Compound 4 (325 mg) as a pale brown oil.

MS (APCI) 351 [M+H]$^+$

Reference Example 22

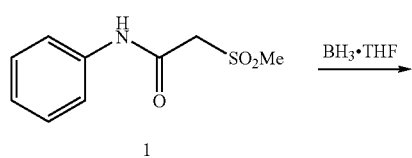

-continued

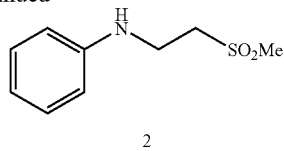

To a solution of Compound 1 (600 mg) in THF (9 ml) was added dropwise 1.17M borane-THF complex (4.81 ml) under ice cooling over 3 minutes. The mixture was stirred at room temperature for 15 hours, and thereto was added additional 1.17M borane-THF complex (2.4 ml). The mixture was stirred at 30° C. for 6 hours under heating. Then, thereto was added 0.5N aqueous sodium hydroxide solution under ice cooling, and the mixture was stirred for 30 minutes, and then extracted with ethyl acetate. The extract layers were combined, washed with brine, dried over anhydrous sodium sulfate, and then concentrated under reduced pressure. The residue was purified by silica gel column chromatography to give Compound 2 (495 mg) as a colorless oil.

MS (APCI) 200 [M+H]$^+$

Reference Example 23

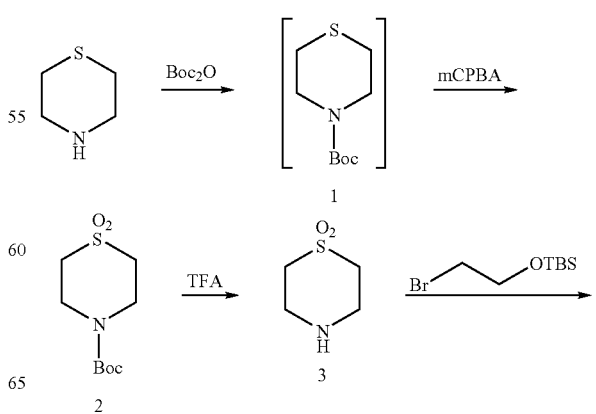

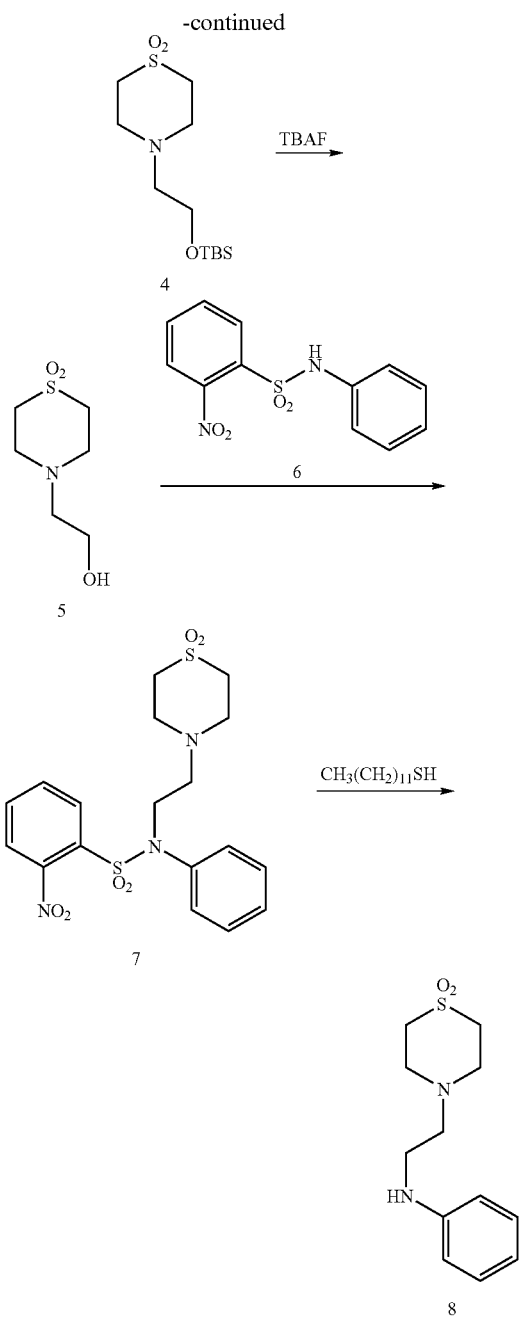

(1) Thiomorpholine (11.55 g) was dissolved in THF (120 ml), and thereto was added triethylamine (13.6 g) and added dropwise a solution of di-t-butyl dicarbonate (25.7 g) in THF (80 ml) under ice cooling over 20 minutes. The mixture was stirred at room temperature for 4 hours, and thereto was added ethyl acetate. The organic layer was washed with an aqueous citric acid solution and brine and dried over anhydrous sodium sulfate, and then the solvent was distilled away under reduced pressure. The residue was purified by silica gel short column chromatography (eluent: chloroform) to give Compound 1 (22.2 g) as a colorless crystal.

(2) Compound 1 (11.1 g) was dissolved in chloroform (220 ml), and thereto was added m-chloroperbenzoic acid (23.6 g) under ice cooling over 30 minutes. The mixture was stirred for 1 hour under ice cooling, allowed to warm up to room temperature, and then stirred for 20 hours. To an aqueous sodium bicarbonate solution was added the reaction mixture, and the mixture was extracted with ethyl acetate. The extract layer was washed with a saturated aqueous sodium bicarbonate solution and a saturated sodium bicarbonate and dried over anhydrous sodium sulfate, and then the solvent was distilled away under reduced pressure. The residue was purified by silica gel column chromatography (eluent: chloroform-methanol 100:1 to 30:1) to give Compound 2 (8.92 g) as a colorless powder.
MS (APCI) 253 $[M+NH_4^+]^+$ (3) Compound 2 (2.00 g) was dissolved in chloroform (8.5 ml), and thereto was added trifluoroacetic acid (8.5 ml) under ice cooling. The mixture was allowed to warm up to room temperature, and then stirred for 30 minutes. The mixture was concentrated under reduced pressure, and thereto was added diisopropyl ether, and the mixture was concentrated under reduced pressure again. The residue was triturated with diisopropyl ether to give Compound 3 (2.10 g) as a colorless powder.

(4) Compound 3 (2.10 g) was suspended in ethanol (43 ml), and thereto was added sodium bicarbonate (2.14 g) at room temperature. After 5 minutes, thereto was added 2-bromoethoxy t-butyldimethylsilane (2.74 ml), and the mixture was stirred at 60° C. for 3 hours. The mixture was allowed to warm up to 80° C. and stirred for 4 days under heating. Then, thereto were added 2-bromoethoxy t-butyldimethylsilane (0.91 ml) and sodium bicarbonate (0.71 g), and the mixture was stirred at 80° C. for additional 1 day under heating. The reaction mixture was cooled, and thereto was added water. The mixture was extracted with ethyl acetate. The organic layers were combined, washed with brine, dried over anhydrous sodium sulfate, and then concentrated under reduced pressure. The residue was purified by silica gel column chromatography (eluent: ethyl acetate-chloroform 1:5) to give Compound 4 (1.94 g) as a colorless crystal.
MS (APCI) 294 $[M+H]^+$ (5) Compound 4 (1.94 g) was suspended in THF (10 ml), and thereto was added a 1N solution of tetrabutylammonium fluoride in THF (9.9 ml, 9.9 mmol) at room temperature. The mixture was stirred for additional 1 hour. The mixture was concentrated under reduced pressure, and then the residue was purified by NH-silica gel column chromatography (eluent: chloroform-methanol 100:1) to give Compound 5 (1.100 g) as a colorless crystal.
MS (APCI) 180 $[M+H]^+$ (6) Compound 5 (2.50 g), Compound 6 (4.66 g) and triphenylphosphine (5.49 g) were dissolved in chloroform (70 ml), and thereto was added dropwise 40% solution of DEAD in toluene (9.10 ml) over 5 minutes under ice cooling. The mixture was allowed to warm up to room temperature, and then stirred for 1 hour. To the reaction mixture was added toluene (5 ml), and the precipitate was filtered off and washed with chloroform-toluene (5:1). The filtrate was concentrated under reduced pressure and purified by silica gel column chromatography (eluent: ethyl acetate-chloroform 1:20) to give Compound 7 (6.07 g) as a colorless foam.
MS (APCI) 440 $[M+H]^+$

[Preparation of Compound 6]
Aniline (4.41 g) was dissolved in THF (90 ml), and thereto was added triethylamine (7.55 ml) and added portionwise 2-nitrobenzenesulfonyl chloride (10.0 g) under ice cooling. The mixture was allowed to warm up to room temperature, and then stirred for 3 hours. The reaction mixture was poured into 0.5N hydrochloric acid, and extracted with ethyl acetate.

The extract layers were combined, washed with brine and dried over anhydrous sodium sulfate, and then the solvent was distilled away under reduced pressure. The residue was crystallized by the addition of diisopropyl ether to give Compound 6 (9.54 g).

MS (ESI) 277 [M−H]⁻

(7) 60% Sodium hydride (829 mg) was suspended in THF (69 ml) under ice cooling, and thereto was added 1-dodecanethiol (5.29 ml). The mixture was stirred at room temperature for 16 hours. Then, thereto was added a solution of Compound 7 (6.07 g) in THF (104 ml) over 10 minutes under ice cooling, and the mixture was stirred at room temperature for 2 hours. Then, thereto was added a suspension of 60% sodium hydride (276 mg) and 1-dodecanethiol (1.98 ml) in THF (23 ml), and the mixture was stirred at room temperature for 1 hour. Then, to the reaction mixture was added an additional suspension of 60% sodium hydride (276 mg) and 1-dodecanethiol (1.98 ml) in THF (23 ml), and the mixture was stirred at room temperature for 1 hour. The reaction mixture was poured into a solution of acetic acid (1.98 ml) in brine (360 ml), and extracted with chloroform. The extract layers were combined, washed with brine and dried over anhydrous sodium sulfate, and then the solvent was distilled away under reduced pressure. The resulting residue was purified by silica gel column chromatography (eluent: chloroform-methanol 200:1 to 70:1), and the resulting oil was crystallized by the addition of hexane to give Compound 8 (2.802 g) as a colorless crystal.

MS (APCI) 255 [M+H]⁺

Reference Example 24-1

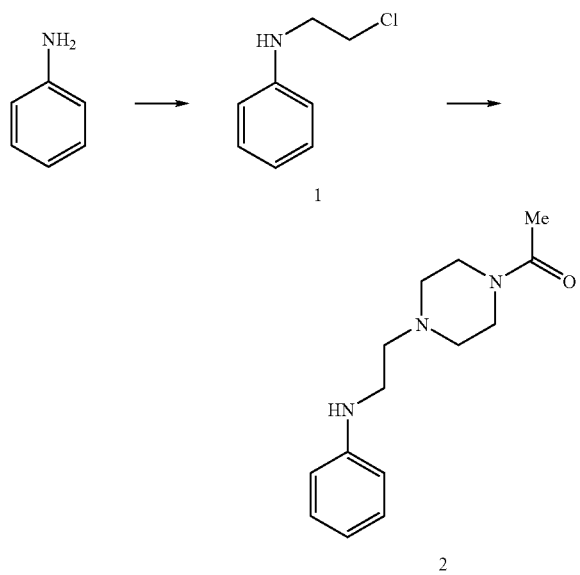

(1) A mixture of 1-bromo-2-chloroethane (14.3 g) and aniline (28.0 g) was stirred at 60-70° C. for 1.5 hours under heating. The reaction mixture was cooled, and thereto was added ethyl acetate (80 ml). The precipitated solid was filtered off. The filtrate was concentrated under reduced pressure, and the residue was purified by silica gel column chromatography (chloroform-hexane 1:1 to 2:3) to give Compound 1 (3.40 g) as a pale brown oil.

MS (APCI) 156/158 [M+H]⁺

(2) Compound 1 (202 mg) and 1-acetylpiperazine (416 mg) were dissolved in acetonitrile (3.9 ml), and thereto were added potassium carbonate (359 mg) and sodium iodide (19 mg). The mixture was stirred at 95° C. for 24 hours under heating. The reaction solution was cooled, and thereto was added water. The mixture was extracted with ethyl acetate. The extract layers were combined, washed with brine, dried over anhydrous sodium sulfate, and then concentrated under reduced pressure. The residue was purified by silica gel column chromatography (eluent: chloroform-methanol 99:1 to 91:9) to give Compound 2 (251 mg) as a colorless oil.

MS (APCI) 248 [M+H]⁺

Reference Example 24-2

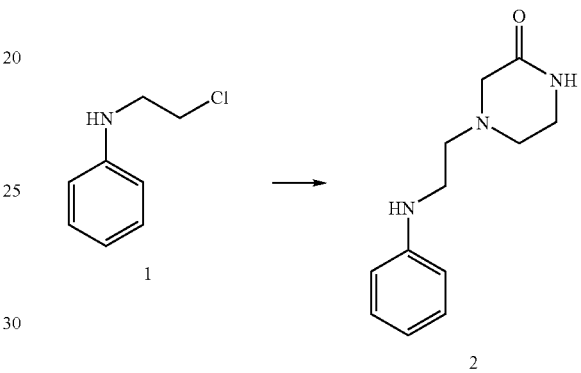

Compound 1 (300 mg) and 2-piperazinone (483 mg) were dissolved in acetonitrile (6 ml), and thereto were added potassium carbonate (533 mg) and sodium iodide (29 mg). The mixture was stirred at 90° C. for 3 days under heating. The reaction solution was cooled, and thereto was added water. The mixture was extracted with ethyl acetate. The extract layers were combined, washed with brine, dried over anhydrous sodium sulfate, and then concentrated under reduced pressure. The residue was purified by silica gel column chromatography (eluent: chloroform-methanol 98:2 to 90:10) to give Compound 1 (239 mg) as a colorless oil.

MS (APCI) 220 [M+H]⁺

Reference Example 24-3

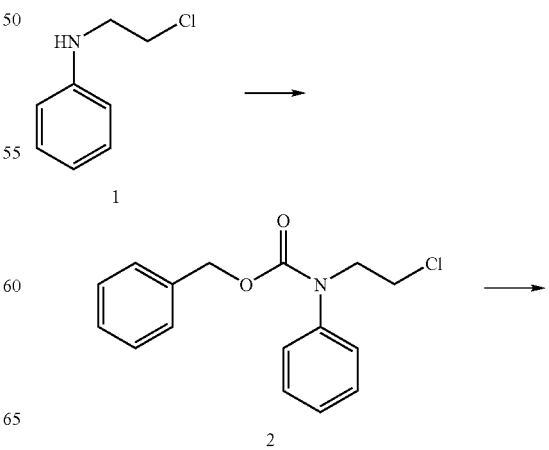

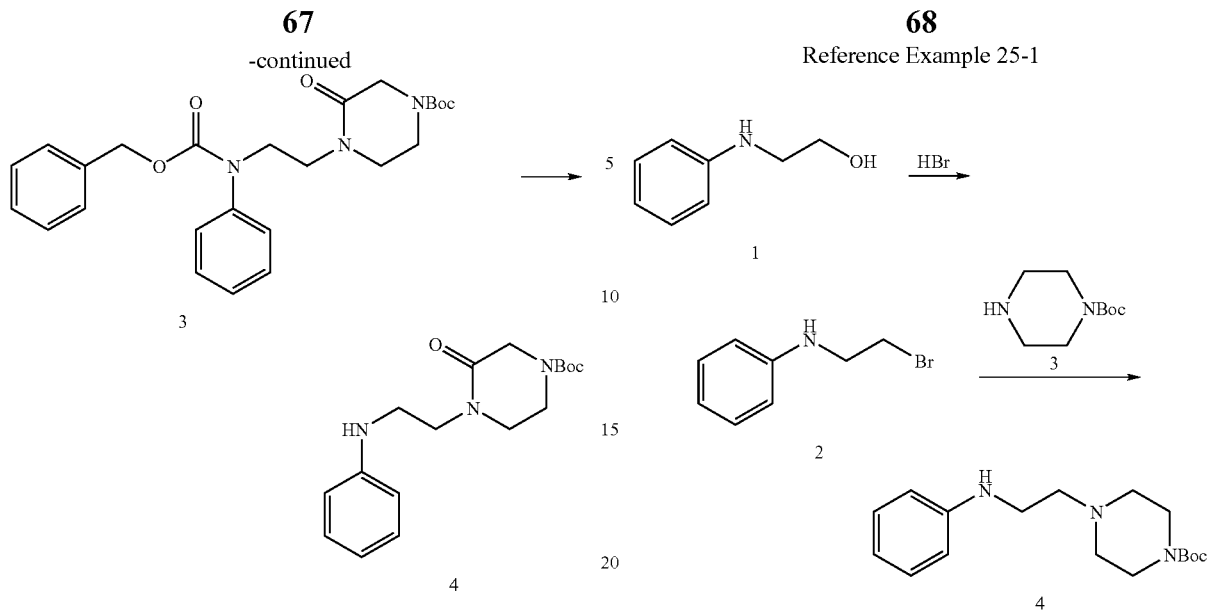

3

4

Reference Example 25-1

(1) Compound 1 (1.0 g) was dissolved in chloroform (20 ml), and thereto was added triethylamine (1.35 ml) and added dropwise benzyl chloroformate (1.38 g) under ice cooling. Then, thereto was added pyridine (783 μl) and added dropwise benzyl chloroformate (1.73 g), and the mixture was allowed to warm up slowly to room temperature and stirred at the same temperature. The reaction mixture was concentrated under reduced pressure, and to the residue was added water. The mixture was extracted with ethyl acetate. The extract layers were combined, washed with hydrochloric acid and brine and dried over anhydrous magnesium sulfate, and then the solvent was distilled away under reduced pressure. The residue was purified by silica gel column chromatography (eluent: hexane-ethyl acetate 9:1) to give Compound 2 (1.2846 g) as a pale yellow oil.

MS (APCI) 290/292 [M+H]$^+$ (2) Sodium hydride (144 mg) was suspended in DMSO (6 ml), and stirred at 70° C. The suspension was cooled to room temperature, and thereto was added a solution of 1-t-butoxycarbonyl-3-oxopiperazine (600 mg) in DMSO (10 ml) and added dropwise a solution of Compound 2 (956 mg) in DMSO (4 ml). The mixture was stirred at room temperature for 3 hours, and then stirred at 50° C. for 2 hours. To the reaction mixture was added water, and the mixture was extracted with ethyl acetate. The extract layers were combined, washed with brine and dried over anhydrous magnesium sulfate, and then the solvent was distilled away under reduced pressure. The residue was purified by silica gel column chromatography (eluent: hexane-ethyl acetate 1:1 to 1:2) to give Compound 3 (505.9 mg) as a colorless amorphous powder.

MS (APCI) 454 [M+H]$^+$ (3) Compound 3 (150 mg) was dissolved in methanol (3 ml), and thereto was added 10% palladium carbon (75 mg). The mixture was catalytically hydrogenated under hydrogen atmosphere at room temperature under ambient pressure. The catalyst was filtered off, and the filtrate was concentrated under reduced pressure. The residue was purified by silica gel column chromatography (eluent: hexane-ethyl acetate 1:1 to 1:4) to give Compound 4 (39.9 mg) as a colorless oil.

MS (APCI) 320 [M+H]$^+$ (1) Compound 1 (10.0 g) was dissolved in 48% hydrogen bromide water (140 ml), and stirred at 140° C. for 15 hours under heating. The reaction solution was cooled to room temperature, and the solvent was distilled away. To the residue was added diethyl ether, and slowly added an aqueous sodium bicarbonate solution with stirring under ice cooling. The mixture was separated, and the organic layer was washed with brine and dried over anhydrous magnesium sulfate. The solvent was distilled away under reduced pressure, and the resulting residue was purified by silica gel column chromatography (eluent: n-hexane-ethyl acetate 9:1) to give Compound 2 (11.6 g) as a pale yellow oil.

MS (APCI) 200/202 [M+H]$^+$ (2) Compound 2 (5.63 g) was dissolved in acetonitrile (150 ml), and thereto were added potassium carbonate (9.75 g), sodium iodide (0.42 g) and Compound 3 (7.86 g). The mixture was stirred at 90° C. for 5 hours. The reaction solution was cooled to room temperature, and the solvent was distilled away. Then, thereto was added brine, and the mixture was extracted with ethyl acetate. The extract layer was dried over anhydrous magnesium sulfate, and the solvent was distilled away under reduced pressure. The residue was purified by silica gel column chromatography (eluent: n-hexane-ethyl acetate 20:1 to 3:2) to give Compound 4 (7.69 g) as a pale yellow oil.

MS (APCI) 306 [M+H]$^+$

Reference Example 25-2

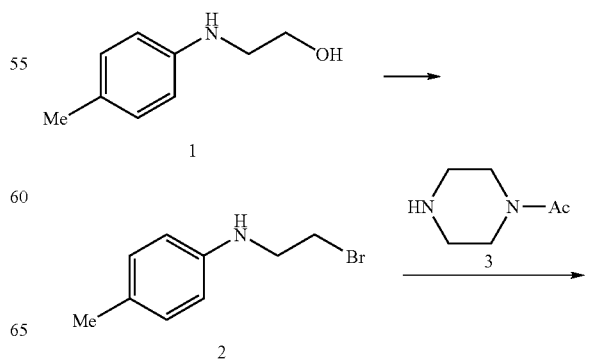

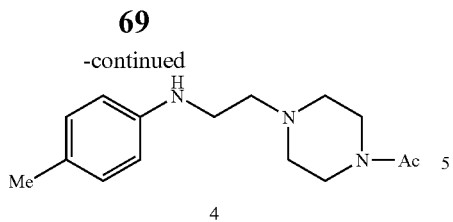

4

(1) To a solution of Compound 1 (475 mg) in acetonitrile (8 ml) was added triphenylphosphine (1.24 g). Then, thereto was added dropwise a solution of carbon tetrabromide (1.56 g) in acetonitrile (8 ml) with stirring under ice cooling. The mixture was stirred at room temperature for 1 hour, and the solvent was distilled away. To the residue was added a saturated aqueous sodium bicarbonate solution, and the mixture was extracted with ethyl acetate. The organic layer was washed with brine, and dried over anhydrous magnesium sulfate. The solvent was distilled away under reduced pressure, and the resulting residue was purified by silica gel column chromatography (eluent: n-hexane-ethyl acetate 20:1 to 5:1) to give Compound 2 (456 mg) as a pale yellow oil.

MS (APCI) 214/216 [M+H]$^+$ (2) Compound 2 (349 mg) was dissolved in acetonitrile (8 ml), and thereto were added potassium carbonate (452 mg), sodium iodide (24 mg) and Compound 3 (461 mg). The mixture was stirred at 75° C. for 5 hours. The reaction solution was cooled to room temperature, and the solvent was distilled away. To the residue was added a saturated aqueous sodium bicarbonate solution, and the mixture was extracted with ethyl acetate. The organic layer was washed with brine, and dried over anhydrous magnesium sulfate. The solvent was distilled away under reduced pressure, and the resulting residue was purified by silica gel column chromatography (eluent: methanol-chloroform 0:1 to 1:10) to give Compound 4 (168 mg) as a pale yellow oil.

MS (APCI) 262 [M+H]$^+$

The following compounds were obtained by reacting and treating in the similar manner to the above Reference Example.

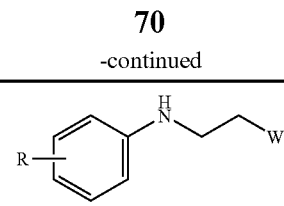

| Reference Examples | R | W | MS(APCI) [M + H]$^+$ |
|---|---|---|---|
| 25-3 | 3-Me | —N(piperazine)N—Ac | 262 |
| 25-4 | 3-Cl | —N(piperazine)N—Ac | 282/284 |
| 25-5 | H | pyrrolidin-3-yl NHBoc | 306 |
| 25-6 | H | (3-F)-pyrrolidin-1-yl | 209 |
| 25-7 | H | 3-(SO$_2$Me)-pyrrolidin-1-yl | 269 |
| 25-8 | H | 4-(SO$_2$Me)-piperidin-1-yl | 283 |
| 25-9 | H | 3-Me-piperazin-1-yl-N'-Ac | 262 |
| 25-10 | H | —N(Me)(CH$_2$)$_2$NHMe | 208 |

Reference Example 26-1

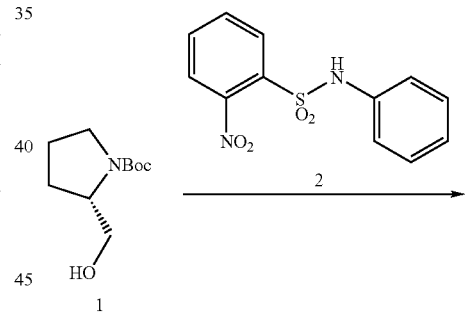

(1) Compound 1 (1.041 g), Compound 2 (1.20 g) and triphenylphosphine (1.70 g) were dissolved in chloroform (21 ml), and thereto was added dropwise a 40% solution of DEAD in toluene (2.81 ml) over 3 minutes under ice cooling. The mixture was allowed to warm up to room temperature, and the mixture was stirred for 17 hours. The reaction mixture was concentrated under reduced pressure, and thereto was added hexane. The precipitate was filtered off and washed with hexane-chloroform (1:1). The filtrate was concentrated under reduced pressure, and the residue was purified by silica gel column chromatography (eluent: hexane-ethyl acetate 4:1 to 3:1) to give Compound 3 (1055 mg) as a colorless oil.

MS (APCI) 479 [M+H]$^+$ (2) 60% Sodium hydride (52 mg) was suspended in THF (5.5 ml), and thereto was added 1-dodecanethiol (324 μl) under ice cooling. The mixture was allowed to warm up to room temperature, and stirred for 30 minutes. Then, thereto was added a solution of Compound 3 (500 mg) in THF (5.5 ml) under ice cooling, and the mixture was allowed to warm up to room temperature and then stirred for 19 hours. Then, to the reaction mixture was added a suspension of 60% sodium hydride (13 mg) and 1-dodecanethiol (91 μl) in THF (3 ml), and the mixture was stirred at room temperature for 4 hours. To the reaction mixture was added brine, and the mixture was extracted with ethyl acetate. The extract layers were combined and dried over anhydrous sodium sulfate, and then the solvent was distilled away under reduced pressure. The residue was purified by silica gel column chromatography (eluent: hexane-ethyl acetate 5:1) to give Compound 4 (206 mg) as a colorless oil.

MS (APCI) 277 [M−H]$^+$

Reference Example 26-2

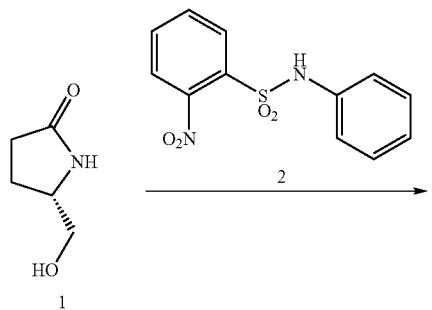

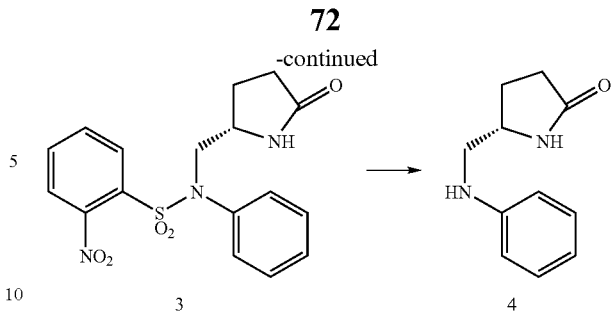

(1) Compound 1 (150 mg), Compound 2 (300 g) and triphenylphosphine (425 g) were dissolved in chloroform (5.4 ml), and thereto was added dropwise a 40% solution of DEAD in toluene (0.704 ml) over 1 minute under ice cooling. The mixture was allowed to warm up to room temperature, and stirred for 4 hours. The reaction mixture was concentrated under reduced pressure, and thereto was added hexane. The precipitate was filtered off and washed with hexane-chloroform (1:1). The filtrate was concentrated under reduced pressure, and the residue was purified by silica gel column chromatography (eluent: chloroform-ethyl acetate 1:1 to ethyl acetate) to give Compound 3 (395 mg) as a colorless foam.

MS (APCI) 376 [M+H]$^+$ (2) 60% Sodium hydride (63 mg) was dissolved in THF (10.5 ml), and thereto was added 1-dodecanethiol (402 n1) under ice cooling. The mixture was allowed to warm up to room temperature and stirred for 30 minutes. Then, thereto was added a solution of Compound 3 (394 mg) in THF (2 ml) under ice cooling, and the mixture was allowed to warm up to room temperature and then stirred for 2 hours. To the reaction mixture was added brine, and the mixture was extracted with ethyl acetate. The extract layers were combined and dried over anhydrous sodium sulfate, and then the solvent was distilled away under reduced pressure. The residue was purified by silica gel column chromatography (eluent: ethyl acetate to ethyl acetate-methanol 1% to 3% gradient) to give Compound 4 (334 mg) as a colorless amorphous powder.

MS (APCI) 461 [M+H]$^+$

The following tables show chemical structures and property data of the above Example compounds.

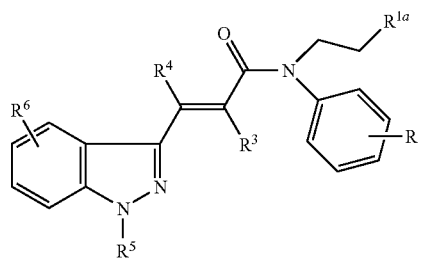

| Examples | $R^{1a}$ | R | $R^3$ | $R^4$ | $R^5$ | $R^6$ | Salts | MS(APCI) [M + H]$^+$ |
|---|---|---|---|---|---|---|---|---|
| 1-1 | —NHAc | H | H | H | H | H | | 349 |
| 1-2 | —NHAc | H | H | Me | H | H | | 363 |
| 1-3 | —N(Me)COOMe | H | H | H | H | H | | 379 |
| 1-4 | —NHAc | H | Me | H | H | H | | 363 |
| 1-5 | —NHCONHEt | H | H | H | H | H | | 378 |
| 1-6 | —NHCOPr | H | H | H | H | H | | 377 |
| 1-7 | —NHCOOEt | H | H | H | H | H | | 379 |
| 1-8 | —NHAc | 4-Me | H | H | H | H | | 363 |
| 1-9 | —NHSO$_2$Me | H | H | H | H | H | | 385 |
| 1-10 | —NHAc | 4-OMe | H | H | H | H | | 379 |

-continued

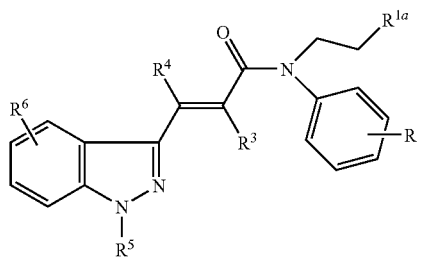

| Examples | R$^{1a}$ | R | R$^3$ | R$^4$ | R$^5$ | R$^6$ | Salts | MS(APCI) [M + H]$^+$ |
|---|---|---|---|---|---|---|---|---|
| 1-11 | —NHAc | 3-Me | H | H | H | H | | 363 |
| 1-12 | —NHAc | 3-OMe | H | H | H | H | | 379 |
| 1-13 | —NHAc | 2-OMe | H | H | H | H | | 379 |
| 1-14 | —NHAc | 2-Me | H | H | H | H | | 363 |
| 1-15 | —NHAc | 2-F | H | H | H | H | | 367 |
| 1-16 | —NHAc | 4-F | H | H | H | H | | 367 |
| 1-17 | —NHCOPh | H | H | H | H | H | | 411 |
| 1-18 | —NHCOCH$_2$Ph | H | H | H | H | H | | 425 |
| 1-19 | —NHCOCH$_2$OMe | H | H | H | H | H | | 379 |
| 1-20 | —N(Me)Ac | H | H | H | H | H | | 363 |
| 1-21 | —NHCHO | H | H | H | H | H | | 335 |
| 1-22 | —NHCOOMe | H | H | H | H | H | | 365 |
| 1-23 | —NHCOOPr | H | H | H | H | H | | 393 |
| 1-24 | —NHAc | 3-CF$_3$ | H | H | H | H | | 417 |
| 1-25 | —NHAc | 3-OCF$_3$ | H | H | H | H | | 433 |
| 1-26 | —NHAc | 3-OCHF$_2$ | H | H | H | H | | 415 |
| 1-27 | ![nicotinamide] | H | H | H | H | H | | 412 |
| 1-28 | —NHSO$_2$NHMe | H | H | H | H | H | | 400 |
| 1-29 | —NHAc | 3-CH$_2$COOMe | H | H | H | H | | 421 |
| 1-30 | —NHCOO(CH$_2$)$_2$OMe | H | H | H | H | H | | 409 |
| 1-31 | ![tetrahydrofuran amide] | H | H | H | H | H | | 405 |
| 1-32 | —NHCOCH$_2$CN | H | H | H | H | H | | 374 |
| 1-33 | —NHCOO(CH$_2$)$_2$OH | H | H | H | H | H | | 395 |
| 1-34 | —NHCOCH$_2$NMe$_2$ | H | H | H | H | H | | 392 |
| 1-35 | ![morpholine amide] | H | H | H | H | H | | 434 |
| 1-36 | ![piperidine-3-COOtBu amide] | H | H | H | H | H | | 518 |
| 1-37 | ![piperidine-4-COOtBu amide] | H | H | H | H | H | | 518 |

-continued

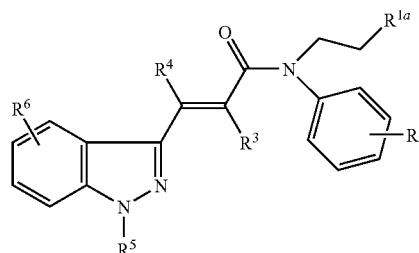

| Examples | R1a | R | R3 | R4 | R5 | R6 | Salts | MS(APCI) [M + H]+ |
|---|---|---|---|---|---|---|---|---|
| 1-38 | *N-methyl-1-methylpyrrolidine-2-carboxamide* | H | H | H | H | H | | 418 |
| 1-39 | —NHCOCH2N(Me)COOtBu | H | H | H | H | H | | 478 |
| 1-40 | —NHCONHMe | H | H | H | H | H | | 364 |
| 1-41 | —NHSO2NMe2 | H | H | H | H | H | | 414 |
| 1-42 | —NHAc | 3,5-di OMe | H | H | H | H | | 409 |
| 1-43 | —NHAc | 2,5-di OMe | H | H | H | H | | 409 |
| 1-44 | —NHAc | 2,3-di OMe | H | H | H | H | | 409 |
| 1-45 | —NHCONMe2 | H | H | H | H | H | | 378 |
| 1-46 | —NHCONH(CH2)2OMe | H | H | H | H | H | | 408 |
| 1-47 | —NHCOCH2N(Me)Ac | H | H | H | H | H | | 420 |
| 1-48 | *N-methyl-4-hydroxypiperidine-1-carboxamide* | H | H | H | H | H | | 434 |
| 1-49 | —N(Et)CHO | H | H | H | H | H | | 363 |
| 1-50 | —N(Et)COOMe | H | H | H | H | H | | 393 |
| 1-51 | —N(Et)CONHEt | H | H | H | H | H | | 406 |
| 1-52 | —NHAc | 3-OMe-4-F | H | H | H | H | | 397 |
| 1-53 | —NHAc | 3-Me-4-OMe | H | H | H | H | | 393 |
| 1-54 | —NHCOCH2N(Me)(CH2)2OMe | H | H | H | H | H | | 436 |
| 1-55 | *N-methyl-1-cyanocyclopropanecarboxamide* | H | H | H | H | H | | 400 |
| 1-56 | —NHAc | 2-Me-3-OMe | H | H | H | H | | 393 |
| 1-57 | *N-methyl-2-(pyrrolidin-1-yl)acetamide* | H | H | H | H | H | | 418 |
| 1-58 | —NHCOCH2Ph | H | H | H | Et | H | | 453 |
| 1-59 | —NHCOCH(Me)CN | H | H | H | H | H | | 388 |
| 1-60 | —NHCOiPr | H | H | H | Et | H | | 405.27* |
| 1-61 | —NHCOCH2NMe2 | H | H | H | Et | H | | 420.27* |
| 1-62 | *N-methyltetrahydrofuran-2-carboxamide* | H | H | H | Et | H | | 433.26* |
| 1-63 | —NHCOC(Me)2NMe2 | H | H | H | H | H | | 420 |
| 1-64 | —NHCO(CH2)2CN | H | H | H | H | H | | 388 |

-continued

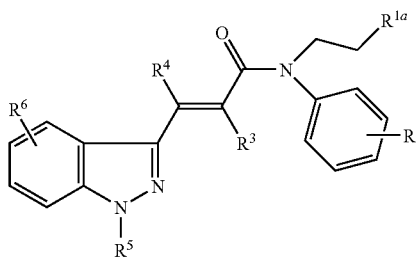

| Examples | R$^{1a}$ | R | R$^3$ | R$^4$ | R$^5$ | R$^6$ | Salts | MS(APCI) [M + H]$^+$ |
|---|---|---|---|---|---|---|---|---|
| 1-65 | | H | H | H | H | H | | 462 |
| 1-66 | | H | H | H | H | H | | 448 |
| 1-67 | —NHCOC(Me)$_2$CN | H | H | H | H | H | | 402 |
| 1-68 | ![](3,3-difluoropyrrolidine-CH2CONHMe) | H | H | H | H | H | | 454 |
| 1-69 | ![](2,6-dimethylmorpholine-CH2CONHMe) | H | H | H | H | H | | 462 |
| 1-70 | ![](N-CH2CF3 prolinamide) | H | H | H | H | H | | 486 |
| 1-71 | —NHCOCH$_2$N(Me)COOMe | H | H | H | H | H | | 436 |
| 1-72 | —N(Me)COCH$_2$OMe | H | H | H | H | H | | 393 |
| 1-73 | —N(Me)COCH$_2$CN | H | H | H | H | H | | 388 |
| 1-74 | —N(Me)COCH$_2$NMe$_2$ | H | H | H | H | H | | 406 |
| 1-75 | —N(Me)CONHEt | H | H | H | H | H | | 392 |
| 1-76 | —N(Me)COO(CH$_2$)$_2$OMe | H | H | H | H | H | | 423 |
| 1-77 | —N(Me)CHO | H | H | H | H | H | | 349 |
| 1-78 | —NHAc | 3-OMe | H | Me | H | H | | 393 |
| 1-79 | —N(Me)COCH(Me)CN | H | H | H | H | H | | 402 |
| 1-80 | —NHCON(Me)(CH$_2$)$_2$OMe | H | H | H | H | H | | 422 |
| 1-81 | | H | H | H | H | H | | 420 |
| 1-82 | —NHCONEt$_2$ | H | H | H | H | H | | 406 |

-continued

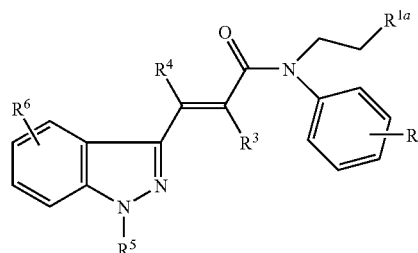

| Examples | R¹ᵃ | R | R³ | R⁴ | R⁵ | R⁶ | Salts | MS(APCI) [M + H]⁺ |
|---|---|---|---|---|---|---|---|---|
| 1-83 | (methylcarbamoyl-pyrrolidine) | H | H | H | H | H | | 404 |
| 1-84 | —NHCHO | 3-OMe | H | H | H | H | | 365 |
| 1-85 | —NHAc | 3-OMe | Me | H | H | H | | 393 |
| 1-86 | —NHCOO(CH₂)₂OMe | 3-OMe | H | H | H | H | | 439 |
| 1-87 | —NHCOCH₂OMe | 3-OMe | H | H | H | H | | 409 |
| 1-88 | —NHCON(Me)(CH₂)₂OH | H | H | H | H | H | | 408 |
| 1-89 | —NHCOCH₂N(Me)(CH₂)₂CN | H | H | H | H | H | | 431.25* |
| 1-90 | —NHCOCH₂N(Me)(CH₂)₂SO₂Me | H | H | H | H | H | | 484.20* |
| 1-91 | (methylcarbamoylmethyl-3-fluoropyrrolidine) | H | H | H | H | H | | 436.27* |
| 1-92 | (methylcarbamoylmethyl-3-cyanopyrrolidine) | H | H | H | H | H | | 443.26* |
| 1-93 | —NHCHO | H | H | Me | H | H | | 349 |
| 1-94 | —NHCONMe₂ | 3-OMe | H | H | H | H | | 408 |
| 1-95 | —NHCOCH₂CN | 3-OMe | H | H | H | H | | 404 |
| 1-96 | —NHCOCH(Me)CN | 3-OMe | H | H | H | H | | 418 |
| 1-97 | (methylcarbamoylmethyl-morpholine) | 3-OMe | H | H | H | H | | 464 |
| 1-98 | (methylcarbamoyl-dimethyl-morpholine) | H | H | H | H | H | | 462 |
| 1-99 | (methylcarbamoyl-N-methylmorpholine) | H | H | H | H | H | | 434 |
| 1-100 | —NHCOCH₂N(Me)COOMe | 3-OMe | H | H | H | H | | 466 |
| 1-101 | (methylcarbamoyl-cyclopropane) | H | H | H | H | H | | 375.05* |
| 1-102 | —NHCOCH₂OEt | H | H | H | H | H | | 393.06* |

-continued

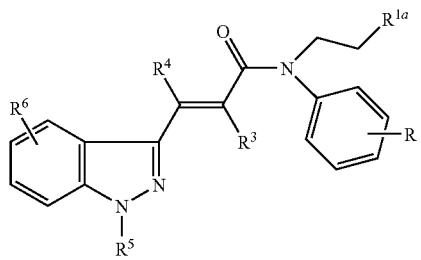

| Examples | R$^{1a}$ | R | R$^3$ | R$^4$ | R$^5$ | R$^6$ | Salts | MS(APCI) [M + H]$^+$ |
|---|---|---|---|---|---|---|---|---|
| 1-103 | (N-methylcarboxamide-2-pyridyl) | H | H | H | H | H | | 412.02* |
| 1-104 | (N-methylcarboxamide-4-pyridyl) | H | H | H | H | H | | 412.02* |
| 1-105 | —NHCO(CH$_2$)$_2$OMe | H | H | H | H | H | | 393.06* |
| 1-106 | —NHCOCH$_2$SO$_2$Me | H | H | H | H | H | | 426.95* |
| 1-107 | (S)-N-methyl-2-hydroxypropanamide | H | H | H | H | H | | 379.02* |
| 1-108 | (R)-N-methyl-2-hydroxypropanamide | H | H | H | H | H | | 379.02* |
| 1-109 | (S)-N-methyl-2-methoxypropanamide | H | H | H | H | H | | 393.03* |
| 1-110 | (R)-N-methyl-2-methoxypropanamide | H | H | H | H | H | | 393.00* |
| 1-111 | —NHCOCONHMe | H | H | H | H | H | | 392 |
| 1-112 | —NHCOOMe | H | Me | H | H | H | | 379 |
| 1-113 | —NHCOCONMe$_2$ | H | H | H | H | H | | 406 |
| 1-114 | —NHCON(Me)Et | H | H | H | H | H | | 392 |
| 1-115 | (N-methylmorpholine-4-carboxamide) | 3-OMe | H | H | H | H | | 450 |
| 1-116 | —NHCOCH$_2$CN | H | H | Me | H | H | | 388 |
| 1-117 | —NHCONMe$_2$ | H | H | Me | H | H | | 392 |

-continued

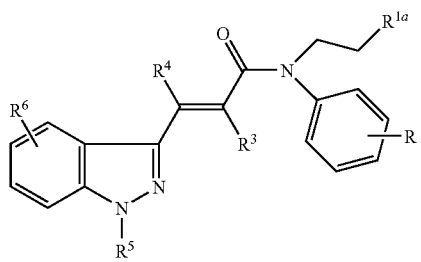

| Examples | $R^{1a}$ | R | $R^3$ | $R^4$ | $R^5$ | $R^6$ | Salts | MS(APCI) [M + H]+ |
|---|---|---|---|---|---|---|---|---|
| 1-118 | (N-methylcarbamoyl morpholine) | H | H | Me | H | H | | 434 |

*MS(ESI)[M + H]+

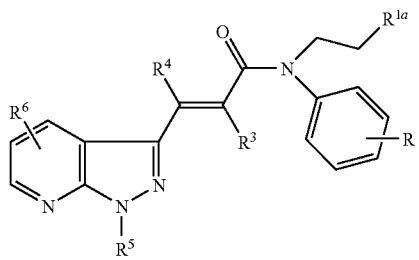

| Examples | $R^{1a}$ | R | $R^3$ | $R^4$ | $R^5$ | $R^6$ | Salts | MS(APCI) [M + H]+ |
|---|---|---|---|---|---|---|---|---|
| 2-1 | —NHCOCH$_2$OMe | H | H | H | H | H | | 380 |
| 2-2 | —NHCOOMe | H | H | H | H | H | | 366 |
| 2-3 | —NHCOOMe | 3-Me | H | H | H | H | | 380 |
| 2-4 | —NHCOOMe | 4-Me | H | H | H | H | | 380 |
| 2-5 | —NHCOOMe | 2-Me | H | H | H | H | | 380 |
| 2-6 | —NHCOEt | H | H | H | H | H | | 364.31* |
| 2-7 | —NHCO$^i$Pr | H | H | H | H | H | | 378.31* |
| 2-8 | (tetrahydrofuran-2-carboxamide) | H | H | H | H | H | | 406.28* |
| 2-9 | ((S)-2-methoxypropanamide) | H | H | H | H | H | | 394.3* |
| 2-10 | ((R)-2-methoxypropanamide) | H | H | H | H | H | | 394.3* |
| 2-11 | —NHCOPh | H | H | H | H | H | | 412.26* |
| 2-12 | —N(Me)COOMe | H | H | H | H | H | | 380 |
| 2-13 | —NHCOOEt | H | H | H | H | H | | 380 |
| 2-14 | —NHCOCH$_2$Ph | H | H | H | H | H | | 426 |
| 2-15 | —NHCOO(CH$_2$)$_2$OMe | H | H | H | H | H | | 410 |

-continued

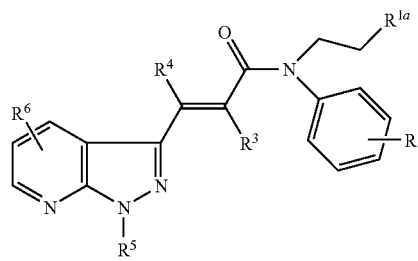

| Examples | R1a | R | R3 | R4 | R5 | R6 | Salts | MS(APCI) [M + H]+ |
|---|---|---|---|---|---|---|---|---|
| 2-16 | ![tetrahydrofuran-2-carboxamide] | H | H | H | H | H | | 406 |
| 2-17 | —NHCOCH2OEt | H | H | H | H | H | | 394 |
| 2-18 | ![2-methoxypropanamide] | H | H | Me | H | H | | 408 |
| 2-19 | ![1-methylpyrrolidine-2-carboxamide] | H | H | H | H | H | | 419 |
| 2-20 | ![cyclobutanecarboxamide] | H | H | H | H | H | | 390 |
| 2-21 | ![1-cyanocyclopropanecarboxamide] | H | H | H | H | H | | 401 |
| 2-22 | —NHCOC(Me)2CN | H | H | H | H | H | | 403 |
| 2-23 | —NHCOCH(Me)CN | H | H | H | H | H | | 389 |
| 2-24 | —NHSO2iPr | H | H | H | H | H | | 414 |
| 2-25 | ![2-methoxypropanamide] | Me | 2-F | H | H | H | | 412 |
| 2-26 | ![2-methoxypropanamide] | 3-F | H | H | H | H | | 412 |
| 2-27 | ![2-methoxypropanamide] | 2-Cl | H | H | H | H | | 428/430 |

-continued

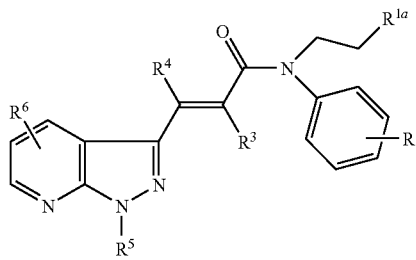

| Examples | R1a | R | R3 | R4 | R5 | R6 | Salts | MS(APCI) [M + H]+ |
|---|---|---|---|---|---|---|---|---|
| 2-28 | (S)-NHC(O)CH(OMe)Me | 3-Cl | H | H | H | H | | 428/430 |
| 2-29 | (S)-NHC(O)CH(OMe)Me | 4-Cl | H | H | H | H | | 428/430 |
| 2-30 | (S)-NHC(O)CH(OMe)Me | 3-OMe | H | H | H | H | | 424 |
| 2-31 | NHC(O)CF(Me) | H | H | H | H | H | | 382 |
| 2-32 | —NHCOOMe | H | H | Me | H | H | | 380 |
| 2-33 | NHC(O)CH(OMe)iPr | H | H | H | H | H | | 422 |
| 2-34 | —NHCOC(Me)$_2$OMe | H | H | H | H | H | | 408 |
| 2-35 | —NHCOCH(Me)OEt | H | H | H | H | H | | 408 |
| 2-36 | —NHSO$_2$Me | H | H | Me | H | H | | 400 |
| 2-37 | —NHSO$_2$Et | H | H | Me | H | H | | 414 |
| 2-38 | —NHSO$_2$(CH$_2$)$_2$OMe | H | H | Me | H | H | | 444 |
| 2-39 | —NHSO$_2$(CH$_2$)$_3$OMe | H | H | Me | H | H | | 458 |
| 2-40 | NHSO$_2$-(tetrahydropyran-4-yl) | H | H | Me | H | H | | 470 |
| 2-41 | —NHCOO(CH$_2$)$_2$OMe | H | H | Me | H | H | | 424 |
| 2-42 | —NHCOO(CH$_2$)$_2$OH | H | H | Me | H | H | | 410 |
| 2-43 | NHC(O)-(1-cyanocyclopropyl) | H | H | Me | H | H | | 415 |

-continued

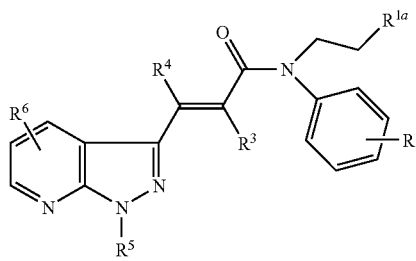

| Examples | R$^{1a}$ | R | R$^3$ | R$^4$ | R$^5$ | R$^6$ | Salts | MS(APCI) [M + H]+ |
|---|---|---|---|---|---|---|---|---|
| 2-44 | (N-methyl cyclopropanecarboxamide) | H | H | Me | H | H | | 389 |
| 2-45 | —NHCOCH$_2$NMe$_2$ | H | H | Me | H | H | | 407 |
| 2-46 | (N-methyl 2-fluoropropanamide) | H | H | Me | H | H | | 396 |
| 2-47 | —NHCOC(Me)$_2$CN | H | H | Me | H | H | | 417 |
| 2-48 | —NHCO$^i$Pr | H | H | Me | H | H | | 392 |
| 2-49 | —NHCOCH$_2$OEt | H | H | Me | H | H | | 408 |
| 2-50 | (N-methyl tetrahydrofuran-2-carboxamide) | H | H | Me | H | H | | 420 |
| 2-51 | (N-methyl 2-methoxypropanamide) | H | H | Me | H | H | | 408 |
| 2-52 | —NHCOCH(Me)CN | H | H | Me | H | H | | 403 |
| 2-53 | (N-methyl 1-methylpyrrolidine-2-carboxamide) | H | H | Me | H | H | | 433 |
| 2-54 | (N-methyl isoxazolidine-4-carboxamide) | H | H | Me | H | H | | 420 |
| 2-55 | (N-methyl tetrahydrofuran-3-yl carbamate) | H | H | Me | H | H | | 436 |
| 2-56 | (N-methyl 2-morpholinoacetamide) | H | H | Me | H | H | | 449 |

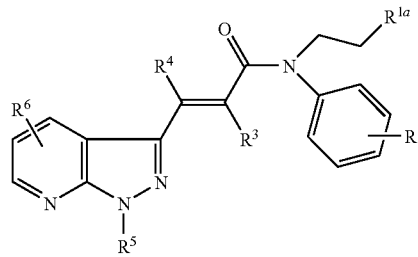
| Examples | R$^{1a}$ | R | R$^3$ | R$^4$ | R$^5$ | R$^6$ | Salts | MS(APCI) [M + H]+ |
|---|---|---|---|---|---|---|---|---|
| 2-57 | —NHCO$^i$Pr | 2-F | H | Me | H | H | | 410 |
| 2-58 | 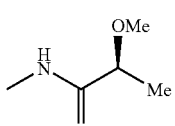 | 3-OMe | H | Me | H | H | | 438 |
| 2-59 | 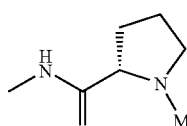 | 2-F | H | Me | H | H | | 451 |
*: MS (ESI) [M + H]$^+$
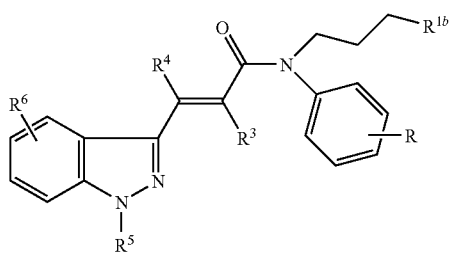
| Examples | R$^{1b}$ | R | R$^3$ | R$^4$ | R$^5$ | R$^6$ | Salts | MS(APCI) [M + H]$^+$ |
|---|---|---|---|---|---|---|---|---|
| 3-1 | —NHAc | H | H | H | H | H | | 363 |
| 3-2 | —NHCOO(CH$_2$)$_2$OMe | H | H | H | H | H | | 423 |
| 3-3 | —NHCOCH$_2$CN | H | H | H | H | H | | 388 |
| 3-4 | —NHCHO | H | H | H | H | H | | 349 |
| 3-5 |  | H | H | H | H | H | | 448 |
| 3-6 | —NHCOCH$_2$NMe$_2$ | H | H | H | H | H | | 406 |
| 3-7 | —NHCOOMe | H | H | Me | H | H | | 393 |

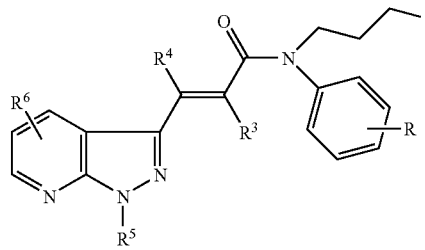

| Examples | R$^{1b}$ | R | R$^3$ | R$^4$ | R$^5$ | R$^6$ | Salts | MS(APCI) [M + H]$^+$ |
|---|---|---|---|---|---|---|---|---|
| 4-1 | —NHSO$_2$Me | H | H | H | H | H | | 400 |
| 4-2 | —NHCOOMe | H | H | H | H | H | | 380 |
| 4-3 | —NHCOCH$_2$OMe | H | H | H | H | H | | 394 |
| 4-4 | —NHCONMe$_2$ | H | H | H | H | H | | 393 |
| 4-5 | —NHCONHEt | H | H | H | H | H | | 393 |
| 4-6 | —NHCOEt | H | H | H | H | H | | 378 |
| 4-7 | —NHCO$^i$Pr | H | H | H | H | H | | 392 |
| 4-8 | —NHAc | 3-OMe | H | H | H | H | | 394 |
| 4-9 | —NHCOCH$_2$OEt | H | H | H | H | H | | 408 |
| 4-10 | ![structure with Me, OMe, NH-C(=O)] | H | H | H | H | H | | 408 |
| 4-11 | ![structure with Me, OMe, NH-C(=O)] | H | H | H | H | H | | 408 |
| 4-12 | —NHCOOEt | H | H | H | H | H | | 394 |
| 4-13 | ![structure with cyclopropyl-SO$_2$-NH] | H | H | H | H | H | | 426 |
| 4-14 | —NHSO$_2$Et | H | H | H | H | H | | 414 |
| 4-15 | —NHCOO$^i$Pr | H | H | H | H | H | | 408 |
| 4-16 | —NHCOO(CH$_2$)$_2$OMe | H | H | H | H | H | | 424 |
| 4-17 | —NHCONEt$_2$ | H | H | H | H | H | | 421 |
| 4-18 | ![morpholine urea structure] | H | H | H | H | H | | 435 |
| 4-19 | —NHCOCH$_2$CN | H | H | H | H | H | | 389 |
| 4-20 | —NHSO$_2$NHMe | H | H | H | H | H | | 415 |
| 4-21 | —NHSO$_2$NMe$_2$ | H | H | H | H | H | | 429 |
| 4-22 | ![tetrahydrofuran amide structure] | H | H | H | H | H | | 420 |
| 4-23 | —NHCOOMe | H | H | Me | H | H | | 394 |
| 4-24 | —NHCONMe$_2$ | H | H | Me | H | H | | 407 |
| 4-25 | —NHSO$_2$Me | 3-OMe | H | H | H | H | | 430 |
| 4-26 | —NHSO$_2$Me | 2-OMe | H | H | H | H | | 430 |
| 4-27 | —NHSO$_2$Me | 2,3-di OMe | H | H | H | H | | 460 |
| 4-28 | —NHSO$_2$(CH$_2$)$_2$OMe | H | H | H | H | H | | 444 |
| 4-29 | —NHSO$_2$(CH$_2$)$_3$OMe | H | H | H | H | H | | 458 |
| 4-30 | —N(Me)SO$_2$Me | H | H | H | H | H | | 413 |
| 4-31 | —NHCOO(CH$_2$)$_2$OMe | 3-OMe | H | H | H | H | | 454 |

-continued

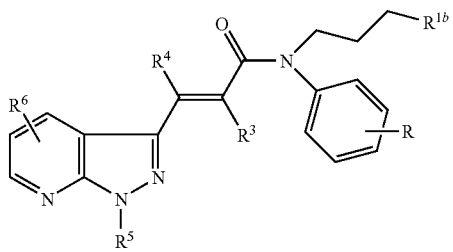

| Examples | R<sup>1b</sup> | R | R³ | R⁴ | R⁵ | R⁶ | Salts | MS(APCI) [M + H]⁺ |
|---|---|---|---|---|---|---|---|---|
| 4-32 | —NHCOO(CH₂)₂OMe | 4-OMe | H | H | H | H | | 454 |
| 4-33 | —NHSO₂Me | 2-Me | H | H | H | H | | 414 |
| 4-34 | —NHSO₂Me | 2-F | H | H | H | H | | 418 |
| 4-35 | —NHSO₂Me | 2-Cl-4-Me | H | H | H | H | | 448/450 |
| 4-36 | —NHSO₂Me | 2-Cl-5-Me | H | H | H | H | | 448/450 |
| 4-37 | —NHCOO(CH₂)₂OMe | H | H | Me | H | H | | 438 |
| 4-38 | ![structure] | H | H | Me | H | H | | 449 |
| 4-39 | —NHCOO(CH₂)₂OMe | 2-OMe | H | H | H | H | | 454 |
| 4-40 | —NHCOO(CH₂)₂OH | H | H | Me | H | H | | 424 |
| 4-41 | ![structure] | H | H | H | H | H | | 470 |
| 4-42 | —NHSO₂Me | 2-Cl-5-OMe | H | H | H | H | | 464/466 |
| 4-43 | —NHSO₂Et | H | H | Me | H | H | | 428 |
| 4-44 | —NHCOCH₂NMe₂ | H | H | Me | H | H | | 421 |
| 4-45 | ![structure] | H | H | Me | H | H | | 422 |
| 4-46 | ![structure] | H | H | Me | H | H | | 410 |
| 4-47 | —NHSO₂(CH₂)₂OMe | H | H | Me | H | H | | 458 |
| 4-48 | —NHSO₂(CH₂)₃OMe | H | H | Me | H | H | | 472 |
| 4-49 | ![structure] | H | H | Me | H | H | | 422 |
| 4-50 | —NHCO'Pr | H | H | Me | H | H | | 406 |
| 4-51 | ![structure] | H | H | Me | H | H | | 434 |

-continued

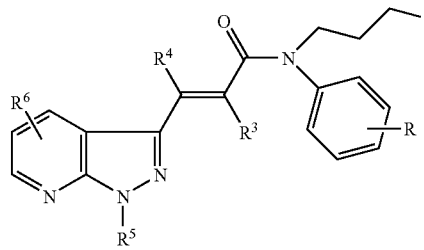

| Examples | $R^{1b}$ | R | $R^3$ | $R^4$ | $R^5$ | $R^6$ | Salts | MS(APCI) $[M + H]^+$ |
|---|---|---|---|---|---|---|---|---|
| 4-52 | (methylcarbamate-tetrahydrofuranyl) | H | H | Me | H | H | | 450 |
| 4-53 | —NHCOCH$_2$NMe$_2$ | 3-OMe | H | Me | H | H | | 451 |
| 4-54 | (methylamide-morpholinyl) | H | H | Me | H | H | | 463 |
| 4-55 | (methylamide-OMe-Me) | 2-F | H | Me | H | H | | 440 |
| 4-56 | —NHCOCH$_2$NMe$_2$ | 4-OMe | H | Me | H | H | | 451 |
| 4-57 | —NHCOCH$_2$NMe$_2$ | 2-F | H | Me | H | H | | 439 |
| 4-58 | —NHCONMe$_2$ | 2-F | H | Me | H | H | | 425 |
| 4-59 | —NHCONHMe | H | H | Me | H | H | | 393 |
| 4-60 | —NHCHO | H | H | Me | H | H | | 364 |
| 4-61 | —NHCONHEt | H | H | Me | H | H | | 407 |

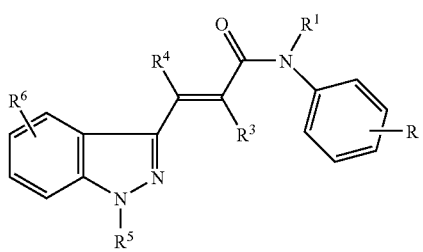

| Examples | $R^1$ | R | $R^3$ | $R^4$ | $R^5$ | $R^6$ | Salts | MS(APCI) $[M + H]^+$ |
|---|---|---|---|---|---|---|---|---|
| 5-1 | —(CH$_2$)$_2$OCON(Me)(CH$_2$)$_2$OH | H | H | H | H | H | | 409 |
| 5-2 | —(CH$_2$)$_2$OH | H | H | H | H | H | | 308 |
| 5-3 | —(CH$_2$)$_2$OH | 4-OMe | H | H | H | H | | 338 |
| 5-4 | —(CH$_2$)$_2$OH | 2-OMe | H | H | H | H | | 338 |
| 5-5 | —(CH$_2$)$_2$OH | 3-OMe | H | H | H | H | | 338 |
| 5-6 | —(CH$_2$)$_2$OMe | H | H | H | H | H | | 322 |
| 5-7 | —(CH$_2$)$_2$OH | 2-Me | H | H | H | H | | 322 |
| 5-8 | —(CH$_2$)$_2$OH | H | H | H | H | 5-F | | 326 |
| 5-9 | —(CH$_2$)$_2$OH | 3-Me | H | H | H | H | | 322 |
| 5-10 | —(CH$_2$)$_2$OH | 4-Me | H | H | H | H | | 322 |
| 5-11 | —(CH$_2$)$_2$OH | 4-F | H | H | H | H | | 326 |
| 5-12 | —(CH$_2$)$_2$OH | 3-F | H | H | H | H | | 326 |
| 5-13 | —CH$_2$CH(Me)OH | H | H | H | H | H | | 322 |
| 5-14 | —(CH$_2$)$_2$OCONHEt | H | H | H | H | H | | 379 |
| 5-15 | —CH$_2$C(Me)$_2$OH | H | H | H | H | H | | 336 |
| 5-16 | —(CH$_2$)$_2$OCONHMe | H | H | H | H | H | | 365 |

-continued

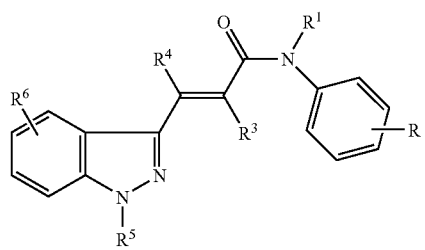

| Examples | R¹ | R | R³ | R⁴ | R⁵ | R⁶ | Salts | MS(APCI) [M + H]⁺ |
|---|---|---|---|---|---|---|---|---|
| 5-17 | —(CH₂)₂OCONMe₂ | H | H | H | H | H | | 379 |
| 5-18 | —(CH₂)₂OMe | 3-Me | H | H | H | H | | 336 |
| 5-19 | —(CH₂)₂OMe | 3-OMe | H | H | H | H | | 352 |
| 5-20 | —(CH₂)₂OMe | 2,3-diOMe | H | H | H | H | | 382 |
| 5-21 | —CH₂CH(Me)OH | 2,3-diOMe | H | H | H | H | | 382 |
| 5-22 | —CH₂C(Me)₂OH | 2,3-diOMe | H | H | H | H | | 396 |
| 5-23 | —CH₂C(Me)₂OH | 3-OMe | H | Me | H | H | | 380 |
| 5-24 | —CH₂CH(Me)OH | 3-OMe | Me | H | H | H | | 366 |
| 5-25 | —(CH₂)₂OH | 3-NMe₂ | H | H | H | H | | 351 |
| 5-26 | —CH₂CH(Me)OH | 3-NMe₂ | H | H | H | H | | 365 |
| 5-27 | propyl 4-hydroxypiperidine-1-carboxylate | H | H | H | H | H | | 435 |
| 5-28 | —(CH₂)₂OMe | H | H | H | Me | H | | 336 |
| 5-29 | propyl morpholine-4-carboxylate | H | H | H | H | H | | 421 |
| 5-30 | —(CH₂)₂OCON(Me)(CH₂)₂OMe | H | H | H | H | H | | 423 |
| 5-31 | —(CH₂)₂OCON(Me)(CH₂)₂OH | H | H | H | Me | H | | 423 |
| 5-32 | —CH₂C(Me)₂OH | 3-NMe₂ | H | Me | H | H | | 393 |
| 5-33 | —(CH₂)₂OCONH(CH₂)₂OH | H | H | H | Me | H | | 489 |
| 5-34 | —(CH₂)₂OCONH(CH₂)₃OH | H | H | H | Me | H | | 423 |
| 5-35 | —(CH₂)₂OCONHMe | H | H | H | Me | H | | 379 |

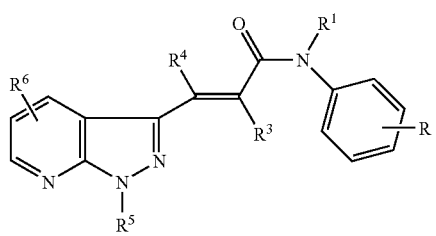

| Examples | R¹ | R | R³ | R⁴ | R⁵ | R⁶ | Salts | MS(APCI) [M + H]⁺ |
|---|---|---|---|---|---|---|---|---|
| 6-1 | —(CH₂)₂OH | H | H | H | H | H | | 309 |
| 6-2 | —CH₂C(Me)₂OH | 3-OMe | H | H | H | H | | 367 |
| 6-3 | —(CH₂)₂OCON(Me)(CH₂)₃OH | H | H | H | H | H | | 424 |
| 6-4 | —CH₂CH(Me)OH | H | H | H | H | H | | 323 |
| 6-5 | —(CH₂)₂OMe | H | H | H | H | H | | 323 |
| 6-6 | —CH₂CH(Me)OH | 3-OMe | H | H | H | H | | 353 |
| 6-7 | —CH₂CH(Me)OH | 3-NMe₂ | H | H | H | H | | 366 |
| 6-8 | —(CH₂)₂OH | 3-NMe₂ | H | H | H | H | | 352 |
| 6-9 | —CH₂C(Me)₂OH | H | H | H | H | H | | 337 |
| 6-10 | —CH₂C(Me)₂OH | 2,3-diOMe | H | H | H | H | | 397 |

-continued

| Examples | R¹ | R | R³ | R⁴ | R⁵ | R⁶ | Salts | MS(APCI) [M + H]⁺ |
|---|---|---|---|---|---|---|---|---|
| 6-11 | —(CH₂)₂OCONHMe | H | H | H | H | H | | 366 |
| 6-12 | —(CH₂)₂OCON(Me)(CH₂)₂OH | H | H | H | H | H | | 410 |
| 6-13 | —(CH₂)₂OCONMe₂ | H | H | H | H | H | | 380.26* |
| 6-14 | propyl morpholine-4-carboxylate | H | H | H | H | H | | 422.23* |
| 6-15 | propyl pyrrolidine-1-carboxylate | H | H | H | H | H | | 406.25* |
| 6-16 | propyl 3-hydroxypiperidine-1-carboxylate | H | H | H | H | H | | 436 |
| 6-17 | —(CH₂)₂OCONH(CH₂)₂OMe | H | H | H | H | H | | 410.24* |
| 6-18 | —(CH₂)₂OCON(Me)(CH₂)₂OMe | H | H | H | H | H | | 424.23* |
| 6-19 | —(CH₂)₂OCON(Me)(CH₂)₂CN | H | H | H | H | H | | 419.31* |
| 6-20 | propyl morpholin-4-ylcarbamate | H | H | H | H | H | | 436.26* |
| 6-21 | —(CH₂)₂OCON(Me)Et | H | H | H | H | H | | 394.25* |
| 6-22 | propyl azetidine-1-carboxylate | H | H | H | H | H | | 392.23* |
| 6-23 | propyl 2-methylpyrrolidine-1-carboxylate | H | H | H | H | H | | 420.26* |
| 6-24 | —CH₂CH(Et)OH | H | H | H | H | H | | 337 |
| 6-25 | —CH₂CH(Et)OH | 3-NMe₂ | H | H | H | H | | 380 |
| 6-26 | —CH₂C(Me)₂OH | 3-OMe-4-Cl | H | H | H | H | | 401/403 |
| 6-27 | —CH₂C(Me)₂OH | 3-OCH₂CF₃ | H | H | H | H | | 435 |
| 6-28 | —CH₂C(Me)₂OH | 3-OMe | H | Me | H | H | | 381 |
| 6-29 | 1-ethylcyclopropan-1-ol | 3-OMe | H | H | H | H | | 365 |
| 6-30 | —CH₂C(Me)₂OH | 3-NMe₂ | H | H | H | H | | 380 |

-continued

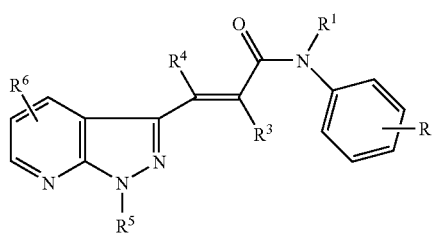

| Examples | R¹ | R | R³ | R⁴ | R⁵ | R⁶ | Salts | MS(APCI) [M + H]⁺ |
|---|---|---|---|---|---|---|---|---|
| 6-31 | —(CH₂)₂OH | 3-OMe | H | H | H | H | | 339 |
| 6-32 | —(CH₂)₂OCON(Me)(CH₂)₂OH | H | H | Me | H | H | | 424 |
| 6-33 | —CH₂C(Me)₂OH | 3-OMe | H | H | H | H | | 367 |
| 6-34 | —CH₂C(Me)₂OH | 4-OMe | H | H | H | H | | 367 |
| 6-35 | —CH₂C(Me)₂OH | 3-F | H | H | H | H | | 355 |
| 6-36 | —CH₂C(Me)₂OH | 3-Me | H | H | H | H | | 351 |
| 6-37 | —CH₂C(Me)₂OH | 2-F | H | H | H | H | | 355 |
| 6-38 | —(CH₂)₂OCONH(CH₂)₂OH | H | H | H | H | H | | 396 |
| 6-39 | —(CH₂)₂OCONH(CH₂)₃OMe | H | H | H | H | H | | 424 |
| 6-40 | —(CH₂)₂OCON[(CH₂)₂OMe]₂ | H | H | H | H | H | | 468 |
| 6-41 | —CH₂C(Me)₂OH | 3-N-morpholino | H | H | H | H | | 422 |
| 6-42 | —(CH₂)₂OCONH(CH₂)₃CH | H | H | H | H | H | | 410 |
| 6-43 | —(CH₂)₂OMe | H | H | Me | H | H | | 337 |
| 6-44 | —CH₂C(Me)₂OH | 2-OMe | H | Me | H | H | | 381 |
| 6-45 | —CH₂C(Me)₂OH | 3-NMe₂ | H | Me | H | H | | 394 |
| 6-46 | —(CH₂)₂OCONMe₂ | H | H | Me | H | H | | 394 |
| 6-47 | propyl (S)-carbamate-CH(Me)CH₂OH | H | H | H | H | H | | 410 |
| 6-48 | —(CH₂)₂OCONH(CH₂)₃OMe | H | H | Me | H | H | | 438 |
| 6-49 | —(CH₂)₂OCONH(CH₂)₂OMe | H | H | Me | H | H | | 424 |
| 6-50 | propyl morpholine-4-carboxylate | H | H | Me | H | H | | 436 |
| 6-51 | —(CH₂)₂OCON(Me)(CH₂)₃OH | H | H | Me | H | H | | 438 |
| 6-52 | propyl 3-hydroxypiperidine-1-carboxylate | H | H | Me | H | H | | 450 |
| 6-53 | —CH(Me)CH₂OH | H | H | Me | H | H | | 337 |
| 6-54 | —(CH₂)₂OCONHMe | H | H | Me | H | H | | 380 |
| 6-55 | propyl 4-hydroxypiperidine-1-carboxylate | H | H | Me | H | H | | 450 |

-continued
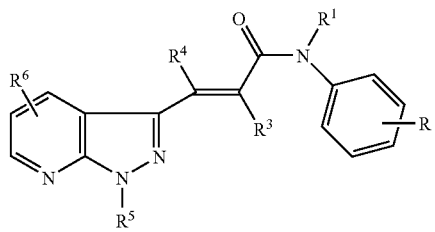
| Examples | R¹ | R | R³ | R⁴ | R⁵ | R⁶ | Salts | MS(APCI) [M + H]⁺ |
|---|---|---|---|---|---|---|---|---|
| 6-56 | propyl-O-C(=O)-N-morpholine-2-CH₂OH | H | H | Me | H | H | | 466 |
| 6-57 | propyl-O-C(=O)-N-morpholine-3-CH₂OH | H | H | Me | H | H | | 466 |
*MS (ESI) [M + H]⁺
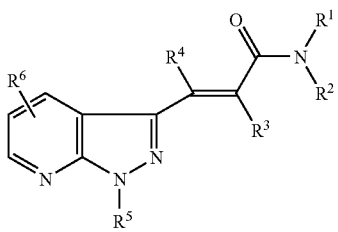
| Examples | R¹ | R² | R³ | R⁴ | R⁵ | R⁶ | Salts | MS(APCI) [M + H]⁺ |
|---|---|---|---|---|---|---|---|---|
| 6-58 | —CH₂C(Me)₂OH | 1-methylindoline-6-yl | H | H | H | H | | 392 |
| 6-59 | —CH₂C(Me)₂OH | 1-methyl-1,2,3,4-tetrahydroquinolin-7-yl | H | H | H | H | | 406 |

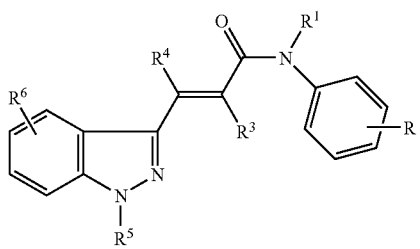

| Examples | R¹ | R | R³ | R⁴ | R⁵ | R⁶ | Salts | MS(APCI) [M + H]⁺ |
|---|---|---|---|---|---|---|---|---|
| 7-1 | —(CH$_2$)$_3$OH | H | H | H | H | H | | 322 |
| 7-2 | —(CH$_2$)$_3$OCONHMe | H | H | H | H | H | | 379 |
| 7-3 | —(CH$_2$)$_3$OCON(Me)(CH$_2$)$_2$OH | H | H | Me | H | H | | 437 |
| 7-4 | —(CH$_2$)$_3$OCONH(CH$_2$)$_3$OH | H | H | Me | H | H | | 437 |
| 7-5 | —(CH$_2$)$_3$OCONHMe | H | H | Me | H | H | | 393 |

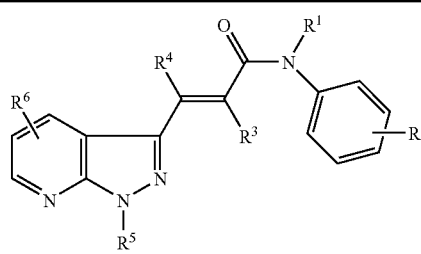

| Examples | R¹ | R | R³ | R⁴ | R⁵ | R⁶ | Salts | MS(APCI) [M + H]⁺ |
|---|---|---|---|---|---|---|---|---|
| 8-1 | —(CH$_2$)$_3$OH | H | H | H | H | H | | 323 |
| 8-2 | —(CH$_2$)$_2$CH(Me)OH | H | H | H | H | H | | 337 |
| 8-3 | —(CH$_2$)$_3$OMe | H | H | H | H | H | | 337 |
| 8-4 | —CH(Me)(CH$_2$)$_2$OH | H | H | H | H | H | | 337 |
| 8-5 | —(CH$_2$)$_3$OCONHMe | H | H | H | H | H | | 380 |
| 8-6 | —(CH$_2$)$_3$OCONH—⟨tetrahydropyran-4-yl⟩ | H | H | H | H | H | | 450.29* |
| 8-7 | —(CH$_2$)$_3$OCONMe$_2$ | H | H | H | H | H | | 394.31* |
| 8-8 | —(CH$_2$)$_3$OCO—morpholinyl | H | H | H | H | H | | 436.29* |
| 8-9 | —(CH$_2$)$_3$OCO—pyrrolidinyl | H | H | H | H | H | | 420.26* |
| 8-10 | —(CH$_2$)$_3$OCON(Me)CH$_2$CONMe$_2$ | H | H | H | H | H | | 465.31* |
| 8-11 | —(CH$_2$)$_3$OCO—(3-hydroxypiperidinyl) | H | H | H | H | H | | 450.3* |
| 8-12 | —(CH$_2$)$_3$OCONH(CH$_2$)$_2$OMe | H | H | H | H | H | | 424.27* |
| 8-13 | —(CH$_2$)$_3$OCON(Me)(CH$_2$)$_2$OMe | H | H | H | H | H | | 438.27* |
| 8-14 | —(CH$_2$)$_3$OCON(Me)CH$_2$CN | H | H | H | H | H | | 419.26* |
| 8-15 | —(CH$_2$)$_3$OCON(Me)(CH$_2$)$_2$CN | H | H | H | H | H | | 433.30* |

-continued

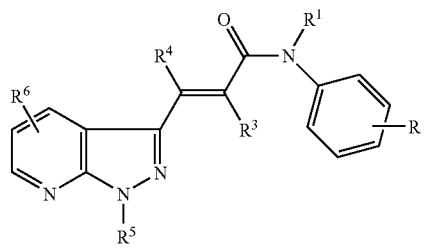

| Examples | R¹ | R | R³ | R⁴ | R⁵ | R⁶ | Salts | MS(APCI) [M + H]⁺ |
|---|---|---|---|---|---|---|---|---|
| 8-16 | —(CH₂)₃OCO—N⟨piperidine⟩—OH | H | H | H | H | H | | 450.27* |
| 8-17 | —(CH₂)₃OCON(Me)Et | H | H | H | H | H | | 408.25* |
| 8-18 | —(CH₂)₃OCONHCH₂CONMe₂ | H | H | H | H | H | | 451.31* |
| 8-19 | —(CH₂)₃OCO—N⟨azetidine⟩ | H | H | H | H | H | | 406.28* |
| 8-20 | —(CH₂)₃OCO—N⟨2-Me-pyrrolidine⟩ | H | H | H | H | H | | 434.3* |
| 8-21 | —(CH₂)₃OCON(Me)(CH₂)₂OH | H | H | H | H | H | | 424 |
| 8-22 | —CH₂C(Me)₂CH₂OH | H | H | H | H | H | | 351 |
| 8-23 | —(CH₂)₃OCON(Me)(CH₂)₃OH | H | H | H | H | H | | 438 |
| 8-24 | —(CH₂)₃OCO—N⟨(2S)-2-(hydroxymethyl)pyrrolidine⟩ | H | H | H | H | H | | 450 |
| 8-25 | —(CH₂)₃OCO—N⟨(2R)-2-(hydroxymethyl)pyrrolidine⟩ | H | H | H | H | H | | 450 |
| 8-26 | —CH₂CH(Me)CH₂OH | H | H | H | H | H | | 337 |
| 8-27 | —(CH₂)₃OCONH(CH₂)₂OH | H | H | H | H | H | | 410 |
| 8-28 | —(CH₂)₃OCONH(CH₂)₃OMe | H | H | H | H | H | | 438 |
| 8-29 | —(CH₂)₃OCON[(CH₂)₂OMe]₂ | H | H | H | H | H | | 482 |
| 8-30 | —(CH₂)₃OCONH(CH₂)₂OH | H | H | H | Me | H | | 424 |
| 8-31 | —(CH₂)₃OCONHMe | H | H | H | Me | H | | 394 |
| 8-32 | —(CH₂)₃OCON(Me)(CH₂)₂OH | H | H | H | Me | H | | 438 |
| 8-33 | —(CH₂)₃OCONH(CH₂)₃OMe | H | H | H | Me | H | | 452 |
| 8-34 | —(CH₂)₃OCONH(CH₂)₂OMe | H | H | H | Me | H | | 438 |
| 8-35 | —(CH₂)₃OCO—N⟨piperazine⟩N—Ac | H | H | H | Me | H | | 491 |
| 8-36 | —(CH₂)₃OCON(Me)(CH₂)₃OH | H | H | H | Me | H | | 452 |
| 8-37 | —(CH₂)₃OCONMe₂ | H | H | H | Me | H | | 408 |
| 8-38 | —(CH₂)₃OMe | H | H | H | Me | H | | 351 |
| 8-39 | —(CH₂)₃OCO—N⟨piperidine⟩—OH | H | H | H | Me | H | | 464 |

*MS (ESI) [M + H]⁺

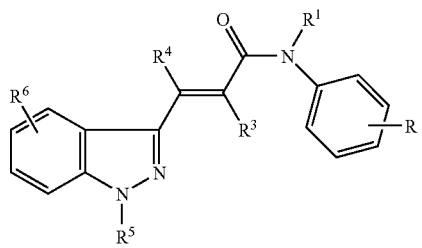

| Examples | R¹ | R | R³ | R⁴ | R⁵ | R⁶ | Salts | MS(APCI) [M+H]⁺ |
|---|---|---|---|---|---|---|---|---|
| 9-1 | —(CH₂)₃SO₂Me | H | H | H | H | H | | 384 |
| 9-2 | —(CH₂)₂CONHMe | H | H | H | H | H | | 349 |
| 9-3 | —(CH₂)₃-morpholine | H | H | H | H | H | | 391 |
| 9-4 | —CH₂CN | H | H | H | H | H | | 303 |
| 9-5 | —(CH₂)₂-morpholine | H | H | H | H | H | | 377 |
| 9-6 | —CH₂-thiazole | H | H | H | H | H | | 361 |
| 9-7 | —CH₂CONHMe | H | H | H | H | H | | 335 |
| 9-8 | —(CH₂)₂CONMe₂ | H | H | H | H | H | | 363 |
| 9-9 | —(CH₂)₂CO-morpholine | H | H | H | H | H | | 405 |
| 9-10 | —(CH₂)₂N(Me)Ac | H | H | H | H | H | | 363 |
| 9-11 | —(CH₂)₃SO₂Me | 4-Me | H | H | H | H | | 398 |
| 9-12 | —(CH₂)₃SO₂Me | 3-Me | H | H | H | H | | 398 |
| 9-13 | —(CH₂)₃SO₂Me | 2-Me | H | H | H | H | | 398 |
| 9-14 | —(CH₂)₃SO₂Ph | H | H | H | H | H | | 446 |
| 9-15 | —(CH₂)₂-(3-oxomorpholine) | H | H | H | H | H | | 391 |
| 9-16 | —CH₂CH(Me)OH | H | H | H | H | H | | 322 |
| 9-17 | —(CH₂)₂-(3-oxopiperazine-N-COO'Bu) | H | H | H | H | H | | 490 |
| 9-18 | —(CH₂)₂-(N-Ac piperazine) | H | H | H | H | H | | 418 |
| 9-19 | —(CH₂)₂N(Me)(CH₂)₂OMe | H | H | H | H | H | | 379 |
| 9-20 | —(CH₂)₂-(3-oxopiperazine) | H | H | H | H | H | | 390 |

-continued

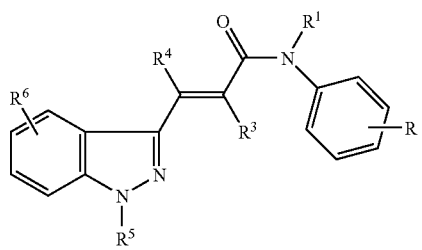

| Examples | R¹ | R | R³ | R⁴ | R⁵ | R⁶ | Salts | MS(APCI) [M + H]⁺ |
|---|---|---|---|---|---|---|---|---|
| 9-21 | —(CH₂)₂NHEt | H | H | H | H | H | HCl | 335 |
| 9-22 | —(CH₂)₂-N(piperazine)N—Me | H | H | H | H | H | | 390 |
| 9-23 | —(CH₂)₂CONH₂ | H | H | H | H | H | | 335 |
| 9-24 | —(CH₂)₂N(Et)CHO | H | H | H | H | H | | 363 |
| 9-25 | —(CH₂)₂N(Et)COOMe | H | H | H | H | H | | 393 |
| 9-26 | —(CH₂)₂N(Et)CONHEt | H | H | H | H | H | | 406 |
| 9-27 | —(CH₂)₃SO₂Me | 3-OMe | H | H | H | H | | 414 |
| 9-28 | —(CH₂)₂OMe | 3-Me | H | H | H | H | | 336 |
| 9-29 | —(CH₂)₂OMe | 3-OMe | H | H | H | H | | 352 |
| 9-30 | —(CH₂)₃SO₂Me | 2,3-diOMe | H | H | H | H | | 444 |
| 9-31 | —(CH₂)₂-pyrazolyl | H | H | H | H | H | | 358 |
| 9-32 | —CH₂-(1H-pyrazol-3-yl) | H | H | H | H | H | | 344 |
| 9-33 | —CH₂-(2-pyridyl) | H | H | H | H | H | | 355 |
| 9-34 | —(CH₂)₂OMe | 2,3-diOMe | H | H | H | H | | 382 |
| 9-35 | —(CH₂)₃SO₂Me | 3-OEt | H | H | H | H | | 428 |
| 9-36 | —(CH₂)₃SO₂Me | 3-OⁱPr | H | H | H | H | | 442 |
| 9-37 | —(CH₂)₂SO₂Me | H | H | H | H | H | | 370 |
| 9-38 | —CH₂-(N-formyl-pyrrolidin-2-yl) | H | H | H | H | H | | 375 |
| 9-39 | —(CH₂)₂-N(thiomorpholine S-oxide) | H | H | H | H | H | | 409 |
| 9-40 | —(CH₂)₂-N(thiomorpholine S,S-dioxide) | H | H | H | H | H | | 425 |
| 9-41 | —(CH₂)₂-N(3-oxopiperazinyl) | H | H | H | H | H | | 390 |
| 9-42 | —CH₂-(5-oxopyrrolidin-2-yl) | H | H | H | H | H | | 361 |

-continued

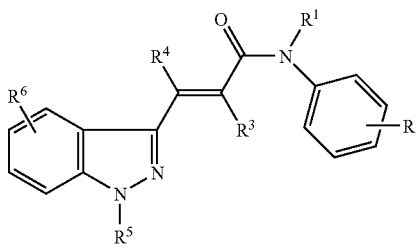

| Examples | R¹ | R | R³ | R⁴ | R⁵ | R⁶ | Salts | MS(APCI) [M + H]⁺ |
|---|---|---|---|---|---|---|---|---|
| 9-43 | —(CH₂)₂—N(CH₂CH₂)₂N—Ac | H | H | H | H | H | | 432 |
| 9-44 | —CH₂-(3-pyridyl) | H | H | H | H | H | | 355 |
| 9-45 | —(CH₂)₂N(Me)COCH₂OMe | H | H | H | H | H | | 393 |
| 9-46 | —(CH₂)₂N(Me)COCH₂CN | H | H | H | H | H | | 388 |
| 9-47 | —(CH₂)₂N(Me)COCH₂NMe₂ | H | H | H | H | H | | 406 |
| 9-48 | —(CH₂)₂N(Me)COOMe | H | H | H | H | H | | 379 |
| 9-49 | —(CH₂)₂N(Me)CONHEt | H | H | H | H | H | | 392 |
| 9-50 | —(CH₂)₂N(Me)COO(CH₂)₂OMe | H | H | H | H | H | | 423 |
| 9-51 | —(CH₂)₂NHNHAc | H | H | H | H | H | | 364 |
| 9-52 | —(CH₂)₂N(Me)CHO | H | H | H | H | H | | 349 |
| 9-53 | —(CH₂)₂N(Me)COCH(Me)CN | H | H | H | H | H | | 402 |
| 9-54 | —(CH₂)₂-(4-(hydroxymethyl)pyrazol-1-yl) | H | H | H | H | H | | 388 |
| 9-55 | —(CH₂)₃SO₂Me | 3-OMe | H | Me | H | H | | 428 |
| 9-56 | —(CH₂)₂NHAc | 3-OMe | Me | H | H | H | | 393 |
| 9-57 | —CH₂CH(Me)OH | 3-OMe | Me | H | H | H | | 366 |
| 9-58 | —(CH₂)₂NHCOOMe | H | Me | H | H | H | | 379 |
| 9-59 | —(CH₂)₃SO₂NMe₂ | H | H | H | H | H | | 413 |
| 9-60 | —(CH₂)₃SO₂NMe₂ | 3-OMe | H | H | H | H | | 443 |
| 9-61 | —CH₂CH(Me)OH | 3-NMe₂ | Me | H | H | H | | 365 |
| 9-62 | —(CH₂)₃SO₂Me | H | H | Me | H | H | | 398 |
| 9-63 | —(CH₂)₂OMe | H | H | Me | H | H | | 336 |
| 9-64 | —(CH₂)₂-(thiomorpholine-1,1-dioxide) | H | H | Me | H | H | | 439 |

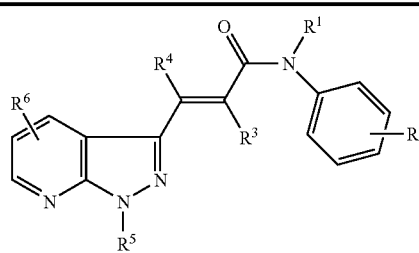

| Examples | R¹ | R | R³ | R⁴ | R⁵ | R⁶ | Salts | MS(APCI) [M + H]⁺ |
|---|---|---|---|---|---|---|---|---|
| 10-1 | —CH₂CH(Me)OH | H | H | H | H | H | | 323 |
| 10-2 | —(CH₂)₂OMe | H | H | H | H | H | | 323 |

-continued

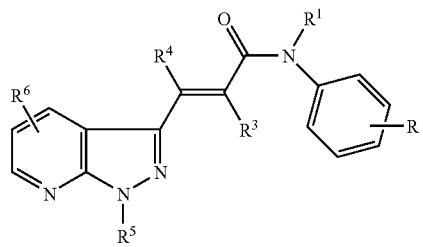

| Examples | R¹ | R | R³ | R⁴ | R⁵ | R⁶ | Salts | MS(APCI) [M + H]⁺ |
|---|---|---|---|---|---|---|---|---|
| 10-3 | —CH₂CN | H | H | H | H | H | | 304 |
| 10-4 | —(CH₂)₂-(pyrazol-1-yl) | H | H | H | H | H | | 359 |
| 10-5 | —CH₂-(1H-pyrazol-5-yl) | H | H | H | H | H | | 345 |
| 10-6 | —(CH₂)₃SO₂Me | 3-OMe | H | H | H | H | | 415 |
| 10-7 | —CH₂CH(Me)OH | 3-OMe | H | H | H | H | | 353 |
| 10-8 | —CH₂CH(Me)OH | 3-NMe₂ | H | H | H | H | | 366 |
| 10-9 | —(CH₂)₂CH(Me)OH | H | H | H | H | H | | 337 |
| 10-10 | —(CH₂)₂CN | H | H | H | H | H | | 318 |
| 10-11 | —(CH₂)₃OMe | H | H | H | H | H | | 337 |
| 10-12 | —CH(Me)(CH₂)₂OH | H | H | H | H | H | | 337 |
| 10-13 | —CH₂CH(OH)Et | 3-NMe₂ | H | H | H | H | | 380 |
| 10-14 | —CH₂C(Me)₂CH₂OH | H | H | H | H | H | | 351 |
| 10-15 | 1-ethyl-1-hydroxycyclopropyl | 3-OMe | H | H | H | H | | 365 |
| 10-16 | —CH₂CH(Me)CH₂OH | H | H | H | H | H | | 337 |
| 10-17 | —(CH₂)₃N(Me)SO₂Me | H | H | H | H | H | | 413 |
| 10-18 | —(CH₂)₂-morpholin-4-yl | H | H | Me | H | H | | 392 |
| 10-19 | —(CH₂)₃-morpholin-4-yl | H | H | Me | H | H | HCl | 406 |
| 10-20 | —(CH₂)₂-(1,1-dioxothiomorpholin-4-yl) | H | H | Me | H | H | | 440 |
| 10-21 | —(CH₂)₂-(4-acetylpiperazin-1-yl) | H | H | Me | H | H | | 433 |
| 10-22 | —(CH₂)₂-(3-fluoropyrrolidin-1-yl) | H | H | Me | H | H | | 394 |
| 10-23 | —(CH₂)₂-(4-acetylpiperazin-1-yl) | 3-OMe | H | Me | H | H | | 463 |
| 10-24 | —(CH₂)₂-(4-methyl-3-oxopiperazin-1-yl) | H | H | Me | H | H | | 419 |

-continued
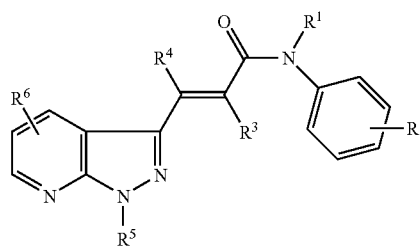
| Examples | R¹ | R | R³ | R⁴ | R⁵ | R⁶ | Salts | MS(APCI) [M + H]⁺ |
|---|---|---|---|---|---|---|---|---|
| 10-25 | —(CH₂)₂—N(pyrrolidine-3-yl with N(Me)Ac) | H | H | Me | H | H | | 447 |
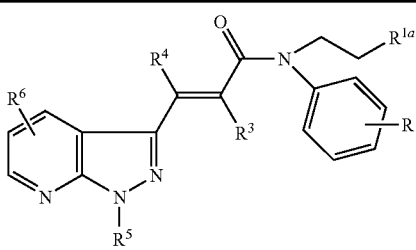
| Examples | R¹ᵃ | R | R³ | R⁴ | R⁵ | R⁶ | Salts | MS(APCI) [M + H]⁺ |
|---|---|---|---|---|---|---|---|---|
| 10-26 | —N(piperazine)N—Ac | 4-Me | H | Me | H | H | | 447 |
| 10-27 | —N(piperazine)N—Ac | 3-Me | H | Me | H | H | | 447 |
| 10-28 | —N(piperidine-4-yl)—SO₂Me | H | H | Me | H | H | | 468 |
| 10-29 | —N(piperazine with Me)N—Ac | H | H | Me | H | H | | 447 |
| 10-30 | N(Me)(CH₂)₂N(Me)SO₂Me | H | H | Me | H | H | | 471 |
| 10-31 | —N(piperazine)N—Ac | 3-Cl | H | Me | H | H | | 467 |
| 10-32 | —N(pyrrolidin-3-yl)—SO₂Me | H | H | Me | H | H | | 454 |

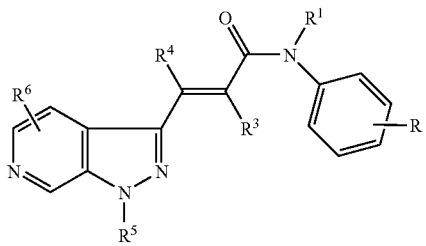

| Examples | R¹ | R | R³ | R⁴ | R⁵ | R⁶ | Salts | MS (APCI) [M + H]⁺ |
|---|---|---|---|---|---|---|---|---|
| 11-1 | —(CH₂)₃NHCOOMe | H | H | H | H | H | | 380 |

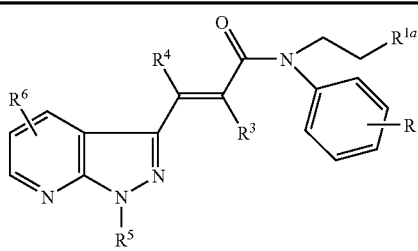

| Examples | R¹ᵃ | R | R³ | R⁴ | R⁵ | R⁶ | Salts | MS(APCI) [M + H]⁺ |
|---|---|---|---|---|---|---|---|---|
| 12-1 | —NHCOOMe | 4-Me | H | Et | H | H | | 408 |
| 12-2 | OCON(Me)₂ | H | H | F | H | H | | 398 |
| 12-3 | 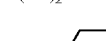 | H | H | F | H | H | | 440 |
| 12-4 | OCON(Me)(CH₂)₃OH | H | H | F | H | H | | 442 |
| 12-5 | OMe | H | H | F | H | H | | 341 |
| 12-6 | NHCOOEt | H | H | F | H | H | | 398 |
| 12-7 | NHCOiPr | H | H | F | H | H | | 396 |
| 12-8 | OCONHMe | H | H | F | H | H | | 384 |

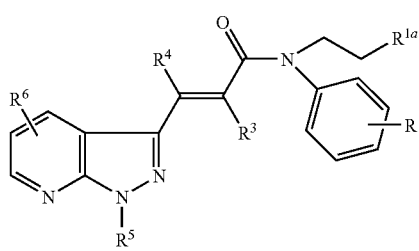

| Examples | R¹ᵇ | R | R³ | R⁴ | R⁵ | R⁶ | Salts | MS(APCI) [M + H]⁺ |
|---|---|---|---|---|---|---|---|---|
| 12-9 | NHSO₂Me | H | H | F | H | H | | 418 |
| 12-10 | NHSO₂Me | 4-Me | H | F | H | H | | 432 |
| 12-11 | OCONHMe | H | H | F | H | H | | 398 |
| 12-12 | NHCOOMe | H | H | F | H | H | | 398 |

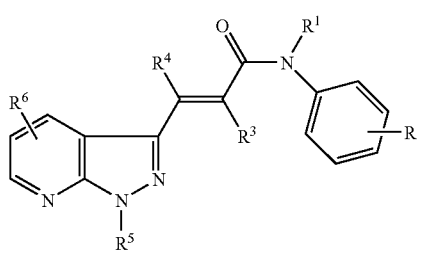

| Examples | R¹ | R | R³ | R⁴ | R⁵ | R⁶ | Salts | MS(APCI) [M + H]⁺ |
|---|---|---|---|---|---|---|---|---|
| 12-13 | —CH₂C(Me)₂OH | 3-OMe | H | F | H | H | | 385 |

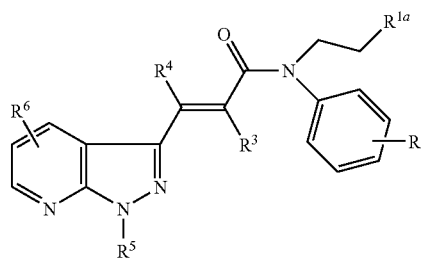
| Examples | R$^{1a}$ | R | R$^3$ | R$^4$ | R$^5$ | R$^6$ | Salts | MS(APCI) [M + H]$^+$ |
|---|---|---|---|---|---|---|---|---|
| 13-1 | —N(piperazine)N—CONMe$_2$ | H | H | Me | H | H | | 462 |
| 13-2 | —N(pyrrolidine)—NHSO$_2$Me | H | H | Me | H | H | | 469 |
| 13-3 | —N(piperazine)N—CHO | H | H | Me | H | H | | 419 |
| 13-4 | —N(piperazine)N—CO-isoxazole | H | H | Me | H | H | | 486 |
| 13-5 | —N(piperazine)N—SO$_2$Et | H | H | Me | H | H | | 483 |
| 13-6 | —N(piperazine)N—SO$_2$NMe$_2$ | H | H | Me | H | H | | 498 |
| 13-7 | —N(piperazine)N—SO$_2$Me | H | H | Me | H | H | | 469 |
| 13-8 | —N(piperazine)N—COOMe | H | H | Me | H | H | | 449 |
| 13-9 | —N(piperazine)N—COC(Me)$_2$CN | H | H | Me | H | H | | 486 |

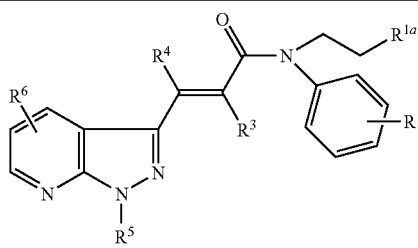

| Examples | $R^{1a}$ | R | $R^3$ | $R^4$ | $R^5$ | $R^6$ | Salts | MS(APCI) $[M + H]^+$ |
|---|---|---|---|---|---|---|---|---|
| 13-10 | —N⟨ ⟩N—COCH$_2$CN | H | H | H | H | H | | 443 |
| 13-11 | —N⟨ ⟩N—CHO | H | H | H | H | H | | 404 |

Experiment 1: Effects on Atrial Effective Refractory Period (ERP) in Anesthetic Dogs (1) Surgery Mongrel dogs of either sex were anesthesized by intravenously administering pentobarbital sodium (induction: 30 mg/kg, continuance: 5 mg/kg/hr) and cannulated into their respiratory tracts to give artificial respiration (15 cc×20 cycles/min). Each catheter for continuous anesthesia and sample administration was respectively inserted into their ambilateral median antebrachial veins. A catheter was inserted into left femoral veins, and KN fluid replacement 3B (Otsuka Pharmaceutical Co., Ltd.) was continuously administered (50 to 100 ml/hr). Blood pressure was measured by a pressure-distortion amplifier via a pressure transducer from the catheter inserted into left femoral artery, and heart rate was measured by pulse wave as a trigger, respectively. After median thoracotomy, a pericardium was dissected to expose heart, and electrodes for electrical stimulation and myocardial electrographic measurement were installed in atrium. An electrode for electrocardiographic measurement was installed in body surface (Induction II).

(2) Measurement of ERP

Atrial ERP was measured by using S1-S2 extrastimulus technique. A fundamental stimulus cycle was 200 ms, square-wave stimulus, which were 2 to 4 times of thresholds inducing excitation and 2 ms wide, were applied. After 8 time continuous S1 stimulus, S2 stimulus were applied and shortened by 5 ms in S1-S2 connection phase. The longest S1-S2 interval which atrial activation associated with S2 stimulus disappeared was assumed to be ERP. Existence or nonexistence of atrial activations was judged from atrial electrogram. During rest, it was confirmed that ERP (ms) would be stably obtained more than twice, and then sample or solvent was intravenously administered. A given time after drug administration, ERP was measured. Comparing ERP after and before starting drug administration, a rate of change (%) was calculated.

As a result, the preferable compounds of the present invention, particularly compounds of the following Table, showed over 10% of ERP extension activities by 1 mg/kg administration.

| Examples | ERP extension activities (1 mg/kg) |
|---|---|
| 1-2 | 13.2% |
| 1-7 | 15.0% |
| 1-12 | 10.0% |
| 1-32 | 10.5% |
| 1-45 | 12.2% |
| 1-81 | 18.4% |
| 2-41 | 15.8% |
| 2-53 | 15.0% |
| 4-3 | 15.8% |
| 4-8 | 14.3% |
| 4-55 | 15.0% |
| 5-10 | 15.8% |
| 5-34 | 12.2% |
| 6-5 | 10.0% |
| 6-30 | 10.0% |
| 6-32 | 10.0% |
| 6-52 | 20.0% |
| 8-5 | 15.9% |
| 9-27 | 12.2% |
| 10-21 | 22.2% |

INDUSTRIAL APPLICABILITY

The compound of the present invention or a pharmaceutically acceptable salt thereof has an $I_{Kur}$ blocking activity and is useful for preventing or treating cardiac arrhythmia such as atrial fibrillation.

The invention claimed is:

1. A compound of formula (I):

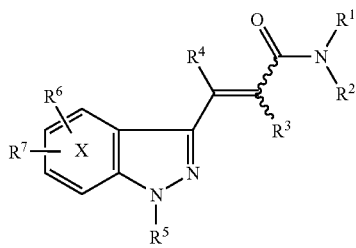

wherein ring X is benzene or pyridine;
R¹ is a substituted alkyl;
R² is an optionally substituted aryl or an optionally substituted heterocyclic group;
R³ is hydrogen or an alkyl;
R⁴ is hydrogen, a halogen or an alkyl;
R⁵ is hydrogen or an alkyl;
R⁶ and R⁷ are the same or different and each hydrogen or a halogen; or a pharmaceutically acceptable salt thereof.

2. A compound of formula (1-a):

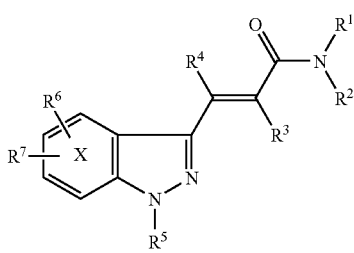

wherein ring X is benzene or pyridine;
R¹ is a substituted alkyl;
R² is an optionally substituted aryl or an optionally substituted heterocyclic group;
R³ is hydrogen or an alkyl;
R⁴ is hydrogen, a halogen or an alkyl;
R⁵ is hydrogen or an alkyl;
R⁶ and R⁷ are the same or different and each hydrogen or a halogen; or a pharmaceutically acceptable salt thereof.

3. The compound or a pharmaceutically acceptable salt thereof as claimed in either one of claims 1 or 2, wherein R¹ is an alkyl substituted with 1 or 2 group(s) selected from hydroxyl, an optionally substituted amino, an alkylsulfonyl, an alkoxy, an optionally substituted heterocyclic group, an optionally substituted ureido, an optionally substituted carbamoyloxy and an optionally substituted heterocyclic group-substituted carbonyloxy.

4. The compound or a pharmaceutically acceptable salt thereof as claimed in either one of claims 1 or 2, wherein R² is an optionally substituted benzene.

5. The compound or a pharmaceutically acceptable salt thereof as claimed in either one of claims 1 or 2, wherein R³ and R⁴ are hydrogen.

6. The compound or a pharmaceutically acceptable salt thereof as claimed in either one of claims 1 or 2, wherein R³ is hydrogen and R⁴ is an alkyl.

7. The compound or a pharmaceutically acceptable salt thereof as claimed in either one of claims 1 or 2, wherein R³ is an alkyl and R⁴ is hydrogen.

8. The compound or a pharmaceutically acceptable salt thereof as claimed in either one of claims 1 or 2, wherein R³ is hydrogen and R⁴ is a halogen.

9. The compound or a pharmaceutically acceptable salt thereof as claimed in either claims 1 or 2, wherein R⁶ and R⁷ are hydrogen.

10. A medicament comprising the compound or a pharmaceutically acceptable salt thereof as claimed in either one of claims 1 or 2.

11. An $I_{Kur}$ blocker comprising as an active ingredient the compound or a pharmaceutically acceptable salt thereof as claimed in either one of claims 1 or 2.

12. A method of treatment for cardiac arrhythmia, comprising administering to a patient a therapeutically effective amount of the compound or a pharmaceutically acceptable salt thereof as claimed in either one of claims 1 or 2.

13. A method of treatment for atrial fibrillation, comprising administering to a patient a therapeutically effective amount of the compound or a pharmaceutically acceptable salt thereof as claimed in either one of claims 1 or 2.

* * * * *